United States Patent
Chen et al.

(10) Patent No.: US 8,048,886 B2
(45) Date of Patent: Nov. 1, 2011

(54) SUBSTITUTED PYRAZINE-3-ONE-DERIVATIVES AS IAP INHIBITORS

(75) Inventors: Zhuoliang Chen, Cambridge, MA (US); Run-Ming David Wang, Cambridge, MA (US); Ming Chen, Cambridge, MA (US); Christopher Sean Straub, Cambridge, MA (US); Leigh Zawel, Cambridge, MA (US)

(73) Assignee: Novartis AG, Basel (CH)

( * ) Notice: Subject to any disclaimer, the term of this patent is extended or adjusted under 35 U.S.C. 154(b) by 235 days.

(21) Appl. No.: 12/518,184

(22) PCT Filed: Dec. 7, 2007

(86) PCT No.: PCT/US2007/025096
§ 371 (c)(1),
(2), (4) Date: Jun. 8, 2009

(87) PCT Pub. No.: WO2008/073305
PCT Pub. Date: Jun. 19, 2008

(65) Prior Publication Data
US 2010/0249405 A1   Sep. 30, 2010

Related U.S. Application Data

(60) Provisional application No. 60/873,436, filed on Dec. 7, 2006.

(51) Int. Cl.
*A61K 31/4965* (2006.01)

(52) U.S. Cl. .......... 514/255.06; 544/120; 544/333; 544/407; 548/125; 548/202; 548/254; 548/255; 548/444; 548/503; 548/518; 549/398; 585/26

(58) Field of Classification Search ............ 514/255.06; 544/120, 333, 407; 546/268.1; 548/125, 548/202, 254, 255, 444, 503, 518; 549/398; 585/26
See application file for complete search history.

(56) References Cited

FOREIGN PATENT DOCUMENTS

| WO | WO 2006/017295 A2 | 2/2006 |
| WO | WO 2006/133147 A2 | 12/2006 |
| WO | WO 2007/101347 A1 | 9/2007 |

*Primary Examiner* — James O Wilson
*Assistant Examiner* — Douglas M Willis

(57) ABSTRACT

The present invention relates to novel IAP inhibitor compounds of formula I:

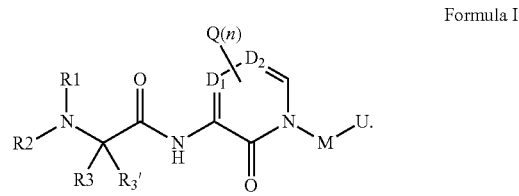

Formula I

4 Claims, No Drawings

SUBSTITUTED PYRAZINE-3-ONE-DERIVATIVES AS IAP INHIBITORS

This application is a U.S. National Phase filing of International Application Serial No. PCT/US2007/025096 filed 7 Dec. 2007 and claims priority to U.S. Provisional Application Ser. No. 60/873,436 filed 7 Dec. 2006, the contents of which are incorporated herein by reference in their entirety.

SUMMARY

The present invention relates generally to novel compounds that inhibit the binding of the Smac protein to Inhibitor of Apoptosis Proteins (IAPs). The present invention includes novel compounds, novel compositions, methods of their use and methods of their manufacture, wherein such compounds are generally pharmacologically useful as agents in therapies whose mechanism of action rely on the inhibition of the IAP/caspase9 or Smac/IAP interaction, and more particularly useful in therapies for the treatment of proliferative diseases, including cancer.

BACKGROUND

Programmed cell death plays a critical role in regulating cell number and in eliminating stressed or damaged cells from normal tissues. Indeed, the network of apoptotic signaling mechanisms inherent in most cell types provides a major barrier to the development and progression of human cancer. Since most commonly used radiation and chemotherapies rely on activation of apoptotic pathways to kill cancer cells, tumor cells which are capable of evading programmed cell death often become resistant to treatment.

Apoptosis signaling networks are classified as either extrinsic when mediated by death receptor-ligand interactions or intrinsic when mediated by cellular stress and mitochondrial permeabilization. Both pathways ultimately converge on individual Caspases. Once activated, Caspases cleave a number of cell death-related substrates, effecting destruction of the cell.

Tumor cells have devised a number of strategies to circumvent apoptosis. One recently reported molecular mechanism involves the over expression of members of the IAP family. IAPs sabotage apoptosis by directly interacting with and neutralizing Caspases. The prototype IAPs, XIAP and cIAP have three functional domains referred to as BIR 1, 2 & 3 domains. BIR3 domain interacts directly with Caspase 9 and inhibits its ability to bind and cleave its natural substrate, Procaspase 3.

It has been reported that a proapoptotic mitochondrial protein, Smac (also known as DIABLO), is capable of neutralizing XIAP and/or cIAP by binding to a peptide binding pocket (Smac binding site) on the surface of BIR3 thereby precluding interaction between XIAP and/or cIAP and Caspase 9. Binding of peptides derived from Smac has also been reported to trigger autocatalytic polyubiquitination and subsequent proteosome-mediated degradation of CIAP1. The present invention relates to therapeutic molecules that bind to the Smac binding pocket thereby promoting Caspase activation. Such therapeutic molecules are useful for the treatment of proliferative diseases, including cancer.

SUMMARY OF THE INVENTION

The present invention relates generally to novel compounds that mimic the binding of the Smac protein to Inhibitor of Apoptosis Proteins (IAPs). The present invention includes novel compounds, novel compositions, methods of their use and methods of their manufacture, where such compounds are generally pharmacologically useful as agents in therapies whose mechanism of action rely on the inhibition of the IAP/Caspase9 or Smac/IAP interaction, and more particularly useful in therapies for the treatment of proliferative diseases, including cancer.

The present invention relates to compounds of the formula (I):

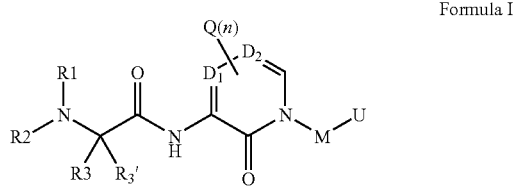

Formula I and pharmaceutically acceptable salts thereof, wherein $R_1$ is H, $C_1$-$C_4$ alkyl, $C_2$-$C_4$ alkenyl, $C_2$-$C_4$ alkynyl or $C_3$-$C_{10}$ cycloalkyl, which $R_1$ may be unsubstituted or substituted;

$R_2$ is H, $C_1$-$C_4$ alkyl, $C_2$-$C_4$ alkenyl, $C_2$-$C_4$ alkynyl, or $C_3$-$C_{10}$ cycloalkyl, which $R_2$ may be unsubstituted or substituted; and $R_1$ and $R_2$ may be taken together to form a ring or het;

$R_3$ and $R_3'$ are independently H, $CF_3$, $C_2F_5$, $C_1$-$C_4$ alkyl, $C_2$-$C_4$ alkenyl, $C_2$-$C_4$ alkynyl, $CH_2$—Z, or $R_2$ and $R_3$ form het, wherein alkyl, alkenyl, alkynyl or het may be unsubstituted or substituted; and Z is H, OH, F, Cl, $CH_3$, $CH_2Cl$, $CH_2F$ or $CH_2OH$;

$D_1$ and $D_2$ are independently C, CH, or N, wherein at least one of $D_1$ or $D_2$ is N;

each Q is independently H, F, Cl, Br, I, $C_1$-$C_{10}$ alkyl, $C_1$-$C_{10}$ alkoxy, aryl $C_1$-$C_{10}$ alkoxy, het $C_1$-$C_{10}$ alkoxy, OH, O—$C_1$-$C_{10}$-alkyl, $(CH_2)_{0-6}$—$C_3$-$C_7$ cycloalkyl, aryl, het, aryl $C_1$-$C_{10}$ alkyl, het $C_1$-$C_{10}$ alkyl, O—$(CH_2)_{0-6}$ aryl, O—$(CH_2)_{0-6}$ het, —$OR_{11}$, $C(O)R_{11}$, —$C(O)N(R_{11})(R_{12})$, $N(R_{11})(R_{12})$, $SR_{11}$, $S(O)R_{11}$, $S(O)_2R_{11}$, $S(O)_2$—$N(R_{11})(R_{12})$, $NR_{11}$—$C(O)$—$R_{12}$, or $NR_{11}$—$S(O)_2$—$R_{12}$, wherein alkyl, cycloalkyl, aryl and het are unsubstituted or substituted, n is 0, 1, or 2, and independent Q's may be joined to form a 5-10 membered ring;

M is $C(R_4)(R_5)$, C(O), C(S), S, S(O), $S(O)_2$, O, $N(R_4)$, or a bond;

U is selected from:

(a) $CON(R_6)(R_7)$, $CN(R_6)(R_7)$, $SO_m$, $N(R_6)(R_7)$, $R_4$, $C(R_4)(R_5)O(R_6)$, $C(R_4)(R_5)$ $S(O)_mR_6$, $C(R_4)(R_5)N(R_6)(R_7)$, $N(R_6)(R_7)$, $O(R_6)$, wherein m is 0, 1, or 2;

$R_4$, $R_5$, $R_6$ and $R_7$ are independently H, halo, $C_{0-10}$ alkyl, $C_{0-10}$ alkyl-aryl, $C_{0-10}$ alkyl-het, $(CH_2)_{0-6}$—$C_3$-$C_7$cycloalkyl, $(CH_2)_{0-6}$—$C_3$-$C_7$cycloalkyl-aryl, $(CR_4R_5)_{0-6}$—$(CH)_{0-1}$ $(aryl)_{1-2}$, or $(CR_4R_5)_{0-6}$—$(CH)_{0-1}(het)_{1-2}$, wherein independent $R_4$, $R_5$, $R_6$, and $R_7$ may be substituted or unsubstituted and may be joined to form a 4-10 membered ring; or (b)

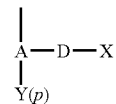

wherein A is an aromatic ring, a 5-7 het or an 8-12 membered fused ring system that may include an aromatic ring, or one 5-7 het containing 1, 2, or 3 heteroring atoms selected from N, O and S, which any position of the rings is unsubstituted or substituted with one or more Q's;

D is selected from (a) a bond, —CO—, —C(O)—$C_{1-7}$ alkylene or arylene, —$CF_2$—, —O—, —S(O)$_m$, 1,3-dioxolane, $C_{1-7}$ alkyl-OH, where alkyl, alkylene or arylene may be unsubstituted or substituted with one or more halogens, OH, —O—$C_1$-$C_6$alkyl, —S—$C_1$-$C_6$alkyl or —$CF_3$ wherein m is 0, 1, or 2; or (b) —N($R_{15}$) wherein $R_{15}$ is H, $C_{1-7}$ alkyl (unsubstituted or substituted), aryl, het, —O($C_{1-7}$cycloalkyl) (unsubstituted or substituted), 0($C_{1-7}$alkyl) (unsubstituted or substituted), C(O)—$C_1$-$C_{10}$alkyl, C(O)—$C_o$—$C_{10}$alkyl-aryl, C(O)$C_1$-$C_{10}$alkyl, C—(O)—$C_o$—$C_{10}$alkyl-het, $SO_2$—$C_1$-$C_{10}$-alkyl, $SO_2$—($C_o$—$C_{10}$-alkylaryl), or $SO_2$—($C_o$—$C_{10}$-alkylhet);

Each Y is independently H, F, $C_1$-$C_{10}$ alkyl, $C_1$-$C_{10}$ alkoxy, aryl $C_1$-$C_{10}$ alkoxy, het $C_1$-$C_{10}$ alkoxy, OH, O—$C_1$-$C_{10}$-alkyl, $(CH_2)_{0-6}$—$C_3$-$C_7$ cycloalkyl, aryl, het, aryl $C_1$-$C_{10}$ alkyl, het $C_1$-$C_{10}$ alkyl, O—$(CH_2)_{0-6}$ aryl, $(CH_2)_{1-6}$ aryl, $(CH_2)_{1-6}$het, O—$(CH_2)_{0-6}$het, —$OR_{11}$, $C(O)R_{11}$, —C(O)N($R_{11}$)($R_{12}$), N($R_{11}$)($R_{12}$), $SR_{11}$, $S(O)R_{11}$, $S(O)_2R_{11}$, $S(O)_2$—N($R_{11}$)($R_{12}$), or $NR_{11}$—$S(O)_2$—($R_{12}$), wherein alkyl, cycloalkyl aryl, het are unsubstituted or substituted; and each p is independently 0, 1, 2, 3, 4, 5, 6, 7, 8, 9 or 10;

Q together with $R_4$, $R_6$ or Y may form a ring;

X is H, aryl, cycloalkyl, het, or an 8-12 membered fused ring system that may include an aromatic ring, or one 5-7 het containing 1, 2, or 3 heteroring atoms selected from N, O and S, in which any may substituted or unsubstituted, in which substituents on aryl, cycloalkyl and het are alkyl, halo, lower alkoxy, N($R_5$)$R_6$, CN, $NO_2$, O Q together with $R_4$, $R_6$ or Y may form a ring $R_5$, $S(O)_yR_5$, $C(O)N(R_5)R_6$, $S(O)_yN(R_5)R_6$; N($R_5$)C(O)$R_6$, or N($R_5$)S(O)$_y$$R_6$, wherein y is 0, 1, or 2;

het is a 5-7 membered monocyclic heterocyclic ring (aromatic or non-aromatic) containing 1-4 heteroring atoms selected from N, O, and S; or an 8-12 membered fused ring system that includes one 5-7 membered heterocyclic ring (aromatic or non-aromatic) containing 1, 2, or 3 heteroring atoms selected from N, O and S, which het is unsubstituted or substituted;

$R_{11}$ and $R_{12}$ are independently H, $C_1$-$C_{10}$ alkyl, $(CH_2)_{0-6}$—$C_3$-$C_7$cycloalkyl, $(CH_2)_{0-6}$—$(CH)_{0-1}$(aryl)$_{1-2}$, C(O)—$C_1$-$C_{10}$alkyl, —C(O)—$(CH_2)_{1-6}$—$C_3$-$C_7$cycloalkyl, —C(O)—O—$(CH_2)_{0-6}$-aryl, —C(O)—$(CH_2)_{0-6}$—O-fluorenyl, C(O)—NH—$(CH_2)_{0-6}$-aryl, C(O)—$(CH_2)_{0-6}$-aryl, C(O)—$(CH_2)_{1-6}$-het, —C(S)—$C_1$-$C_{10}$alkyl, —C(S)—$(CH_2)_{1-6}$—$C_3$-$C_7$cycloalkyl, —C(S)—O—$(CH_2)_{0-6}$-aryl, —C(S)—$(CH_2)_{0-6}$—O-fluorenyl, C(S)—NH—$(CH_2)_{0-6}$-aryl, —C(S)—$(CH_2)_{0-6}$-aryl, C(S)—$(CH_2)_{1-6}$-het, $C(O)R_{11}$, C(O)NR$_{11}$R$_{12}$, C(O)OR$_{11}$, S(O)$_m$, R$_{11}$, S(O)$_m$NR$_{11}$R$_{12}$, C(S)R$_{11}$, C(S)NR$_{11}$R$_{12}$, or C(S)OR$_{11}$, and m=0, 1 or 2, wherein alkyl, cycloalkyl and aryl are unsubstituted or substituted; or $R_{11}$ and $R_{12}$ are a substituent that facilitates transport of the molecule across a cell membrane; or $R_{11}$ and $R_{12}$ together with the nitrogen atom form het; wherein the alkyl substituents of $R_{11}$ and $R_{12}$ may be unsubstituted or substituted by one or more substituents selected from $C_1$-$C_{10}$alkyl, halogen, OH, O—$C_1$-$C_6$alkyl, —S—$C_1$-$C_6$alkyl, $CF_3$ or $NR_{11}R_{12}$; and substituted cycloalkyl substituents of $R_{11}$ and $R_{12}$ are substituted by one or more substituents selected from a $C_2$-$C_{10}$ alkene, $C_1$-$C_6$alkyl, halogen, OH, O—$C_1$-$C_6$alkyl, S—$C_1$-$C_6$alkyl, $CF_3$, or $NR_{11}R_{12}$; and substituted het or substituted aryl of $R_{11}$ and $R_{12}$ are substituted by one or more substituents selected from halogen, hydroxy, $C_1$-$C_4$ alkyl, $C_1$-$C_4$ alkoxy, nitro, CN, O—C(O)—$C_1$-$C_4$alkyl, or C(O)—O—$C_1$-$C_4$-alkyl;

wherein the substituents on $R_1$, $R_2$, $R_3$, $R_4$, $R_5$, $R_6$, $R_7$, Q, A, and X groups are independently halo, hydroxy, lower alkyl, lower alkenyl, lower alkynyl, lower alkanoyl, lower alkoxy, aryl, aryl lower alkyl, amino, amino lower alkyl, diloweralkylamino, lower alkanoyl, amino lower alkoxy, nitro, cyano, cyano lower alkyl, carboxy, lower carbalkoxy, lower alkanoyl, aryloyl, lower arylalkanoyl, carbamoyl, N-mono- or N,N-dilower alkyl carbamoyl, lower alkyl carbamic acid ester, amidino, guanidine, ureido, mercapto, sulfo, lower alkylthio, sulfoamino, sulfonamide, benzosulfonamide, sulfonate, sulfanyl lower alkyl, aryl sulfonamide, halogen substituted aryl sulfonate, lower alkylsulfinyl, arylsulfinyl; aryl-lower alkylsulfinyl, lower alkylarylsulfinyl, lower alkyl-sulfonyl, arylsulfonyl, aryl-lower alkylsulfonyl, lower alkylarylsulfinyl, lower alkyl-sulfonyl, arylsulfonyl, aryl-lower alkylsulfonyl, lower aryl alkyl lower alkylarylsulfonyl, halogen-lower alkylmercapto, halogen-lower alkylsulfonyl, phosphono (—P(═O)(OH)$_2$), hydroxy-lower alkoxy phosphoryl or di-lower alkoxyphosphoryl, ($R_9$)NC(O)—$NR_{10}R_{13}$, lower alkyl carbamic acid ester or carbamates or —$NR_8R_{14}$, wherein $R_8$ and $R_{14}$ can be the same or different and are independently H or lower alkyl, or $R_8$ and $R_{14}$ together with the N atom form a 3- to 8-membered heterocyclic ring containing a nitrogen heteroring atoms and may optionally contain one or two additional heteroring atoms selected from nitrogen, oxygen and sulfur, which heterocyclic ring may be unsubstituted or substituted with lower alkyl, halo, lower alkenyl, lower alkynyl, hydroxy, lower alkoxy, nitro, amino, lower alkyl, amino, diloweralkyl amino, cyano, carboxy, lower carbalkoxy, formyl, lower alkanoyl, oxo, carbamoyl, N-lower or N,N-dilower alkyl carbamoyl, mercapto, or lower alkylthio, and $R_9$, $R_{10}$, and $R_{13}$ are independently hydrogen, lower alkyl, halogen substituted lower alkyl, aryl, aryl lower alkyl, halogen substituted aryl, halogen substituted aryl lower alkyl.

The present invention also relates to pharmaceutical compositions comprising therapeutically effective amounts of compounds of Formula I, as defined hereinabove, or a pharmaceutically acceptable salt thereof, and a pharmaceutical carrier therefor. In another embodiment, the present invention is directed to a method of treating a mammal, especially human, afflicted with a proliferative disease, especially those dependent on the binding of the smac protein to Inhibitor of Apoptosis Proteins (IAPs), such as cancer, which method comprises administering to said mammal in need of treatment an anti-proliferative effective amount of a compound of Formula I or a pharmaceutically acceptable salt thereof. The present invention is also directed to the manufacture of compounds of Formula I for use in the treatment of said diseases.

DETAILED DESCRIPTION

In an embodiment, the present invention relates to compounds according to formula I wherein $R_1$ is H, or $C_1$-$C_4$ alkyl, which $R_1$ may be unsubstituted or substituted; $R_2$ is H, or $C_1$-$C_4$ alkyl, which $R_2$ may be unsubstituted or substituted; $R_1$ and $R_2$ may be taken together to form a ring or het; $R_3$ and $R_3$' are independently H, $CF_3$, $C_2F_5$, $C_1$-$C_4$ alkyl, $C_2$-$C_4$ alkenyl, $C_2$-$C_4$ alkynyl, $CH_2$—Z, or $R_2$ and $R_3$ taken together with the nitrogen atom to which they are attached form het, wherein alkyl, alkenyl, alkynyl or het may be unsubstituted or substituted; and Z is H, OH, F, Cl, $CH_3$, $CH_2Cl$, $CH_2F$ or $CH_2OH$. Each Q is independently H, F, Cl, Br, I, $C_1$-$C_{10}$ alkyl, $(CH_2)_{0-6}$—$C_3$-$C_7$ cycloalkyl, aryl, het, wherein alkyl, cycloalkyl, aryl and het are unsubstituted or substituted, n is 0, 1, or 2, and independent Q's may be joined to form a 5-10 membered ring. M is C($R_4$)($R_5$), C(O), C(S), or a bond; and U is $CON(R_6)(R_7)$, $CN(R_6)(R_7)$, $SO_mN(R_6)(R_7)$, $R_4$, $C(R_4)(R_5)O(R_6)$, $C(R_4)(R_5)$, or $C(R_4)(R_5)N(R_6)(R_7)$.

In a further embodiment, the present invention relates to compounds according to formula I wherein $R_1$ is H, or $C_1$-$C_4$ alkyl, which $R_1$ may be unsubstituted or substituted; $R_2$ is H, or $C_1$-$C_4$ alkyl, which $R_2$ may be unsubstituted or substituted. $R_3$ and $R_3'$ are independently H, or $C_1$-$C_4$ alkyl; Q is aryl which is unsubstituted or substituted; M is $C_1$-$C_4$ alkyl, C(O), or a bond; and U is $C(O)N(R_6)(R_7)$, or $CN(R_6)(R_7)$, wherein $R_6$ and $R_7$ independently are aryl, or cycloalkyl-het, and aryl or cycloalkyl-het may be unsubstituted or substituted.

In an embodiment, the present invention relates to compounds according to formula I wherein $R_1$ is H, or $C_1$-$C_4$ alkyl, which $R_1$ may be unsubstituted or substituted; $R_2$ is H, or $C_1$-$C_4$ alkyl, which $R_2$ may be unsubstituted or substituted; $R_3$ and $R_3'$ are independently H, or $C_1$-$C_4$ alkyl; Q is benzene, or fluorobenzene; M is $C_1$-$C_4$ alkyl, C(O), or a bond; and U is $C(O)N(R_6)(R_7)$, or $CN(R_6)(R_7)$, wherein $R_6$ and $R_7$ independently are tetrahydro-napthalene (tetralin), or fluorobenzene.

In another embodiment, the present invention relates to compounds according to formula I wherein: $R_1$ is H, or $C_1$-$C_4$ alkyl, which $R_1$ may be unsubstituted or substituted; $R_2$ is H, or $C_1$-$C_4$ alkyl, which $R_2$ may be unsubstituted or substituted; $R_3$ and $R_3'$ are independently H, or $C_1$-$C_4$ alkyl; Q is aryl which may be unsubstituted or substituted. M is $C_1$-$C_4$ alkyl, C(O), or a bond; and U is aryl-V-aryl, het-V-aryl, or aryl-V-het, wherein V is C(O), $N(R_{15})$, het, O, or a bond. In an embodiment, Q is benzene or fluorobenzene, and the het group of U is pyridine or thiazole; and the aryl group of U is fluorobenzene, benzene, or benzene fused with dioxolane. In another embodiment, the het group of U is a five membered ring with N as the heterocyclic atom, and may be aromatic or non-aromatic.

In another embodiment, the present invention relates to a pharmaceutical composition comprising a therapeutically effective amount of a compound of formula I. The pharmaceutical composition may also include a pharmaceutically acceptable carrier. In a further embodiment, the present invention also provides a method of treating a mammal suffering from a proliferative disease. The method includes administering to the mammal in need of treatment a therapeutically effective amount of a compound according to formula I. In a further embodiment, the present invention includes a method of inhibiting cell proliferation. The method includes administering an effective amount of the compound according to formula I to inhibit cell proliferation to a cell or mammal in need thereof.

As used herein, the term "Aryl" is defined as an aromatic radical having 6 to 14 ring carbon atoms, and no ring heteroatoms. The aryl group may be monocyclic or fused bicyclic or tricyclic. It may be unsubstituted or substituted by one or more, preferably one or two, substituents, wherein the substituents are as described herein. As defined herein, the aryl moiety may be completely aromatic regardless of whether it is monocyclic or bicyclic. However, if it contains more than one ring, as defined herein, the term aryl includes moieties wherein at least one ring is completely aromatic while the other ring(s) may be partially unsaturated or saturated or completely aromatic "Het" as used herein, refers to heteroaryl and heterocyclic compounds containing at least one S, O or N ring heteroatom. More specifically, "Het" is a 5-7 membered heterocyclic ring containing 1-4 heteroatoms selected from N, O and S, or an 8-12 membered fused ring system including at least one 5-7 membered heterocyclic ring containing 1, 2 or 3 heteroatoms selected from N, O, and S. Examples of het, as used herein, include but are not limited to unsubstituted and substituted pyrrolidyl, tetrahydrofuryl, tetrahydrothiofuryl, piperidyl, piperazyl, purinyl, tetrahydropyranyl, morpholino, 1,3-diazapanyl, 1,4-diazapanyl, 1,4-oxazepanyl, 1,4-oxathiapanyl, furyl, thienyl, pyrryl, pyrrolyl, pyrazolyl, triazolyl, tetrazolyl, indazolyl, oxadiazolyl, imidazolyl, pyrrolidyl, pyrrolidinyl, thiazolyl, oxazolyl, pyridyl, pyrazolyl, pyrazinyl, pyrimidinyl, isoxazolyl, pyrazinyl, quinolyl, isoquinolyl, pyridopyrazinyl, pyrrolopyridyl, furopyridyl, indolyl, benzofuryl, benzothiofuryl, benzoindolyl, benzothienyl, pyrazolyl, piperidyl, piperazinyl, indolinyl, morpholinyl, benzoxazolyl, pyrroloquinolyl, pyrrolo[2,3-b]pyridinyl, benzotriazolyl, oxobenzo-oxazolyl, benco[1,3]dioxolyl, benxzoimidazolyl, quinolinyl, indanyl and the like. Heteroaryls are within the scope of the definition of het. Examples of heteroaryls are pyridyl, pyrimidinyl, quinolyl, thiazolyl and benzothiazolyl. The most preferred het are pyridyl, pyrimidinyl and thiazolyl. The het may be unsubstituted or substituted as described herein. It is preferred that it is unsubstituted or if substituted it is substituted on a carbon atom by halogen, especially fluorine or chlorine, hydroxy, $C_1$-$C_4$ alkyl, such as methyl and ethyl, $C_1$-$C_4$ alkoxy, especially methoxy and ethoxy, nitro, —O—C(O)—$C_1$-$C_4$alkyl or —C(O)—O—$C_1$-$C_4$alkyl, SCN or nitro or on a nitrogen atom by $C_1$-$C_4$ alkyl, especially methyl or ethyl, —O—C(O)—$C_1$-$C_4$alkyl or —C(O)—O—$C_1$-$C_4$alkyl, such as carbomethoxy or carboethoxy.

When two substituents together with a commonly bound nitrogen are het, it is understood that the resulting heterocyclic ring is a nitrogen-containing ring, such as aziridine, azetidine, azole, piperidine, piperazine, morphiline, pyrrole, pyrazole, thiazole, oxazole, pyridine, pyrimidine, isoxazole, and the like, wherein such het may be unsubstituted or substituted as defined hereinabove.

Halogen is fluorine, chlorine, bromine or iodine, especially fluorine and chlorine.

Unless otherwise specified "alkyl", either above or in combination, includes straight or branched chain alkyl, such as methyl, ethyl, n-propyl, isopropyl, n-butyl, sec-butyl, tert-butyl, n-pentyl and branched pentyl, n-hexyl and branched hexyl, and the like.

A "cycloalkyl" group means $C_3$ to $C_{10}$ cycloalkyl having 3 to 10 ring carbon atoms and may be, for example, cyclopropyl, cyclobutyl, cyclopentyl, cyclohexyl, cycloheptyl or cyclooctyl, cyclononyl and the like. The cycloalkyl group may be monocyclic or fused bicyclic. Moreover, the preferred cycloalkyl group is cyclopentyl or cyclohexyl. Most preferably, cycloalkyl is cyclohexyl. The cycloalkyl group may be fully saturated or partially unsaturated, although it is preferred that it is fully saturated. As defined herein, it excludes aryl groups. The cycloalkyl groups may be unsubstituted or substituted with any of the substituents defined below, preferably halo, hydroxy or $C_1$-$C_6$ alkyl such as methyl.

Substituents that facilitate transport of the molecule across a cell membrane are known to those of skill in the medicinal chemistry arts (see, for example, Gangewar S., Pauletti G. M., Wang B., Siahaan T. J., Stella V. J., Borchardt R. T., *Drug Discovery Today*, vol. 2. p 148-155 (1997) and Bundgaard H. and Moss J., *Pharmaceutical Research*, vol. 7, p 885 (1990)). Generally, such substituents are lipophillic substituents. Such lipophillic substituents include a $C_6$-$C_{30}$ alkyl which is saturated, monounsaturated, polyunsaturated, including methylene-interrupted polyene, phenyl, phenyl which is substituted by one or two $C_1$-$C_8$ alkyl groups, $C_5$-$C_9$ cycloalkyl, $C_5$-$C_9$ cycloalkyl which is substituted by one or two $C_1$-$C_8$ alkyl groups, —$X_1$-phenyl, —$X_1$-phenyl which is substituted in the phenyl ring by one or two $C_1$-$C_8$ alkyl groups, $X_1$—$C_5$-$C_9$ cycloalkyl or $X_1$—$C_5$-$C_9$ cycloalkyl which is substituted by one or two $C_1$-$C_8$ alkyl groups; where $X_1$ is $C_1$-$C_{24}$ alkyl which is saturated, monounsaturated or polyunsaturated and straight or branched chain.

Unsubstituted is intended to mean that hydrogen is the only substituent.

Except as described herein, any of the above defined aryl, het, alkyl, alkenyl, alkynyl, or cycloalkyl, may be unsubstituted or independently substituted by up to four, preferably one, two or three substituents, selected from the group consisting of: halo (such as Cl or Br); hydroxy; lower alkyl (such as $C_1$-$C_3$ alkyl); lower alkyl which may be substituted with any of the substituents defined herein; lower alkenyl; lower alkynyl; lower alkanoyl; lower alkoxy (such as methoxy); aryl (such as phenyl or naphthyl); substituted aryl (such as fluoro phenyl or methoxy phenyl); aryl lower alkyl such as benzyl, amino, mono or di-lower alkyl (such as dimethylamino); lower alkanoyl amino acetylamino; amino lower alkoxy (such as ethoxyamine); nitro; cyano; cyano lower alkyl; carboxy; lower carbalkoxy (such as methoxy carbonyl; n-propoxy carbonyl or iso-propoxy carbonyl), lower aryloyl, such as benzoyl; carbamoyl; N-mono- or N,N di-lower alkyl carbamoyl; lower alkyl carbamic acid ester; amidino; guanidine; ureido; mercapto; sulfo; lower alkylthio; sulfoamino; sulfonamide; benzosulfonamide; sulfonate; sulfanyl lower alkyl (such as methyl sulfanyl); sulfoamino; aryl sulfonamide; halogen substituted or unsubstituted aryl sulfonate (such as chloro-phenyl sulfonate); lower alkylsulfinyl; arylsulfinyl; aryl-lower alkylsulfinyl; lower alkylarylsulfinyl; lower alkanesulfonyl; arylsulfonyl; aryl-lower alkylsulfonyl; lower aryl alkyl; lower alkylarylsulfonyl; halogen-lower alkylmercapto; halogen-lower alkylsulfonyl; such as trifluoromethane sulfonyl; phosphono(—P(=O)(OH)$_2$); hydroxy-lower alkoxy phosphoryl or di-lower alkoxy-phosphoryl; urea and substituted urea; alkyl carbamic acid ester or carbamates (such as ethyl-N-phenyl-carbamate); or lower alkyl (e.g. methyl, ethyl or propyl).

In an embodiment, the above mentioned alkyl, cycloalkyl, and aryl groups are independently unsubstituted or are substituted by lower alkyl, aryl, aryl lower alkyl, carboxy, lower carbalkoxy and especially halogen, —OH, —SH, —OCH$_3$, —SCH$_3$, —CN, —SCN or nitro.

As defined herein the term "lower alkyl", when used alone or in combination refers to alkyl containing 1-6 carbon atoms. The alkyl group may be branched or straight-chained, and is as defined hereinabove.

The term "lower alkenyl" refers to a alkenyl group which contains 2-6 carbon atoms. An alkenyl group is a hydrocarbyl group containing at least one carbon-carbon double bond. As defined herein, it may be unsubstituted or substituted with the substituents described herein. The carbon-carbon double bonds may be between any two carbon atoms of the alkenyl group. It is preferred that it contains 1 or 2 carbon-carbon double bonds and more preferably one carbon-carbon double bond. The alkenyl group may be straight chained or branched. Examples include but are not limited to ethenyl, 1-propenyl, 2-propenyl, 1-butenyl, 2-butenyl, 2-methyl-1-propenyl, 1,3-butadienyl, and the like.

The term "lower alkynyl", as used herein, refers to an alkynyl group containing 2-6 carbon atoms. An alkynyl group is a hydrocarbyl group containing at least one carbon-carbon triple bond. The carbon-carbon triple bond may be between any two carbon atom of the alkynyl group. In an embodiment, the alkynyl group contains 1 or 2 carbon-carbon triple bonds and more preferably one carbon-carbon triple bond. The alkynyl group may be straight chained or branched. Examples include but are not limited to ethynyl, 1-propynyl, 2-propynyl, 1-butynyl, 2-butynyl and the like.

As used herein, the term "aryl alkyl" refers to a aryl group connected to the main chain by a bridging alkylene group. Examples include but are not limited to benzyl, phenethyl, naphthylmethyl, and the like. Similarly, cyano alkyl group refers to a cyano group connected to the main chain by a bridging alkylene group.

The term "alkyl aryl" on the other hand, refers to an alkyl group bridged to the main chain through a phenylene group. Examples include but are not limited to methylphenyl, ethylphenyl, and the like.

As used herein, the term lower alkanoyl refers to a lower alkyl chain in which one of the carbon atoms is replaced by a C=O group. The C=O group may be present at one of the ends of the substituent or in the middle of the moiety. Examples include but are not limited to formyl, acetyl, 2-propanoyl, 1-propanoyl and the like.

The term "alkoxy" refers to an alkyl group as defined herein, connected to the main chain by an oxygen atom. Examples include but are not limited to methoxy, ethoxy, and the like.

The term "lower thioalkyl" refers to an alkyl group, as defined herein, connected to the main chain by a sulfur atom. Examples include but are not limited to thiomethyl (or mercapto methyl), thioethyl (mercapto ethyl) and the like.

The term "lower carbalkoxy" or synonym thereto refers to an alkoxycarbonyl group, where the attachment to the main chain is through the aryl group (C(O)). Examples include but are not limited to methoxy carbonyl, ethoxy carbonyl, and the like.

It is to be understood that the terminology C(O) refers to a —C=O group, whether it be ketone, aldehyde or acid or acid derivative. Similarly, —S(O) refers to a —S=O group.

As discussed above, the compounds of the present invention are useful for treating proliferative diseases. Thus, the present invention further relates to a method of treating a proliferative disease which comprises administering a therapeutically effective amount of a compound of the invention to a mammal, preferably a human, in need of such treatment.

A proliferative disease is mainly a tumor disease (or cancer) (and/or any metastases). The inventive compounds are particularly useful for treating a tumor which is a breast cancer, genitourinary cancer, lung cancer, gastrointestinal cancer, epidermoid cancer, melanoma, ovarian cancer, pancreas cancer, neuroblastoma, head and/or neck cancer or bladder cancer, or in a broader sense renal, brain or gastric cancer; in particular (i) a breast tumor; an epidermoid tumor, such as an epidermoid head and/or neck tumor or a mouth tumor; a lung tumor, for example a small cell or non-small cell lung tumor; a gastrointestinal tumor, for example, a colorectal tumor; or a genitourinary tumor, for example, a prostate tumor (especially a hormone-refractory prostate tumor); or (ii) a proliferative disease that is refractory to the treatment with other chemotherapeutics; or (iii) a tumor that is refractory to treatment with other chemotherapeutics due to multidrug resistance.

In a broader sense of the invention, a proliferative disease may furthermore be a hyperproliferative condition such as leukemias, hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

Where a tumor, a tumor disease, a carcinoma or a cancer are mentioned, also metastasis in the original organ or tissue and/or in any other location are implied alternatively or in addition, whatever the location of the tumor and/or metastasis.

The inventive compound is selectively toxic or more toxic to rapidly proliferating cells than to normal cells, particularly in human cancer cells, e.g., cancerous tumors, the compound has significant antiproliferative effects and promotes differentiation, e.g., cell cycle arrest and apoptosis.

The present invention further relates to a method of promoting apoptosis in rapidly proliferating cells, which comprises contacting the rapidly proliferating cells with an effective apoptosis promoting amount of a non-naturally-occurring compound that binds to the Smac binding site of XIAP and/or cIAP proteins. Preferably, the non-naturally-occurring compound is a compound of present formula I.

The invention relates also to pharmaceutical compositions comprising a compound of formula I, to their use in the therapeutic (in a broader aspect of the invention also prophylactic) treatment or a method of treatment of a kinase dependent disease, especially the preferred diseases mentioned above, to the compounds for said use and to pharmaceutical preparations and their manufacture, especially for said uses.

The present invention also relates to pro-drugs of a compound of formula I that convert in vivo to the compound of formula I as such. Any reference to a compound of formula I is therefore to be understood as referring also to the corresponding pro-drugs of the compound of formula I, as appropriate and expedient.

The pharmacologically acceptable compounds of the present invention may be present in or employed, for example, for the preparation of pharmaceutical compositions that comprise an effective amount of a compound of the formula I, or a pharmaceutically acceptable salt thereof, as active ingredient together or in admixture with one or more inorganic or organic, solid or liquid, pharmaceutically acceptable carriers (carrier materials)

The invention relates also to a pharmaceutical composition that is suitable for administration to a warm-blooded animal, especially a human (or to cells or cell lines derived from a warm-blooded animal, especially a human, e.g. lymphocytes), for the treatment of (this, in a broader aspect of the invention, also includes the prevention of (=prophylaxis against)) a disease that responds to inhibition of protein kinase activity, comprising an amount of a compound of formula I or a pharmaceutically acceptable salt thereof, preferably which is effective for said inhibition, together with at least one pharmaceutically acceptable carrier.

The pharmaceutical compositions according to the invention are those for enteral, such as nasal, rectal or oral, or parenteral, such as intramuscular or intravenous, administration to warm-blooded animals (especially a human), that comprise an effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration.

The invention relates also to a method of treatment for a disease that responds to inhibition of a protein kinase and/or a proliferative disease, which comprises administering a (against the mentioned diseases) prophylactically or especially therapeutically effective amount of a compound of formula I according to the invention, or a tautomer thereof or a pharmaceutically acceptable salt thereof, especially to a warm-blooded animal, for example a human, that, on account of one of the mentioned diseases, requires such treatment.

The dose of a compound of the formula I or a pharmaceutically acceptable salt thereof to be administered to warm-blooded animals, for example humans of approximately 70 kg body weight, preferably is from approximately 3 mg to approximately 10 g, more preferably from approximately 10 mg to approximately 1.5 g, most preferably from about 100 mg to about 1000 mg/person/day, divided preferably into 1-3 single doses which may, for example, be of the same size. Usually, children receive half of the adult dose.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilizing, mixing, granulating or confectioning processes.

The compounds of the present invention are prepared as depicted below in scheme 1. For example, compounds of formula (I) are prepared by reacting a carboxylic acid or acylating derivative thereof, such as an acid halide of formula (II) with an amine of formula (III) under amide forming conditions:

Scheme 1

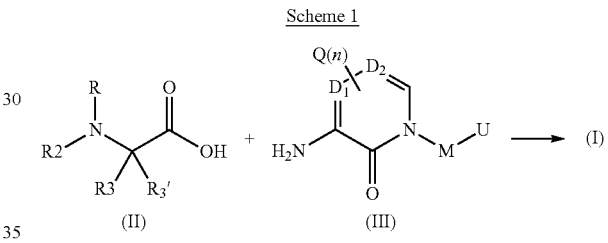

wherein R is a protecting group or $R_1$; $R_1$, $R_2$, $R_3$, $R_3'$, Q, n, $D_1$, $D_2$, M and U are as defined hereinabove.

The compound of formula (II) is either commercially-available or is prepared from formula (IV):

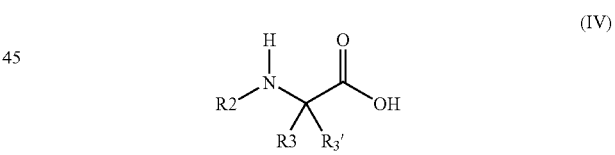

in which the amino group is reacted with an amino protecting group under conditions known to one of ordinary skill in the art. The compound of formula (III) is either commercially-available or prepared by art recognized techniques or may be prepared as depicted below in scheme 2.

Scheme 2

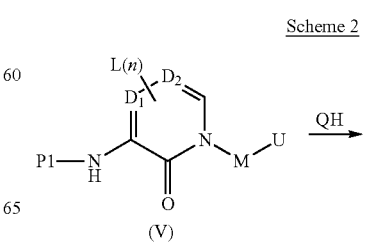

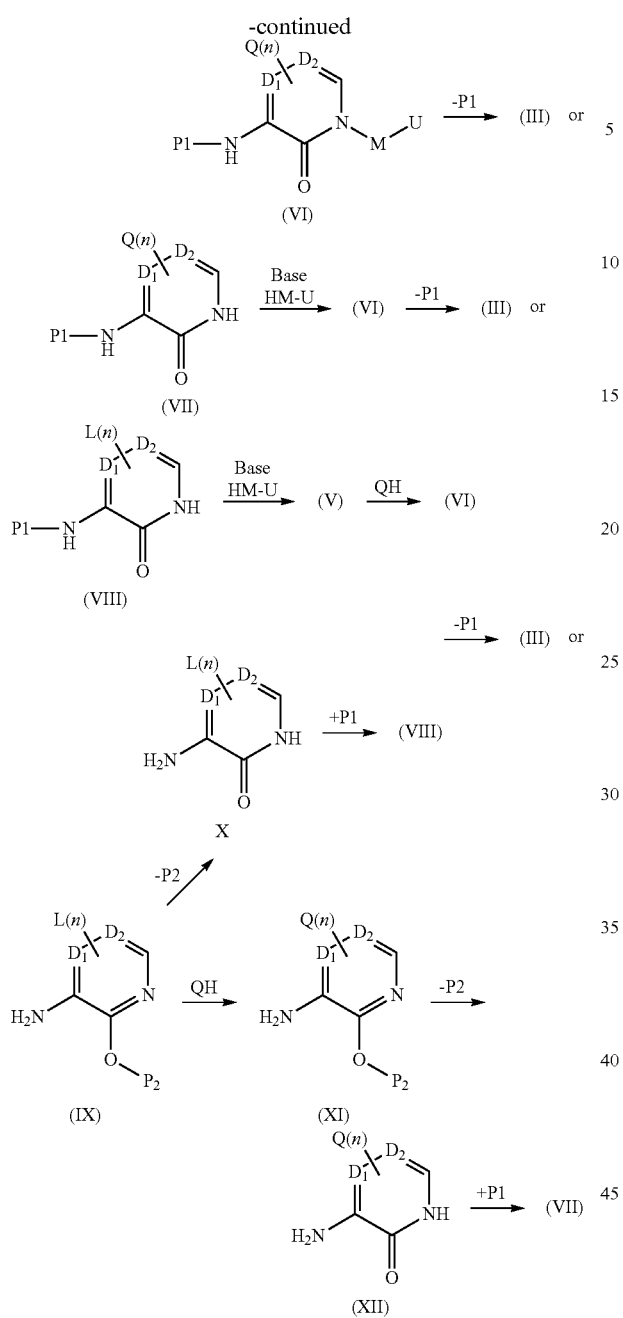

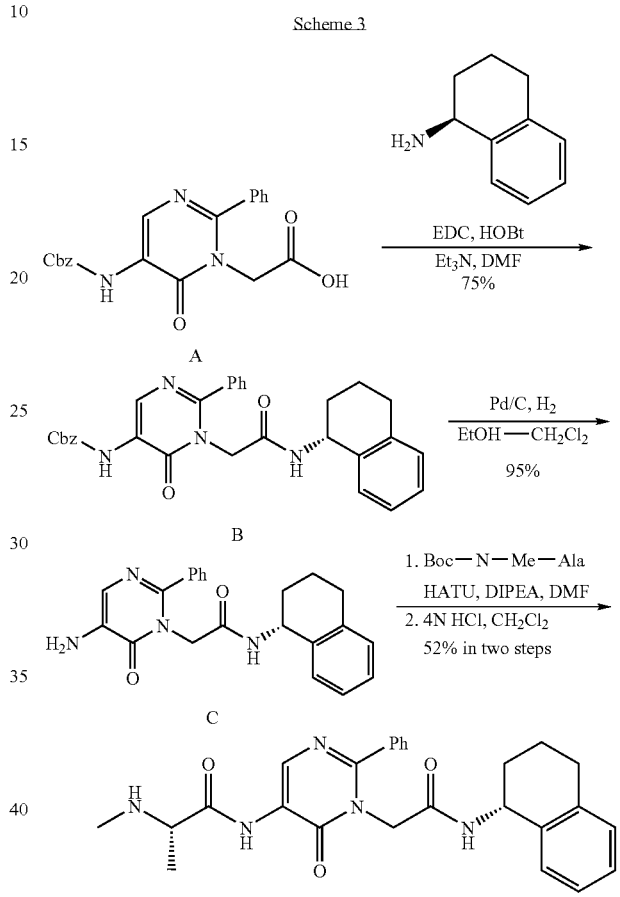

wherein formulae (V), (VII), (VIII) and (IX) are either commercially available or prepared by art recognized techniques or as the scheme above shown, is a leaving group; P1 and P2 are protecting groups.

If any group on the reactants is reactive under the conditions described it is protected by a protecting group known in the art, prior to conducting the reactions described hereinabove and then removed after the reaction is effected. Protecting groups normally used in these reactions are described in a book entitled *Protective Groups in Organic Synthesis*, Theodora W. Greene, John Wiley & Sons, NY, N.Y. (1981), the contents of which are incorporated by reference.

EXAMPLES

The following examples are intended to illustrate, but not further limit, the invention. The following compounds are prepared by methods analog to those described herein utilizing analogous starting materials:

5 (2 methylamino-propionamidyl)-6-oxo-2-phenyl-1,6-dihydro-1-pyrimidinyl-N-tetrahedron-naphthoyl)-acetamide (example 29 of table 2). The synthesis of the title compound (example 29) is carried out according to the procedures set forth in scheme 3 below:

Scheme 3

[5-[(Benzyloxycarbonyl)amino]-6-oxo-2-(phenyl)-1,6-dihydro-1-pyrimidinyl]-N-tetrahedro-naphthoyl) acetamide (B)

To a solution of the acid A (Veale, C. A. et. al. *J. Med. Chem.* 1995, 38, 98-108) (379 mg, 1 mmol), 1-hydroxybenzotriazole hydrate (203 mg, 1.5 mmol), and triethylamine (202 mg, 2 mmol) in DMF (5 mL) was added EDC (356 mg, 1.2 mmol), and the solution was stirred for 0.5 h. (R)-(1,2,3, 4-Tetrahydro-naphthalen-1-yl)amine (147 mg, 1 mmol) was added, and the solution was stirred for 16 h. Then the solution was diluted with $H_2O$ and extracted with ethyl acetate, washed with a saturated aqueous solution of ammonium chloride (2×25 mL). The solution was dried and the solvent removed. The resulting oil crystallized upon standing and was collected and dried to give the titled amide B (383 mg, 75%) as a white solid: $^1H$ NMR (400 MHz, $CDCl_3$): δ 8.75 (1H, s), 7.62 (2H, m), 7.51 (4H, m), 7.37 (5H, m), 7.16 (4H, m), 6.08 (1H, d), 5.22 (2H, s), 5.20 (1H, m), 4.56 (2H, s), 2.74 (2H, t), 1.78 (4H, m); MS: 509 ($M+H^+$).

5-aminol-6-oxo-2-phenyl-1,6-dihydro-1-pyrimidinyl-N-tetrahedron-naphthoyl)-acetamide (C)

Compound B (383 mg, 0.755 mmol) was dissolved in ethanol (5 mL) and to this solution was added 10% Pd/C (10 mg). The suspension was shaken under a hydrogen atmosphere (45 psi) for 4 hrs. The mixture was filtered free of catalyst and the solvent removed, yielding product 11 (268 mg, 95%) as an off-white solid: $^1$H NMR (400 MHz, CDCl$_3$): δ 7.58 (2H, m), 7.48 (4H, m), 7.23 (1H, m), 7.19 (2H, m), 7.11 (1H, m), 6.08 (1H, d), 5.20 (1H, m), 4.56 (2H, s), 4.03 (2H, s), 2.78 (2H, m), 2.08 (1H, m), 1.82 (3H, m); MS: 375 (M+H$^+$).

5-(2-methylamino-propionamidyl)-6-oxo-2-phenyl-1,6-dihydro-1-pyrimidinyl-N-tetrahedron-naphthoyl)-acetamide (Example No. 29)

To a solution of the (S)-Boc-N-Me-Ala (65 mg, 0.32 mmol) in DMF (2.5 mL) was added HATU (150 mg, 0.38 mmol), and DIPEA (82 mg, 0.64 mmol), and the solution was stirred for 0.5 h. Then amine C (100 mg, 0.267 mmol) was added, and the solution was stirred for 16 h. Then the solution was diluted with H$_2$O and extracted with ethyl acetate (3×50 mL), then washed with a saturated aqueous solution of ammonium chloride (2×20 mL). The solution was dried and the solvent removed. The resulting oil was carried over to next step. The crude product was dissolved in dichloromethane (3 mL). To this solution was added 4N HCl in dioxane (2 mL). The reaction mixture was stirred for 10 h; then solvent was removed, and the resulting oil was purified by preparative HPLC to give the tiled product, example no. 29 (96 mg, 52% in two steps) as a TFA salt and as a white solid: $^1$H NMR (400 MHz, MeOD): δ 8.87 (1H, s), 8.51 (1H, d), 7.48 (5H, m), 7.04 (4H, m), 5.01 (1H, m), 4.57 (2H, m), 4.20 (1H, q), 2.72 (5H, m), 1.85 (4H, m), 1.65 (3H, d); MS: 460 (M+H$^+$).

(S)-2-Methylamino-N-(3-oxo-5-phenyl-4-{[(R)-(1,2,3,4-tetrahydro-naphthalen-1-yl)carbamoyl]-methyl}-3,4-dihydro-pyrazin-2-yl)-propionamide (example no. 30). The synthesis of the title compound (example 30) is carried out according to the procedures set forth in scheme 4 below:

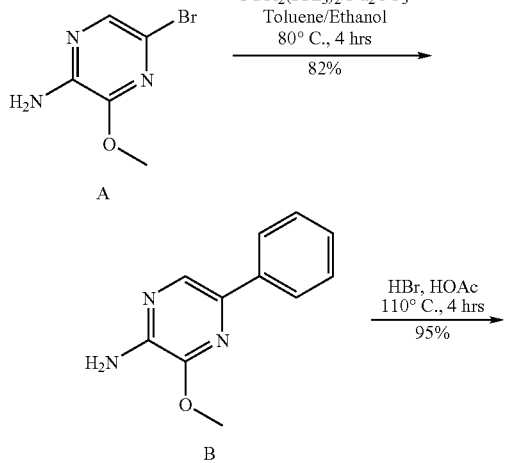

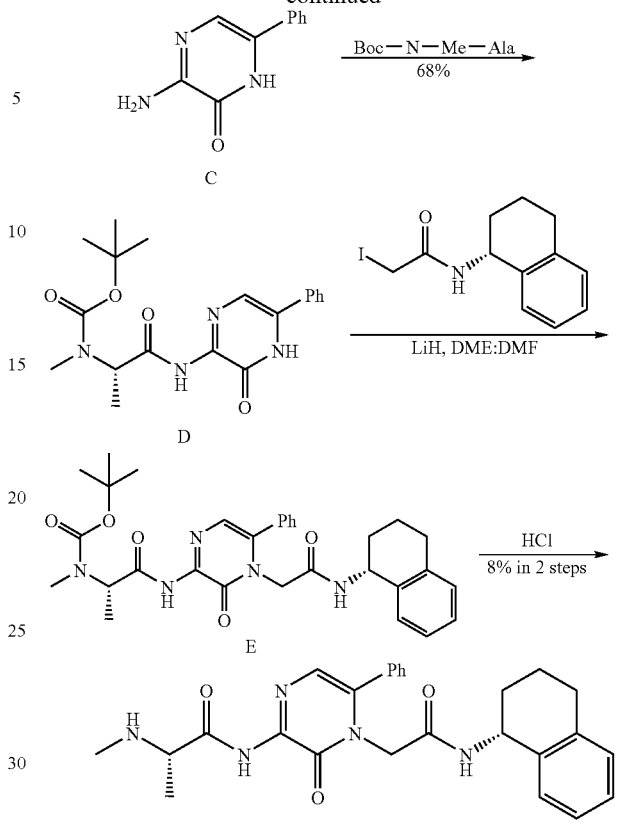

3-Methoxy-5-phenyl-pyrazin-2-ylamine (B)

5-Bromo-3-methoxy-pyrazin-2-ylamine (A) (816 mg, 4 mmol) and phenyl boronic acid (732 mg, 6 mmol) in toluene (5 mL), ethanol (5 mL) and Na$_2$CO$_3$ (8 mmol, 1 M aqueous) was purged with nitrogen for 10 minutes, and was added PdCl$_2$(PPh$_3$)$_2$(140 mg, 0.2 mmol). The reaction mixture was stirred at 85° C. for 4 hours. The reaction mixture was cooled to room temperature and diluted with EtOAc (50 mL). The solution was washed with brine (2×5 mL). The organic extracts was dried with MgSO$_4$, then solvent was removed under vacuum. The residue was purified with flash column to give product B (660 mg, 82%) as yellow solid. $^1$H NMR (400 MHz, CDCl$_3$): δ 8.08 (1H, s), 7.92 (2H, d), 7.46 (3H, m), 4.94 (2H, bs), 4.12 (3H, s); MS: 202 (M+H$^+$).

6-Phenyl-3-amino-2-oxo-hydro-pyrazine (C)

Aniline B (100 mg, 0.5 mmol) was dissolved in glacial acetic acid (1 mL) and HBr (1 mL). The mixture was heated at 110° C. for 4 hrs. Solid crushed out and was collected by filtration to afford pyrazinone C as white solid (88 mg, 95%). $^1$H NMR (400 MHz, DMSO): δ 12.21 (1H, s), 7.82 (2H, d), 7.61 (2H, d), 7.44 (3H, m), 7.03 (1H, s). MS: 188 (M+H$^+$).

3-(2-Methylamino-propionamidyl)-6-phenyl-2-oxo-hydro-pyrazine (D)

To a solution of (S)-Boc-N-Me-Ala (244 mg, 1.2 mmol) in DMF (2.5 mL) was added HATU (547 mg, 1.44 mmol), and DIPEA (310 mg, 2.4 mmol), and the solution was stirred for 0.5 h. Then amine C (187 mg, 1 mmol) in DMF (5 mL) was added, and the solution was stirred for 16 h. Then the solution was diluted with H₂O and extracted with CH₂Cl₂, The solution was dried and the solvent removed. The crude product was purified by chromatography to afford the title compound D as white solid (255 mg, 68%): NMR (400 MHz, DMSO): δ 7.68 (2H, m), 7.51 (3H, m), 7.37 (1H, s), 4.85 (1H, bs), 2.95 (3H, s), 1.48 (12H, b); MS: 373 (M+H⁺).

3-(2-Boc-Methylamino-propionamidyl)-6-phenyl-2-oxo-hydro-pyrazyl-1-N-tetrahedron-naphthoyl)-acetamide (E)

To a solution of pyrazinone D (250 mg, 0.67 mmol) in DME (10 mL) and DMF (1 mL), was added 2-iodo-N—(R)-1,2,3,4-tetrahydro-naphthalen-1-yl-acetamide (100 mg, 0.67) and LiH (6.4 mg, 0.8 mmol). The mixture was heated at 60° C. for 10 hrs. Then the solution was diluted with H₂O and extracted with CH₂Cl₂, The solution was dried and the solvent removed. The residue was purified by flash column to give desired product E (90 mg): MS: 560 (M+H⁺).

(S)-2-Methylamino-N-(3-oxo-5-phenyl-4-{[(R)-(1,2,3,4-tetrahydro-naphthalen-1-yl)carbamoyl]-methyl}-3,4-dihydro-pyrazin-2-yl)-propionamide (example no. 30)

Compound E (90 mg, 0.16 mmol) was dissolved in dichloromethane (2 mL). To this was added 4N HCl in dioxane (2 mL). The reaction mixture was stirred for 10 h; then solvent was removed, and the resulting oil was purified by HPLC to give the title product, example no. 30 of table 2. (35 mg, 8% in two steps) as a TFA salt and as a white solid: ¹H NMR (400 MHz, MeOD): δ 8.47 (1H, d), 7.42 (5H, m), 6.98 (5H, m), 5.01 (1H, m), 4.51 (3H, m), 2.67 (5H, m), 1.81 (4H, m), 1.57 (3H, d); MS: 460 (M+H⁺).

TABLE 1

| STRUCTURE | EXAMPLE NO. | NAME | MS ESI (M + H)+ |
|---|---|---|---|
| 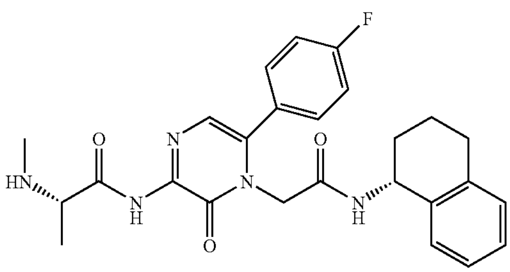 | 1 | (S)-N-(5-(4-Fluoro-phenyl)-3-oxo-{[(R)-(1,2,3,4-tetrahydro-naphthalen-1-yl)carbamoyl]-methyl}-3,4-dihydro-pyrazin-2-y1)-2-methylamino-propionamide | 478.5 |
| 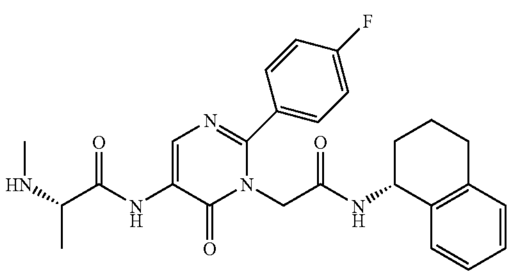 | 2 | (S)-N-(2-(4-Fluoro-phenyl)-6-oxo-1-{[(R)-(1,2,3,4-tetrahydro-naphthalen-1-yl)carbamoyl]-methyl}-1,6-dihydro-pyrimidin-5-yl)-2-methylamino-propionamide | 478.5 |
| 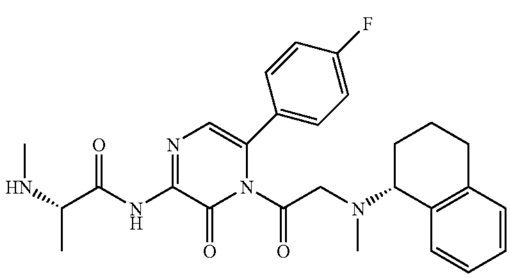 | 3 | (S)-N-{5-(4-Fluoro-phenyl)-4-[2-((R)-methyl-1,2,3,4-tetrahydro-naphthalen-1-yl-amino)-acetyl]-3-oxo-3,4-dihydro-pyrazin-2-yl}-2-methylamino-propionamide | 492.6 |
| 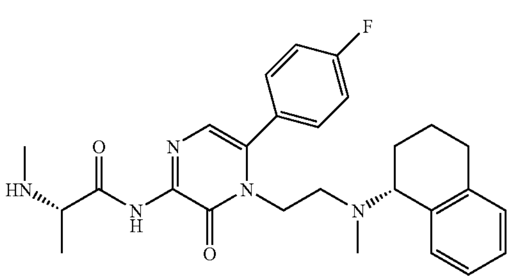 | 4 | (S)-N-{5-(4-Fluoro-phenyl)-4-[2-((R)-methyl-1,2,3,4-tetrahydro-naphthalen-1-yl-amino)-ethyl]-3-oxo-3,4-dihydro-pyrazin-2-yl}-2-methylamino-propionamide | 478.6 |

TABLE 1-continued

| STRUCTURE | EXAMPLE NO. | NAME | MS ESI (M + H)+ |
|---|---|---|---|
| 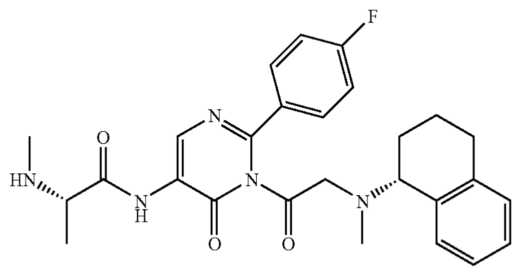 | 5 | (S)-N-{2-(4-Fluoro-phenyl)-1-[2-((R)-methyl-1,2,3,4-tetrahydro-naphthalen-1-yl-amino)-acetyl]-6-oxo-1,6-dihydro-pyrimidin-5-yl}-2-methylamino-propionamide | 492.6 |
| 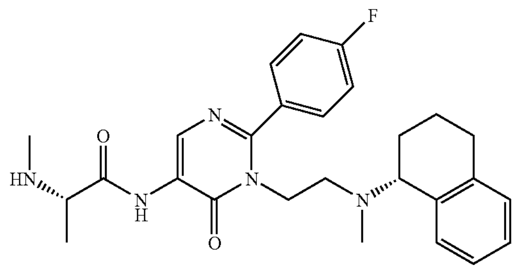 | 6 | (S)-N-{2-(4-Fluoro-phenyl)-1-[2-((R)-methyl-1,2,3,4-tetrahydro-naphthalen-1-yl-amino)-ethyl]-6-oxo-1,6-dihydro-pyrimidin-5-yl}-2-methylamino-propionamide | 478.6 |
| 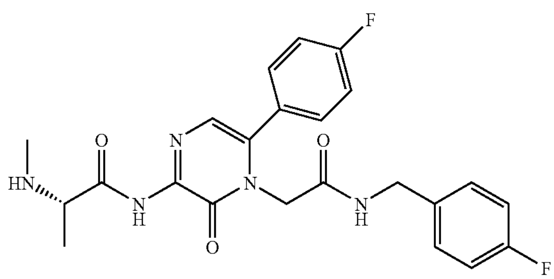 | 7 | (S)-N-[4-[(4-Fluoro-benzylcarbamoyl)-methyl]-5-(4-fluoro-phenyl)-3-oxo-3,4-dihydro-pyrazin-2-yl]-2-methylamino-propionamide | 456.5 |
| 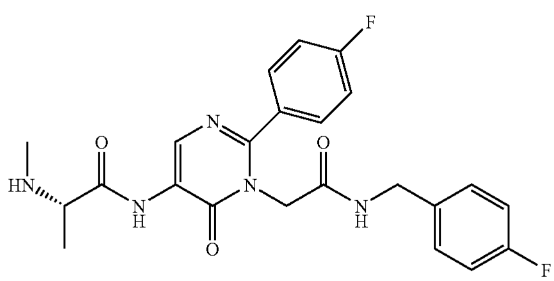 | 8 | (S)-N-[1-[(4-Fluoro-benzylcarbamoyl)-methyl]-2-(4-fluoro-phenyl)-6-oxo-1,6-dihydro-pyrimidin-5-yl]-2-methylamino-propionamide | 456.5 |
| 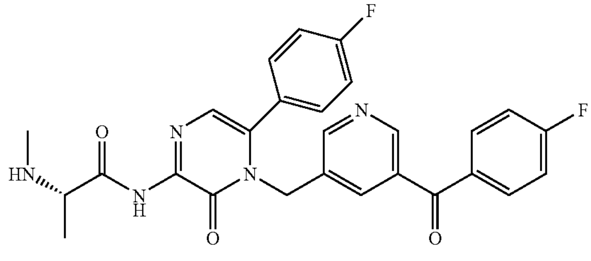 | 9 | (S)-N-[4-[5-(4-Fluoro-benzoyl)-pyridin-3-ylmethyl]-5-(4-fluoro-phenyl)-3-oxo-3,4-di-hydro-pyrazin-2-yl]-2-methylamino-propionamide | 504.5 |

TABLE 1-continued

| STRUCTURE | EXAMPLE NO. | NAME | MS ESI (M + H)+ |
|---|---|---|---|
| 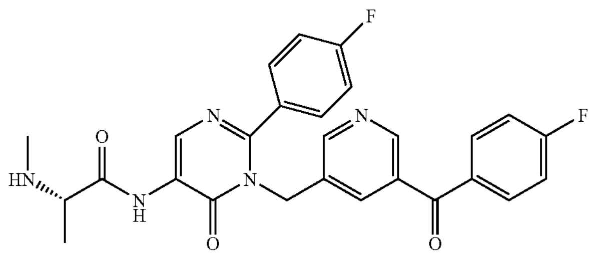 | 10 | (S)-N-[1-[5-(4-Fluoro-benzoyl)-pyridin-3-ylmethyl]-2-(4-fluoro-phenyl)-6-oxo-1,6-dihydro-pyrimidin-5-yl]-2-methylamino-propionamide | 504.5 |
| 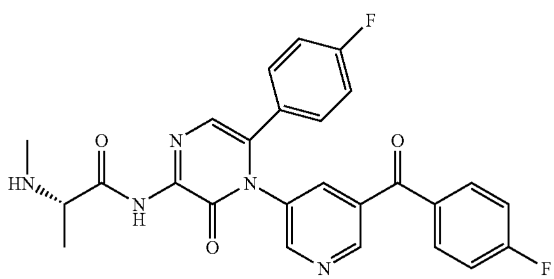 | 11 | (S)-N-[4-[5-(4-Fluoro-benzoyl)-pyridin-3-yl]-5-(4-fluoro-phenyl)-3-oxo-3,4-dihydro-pyrazin-2-yl]-2-methylamino-propionamide | 490.5 |
| 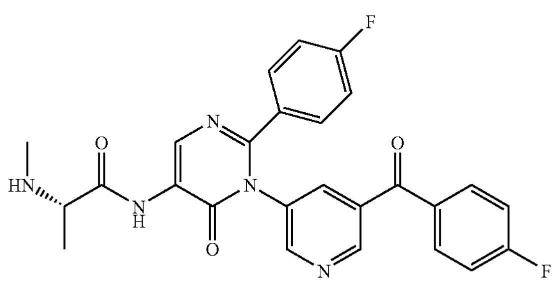 | 12 | (S)-N-[1-[5-(4-Fluoro-benzoyl)-pyridin-3-yl]-2-(4-fluoro-phenyl)-6-oxo-1,6-dihydro-pyrimidin-5-yl]-2-methylamino-propionamide | 490.5 |
| 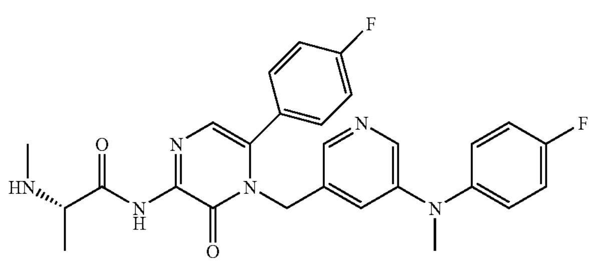 | 13 | (S)-N-(5-(4-Fluoro-phenyl)-4-{5-[(4-fluoro-phenyl)-methyl-amino]-pyridin-3-ylmethyl}-3-oxo-3,4-dihydro-pyrazin-2-yl)-2-methylamino-propionamide | 505.5 |
| 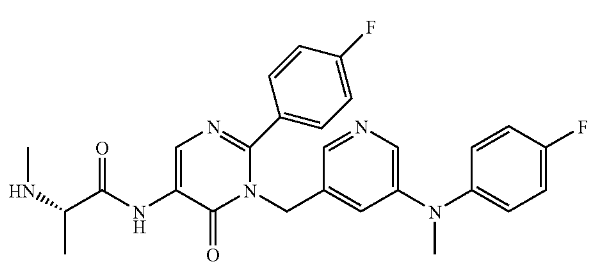 | 14 | (S)-N-(2-(4-Fluoro-phenyl)-1-{5-[(4-fluoro-phenyl)-methyl-amino]-pyridin-3-ylmethyl}-6-oxo-1,6-dihydro-pyrimidin-5-yl)-2-methylamino-propionamide | 505.5 |

TABLE 1-continued

| STRUCTURE | EXAMPLE NO. | NAME | MS ESI (M + H)+ |
|---|---|---|---|
| 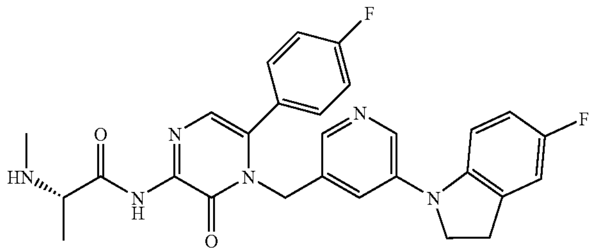 | 15 | (S)-N-[4-[5-(5-Fluoro-2,3-dihydro-indol-1-yl)-pyridin-3-ylmethyl]-5-(4-fluoro-phenyl)-3-oxo-3,4-dihydro-pyrazin-2-yl]-2-methylamino-propionamide | 517.6 |
| 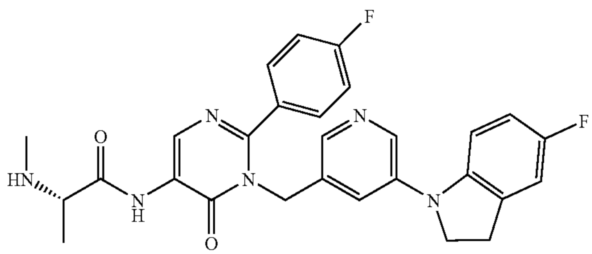 | 16 | (S)-N-[1-[5-(5-Fluoro-2,3-dihydro-indol-1-yl)-pyridin-3-ylmethyl]-2-(4-fluoro-phenyl)-6-oxo-1,6-dihydro-pyrimidin-5-yl]-2-methylamino-propionamide | 517.6 |
| 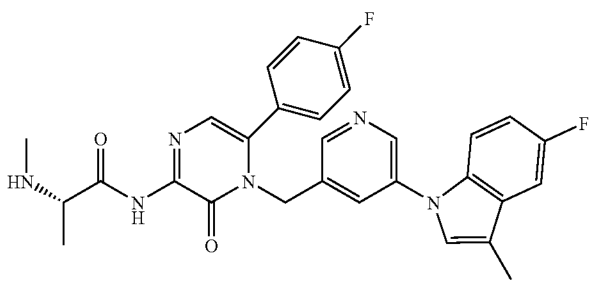 | 17 | (S)-N-[4-[5-(5-Fluoro-3-methyl-indol-1-yl)-pyridin-3-ylmethyl]-5-(4-fluoro-phenyl)-3-oxo-3,4-dihydro-pyrazin-2-yl]-2-methylamino-propionamide | 529.6 |
| 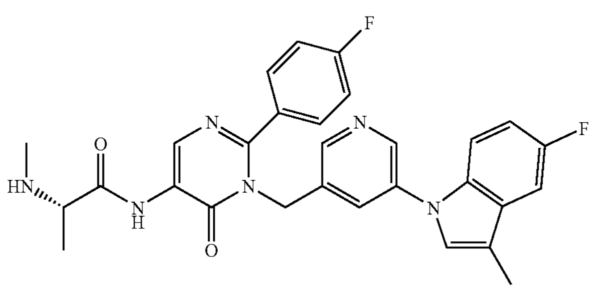 | 18 | (S)-N-[1-[5-(5-Fluoro-3-methyl-indol-1-yl)-pyridin-3-ylmethyl]-2-(4-fluoro-phenyl)-6-oxo-1,6-dihydro-pyrimidin-5-yl]-2-methylamino-propionamide | 529.6 |
| 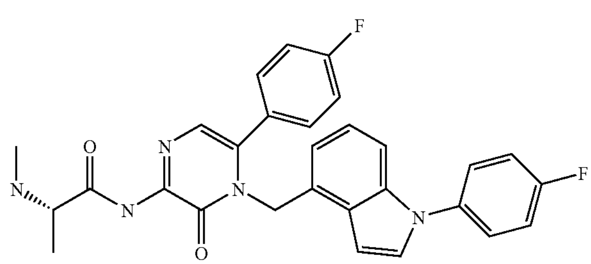 | 19 | (S)-N-{5-(4-Fluoro-phenyl)-4-[1-(4-fluoro-phenyl)-1H-indol-4-ylmethyl]-3-oxo-3,4-dihydro-pyrazin-2-yl}-2-methylamino-propionamide | 514.2 |

TABLE 1-continued

| STRUCTURE | EXAMPLE NO. | NAME | MS ESI (M + H)+ |
|---|---|---|---|
| 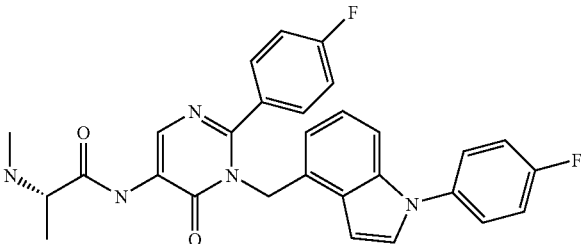 | 20 | (S)-N-{2-(4-Fluoro-phenyl)-1-[1-(4-fluoro-phenyl)-1-indol-4-ylmethyl]-6-oxo-1,6-dihydro-pyrimidin-5-yl}-2-methylamino-propionamide | 514.2 |
| 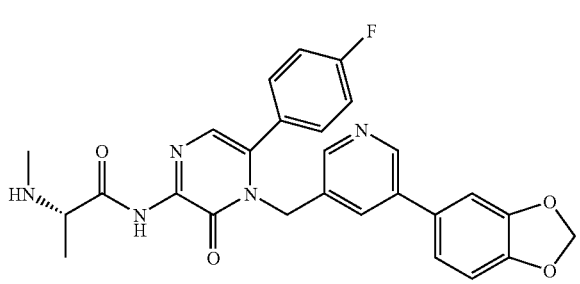 | 21 | (S)-N-[4-(5-Benzo[1,3]dioxol-5-yl-pyridin-3-ylmethyl)-5-(4-fluoro-phenyl)-3-oxo-3,4-dihydro-pyrazin-2-yl]-2-methylamino-propionamide | 502.5 |
| 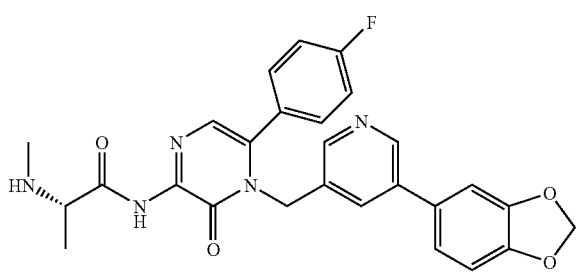 | 22 | (S)-N-[1-(5-Benzo[1,3]dioxol-5-yl-pyridin-3-ylmethyl)-2-(4-fluoro-phenyl)-6-oxo-1,6-dihydro-pyrimidin-5-yl]-2-methylamino-propionamide | 512.5 |
| 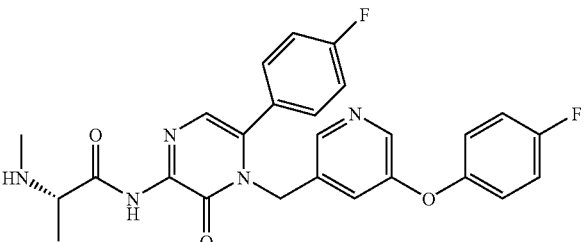 | 23 | (S)-N-[4-[5-(4-Fluoro-phenoxy)-pyridin-3-ylmethyl]-5-(4-fluoro-phenyl)-3-oxo-3,4-dihydro-pyrazin-2-yl]-2-methylamino-propionamide | 492.6 |
| 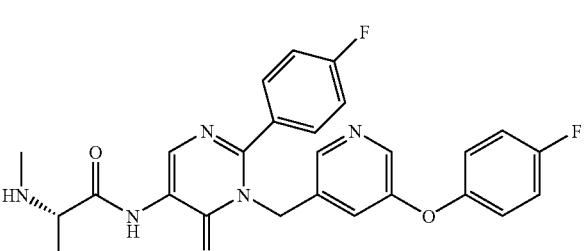 | 24 | (S)-N-[1-[5-(4-Fluoro-phenoxy)-pyridin-3-ylmethyl]-2-(4-fluoro-phenyl)-6-oxo-1,6-dihydro-pyrimidin-5-yl]-2-methylamino-propionamide | 492.6 |
| 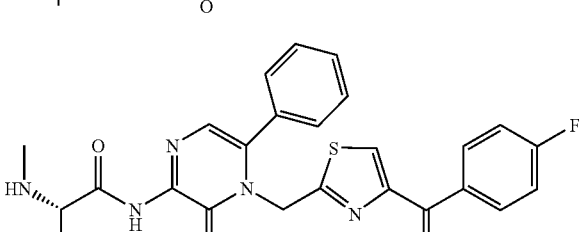 | 25 | (S)-N-{4-[4-(4-Fluoro-benzoyl)-thiazol-2-ylmethyl]-3-oxo-5-phenyl-3,4-dihydro-pyrazin-2-yl}-2-methylamino-propionamide | 492.5 |

TABLE 1-continued

| STRUCTURE | EXAMPLE NO. | NAME | MS ESI (M + H)+ |
|---|---|---|---|
| 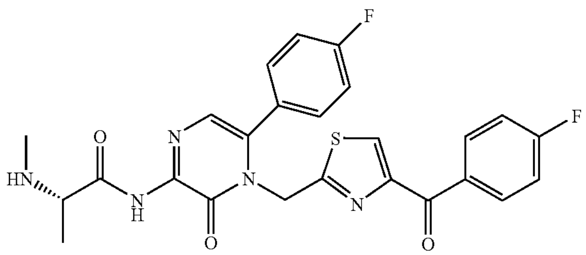 | 26 | (S)-N-[4-[4-(4-Fluoro-benzoyl)-thiazol-2-ylmethyl]-5-(4-fluoro-phenyl)-3-oxo-3,4-dihydro-pyrazin-2-yl]-2-methylamino-propionamide | 510.5 |
| 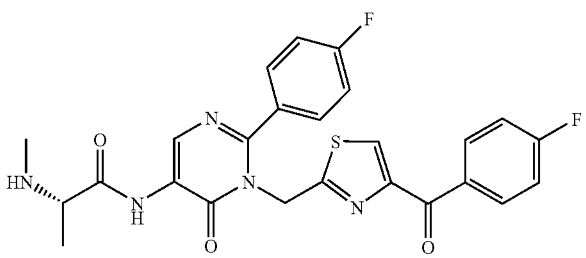 | 27 | (S)-N-[1-[4-(4-Fluoro-benzoyl)-thiazol-2-ylmethyl]-2-(4-fluoro-phenyl)-6-oxo-1,6-dihydro-pyrimidin-5-yl]-2-methylamino-propionamide | 510.5 |
| 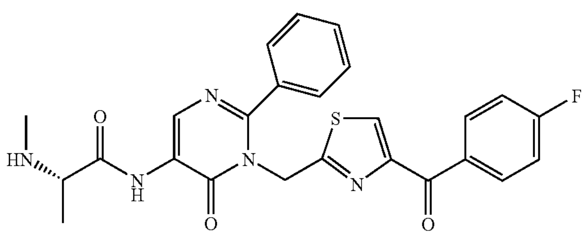 | 28 | (S)-N-{1-[4-(4-Fluoro-benzoyl)-thiazol-2-ylmethyl]-6-oxo-2-phenyl-1,6-dihydro-pyrimidin-5-yl}-2-methylamino-propionamide | 492.5 |

TABLE 2

| Structure | Example No. | name | MS ESI (M + H)+ |
|---|---|---|---|
| 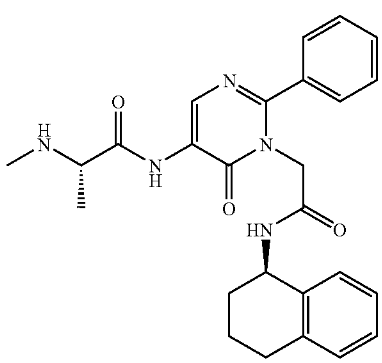 | 29 | (S)-2-Methylamino-N-(6-oxo-2-phenyl-1-{[(R)-(1,2,3,4-tetrahydro-naphthalen-1-yl)carbamoyl]-methyl}-1,6-dihydro-pyrimidin-5-yl)-propionamide | 460.2 |

TABLE 2-continued

| Structure | Example No. | name | MS ESI (M + H)+ |
|---|---|---|---|
| 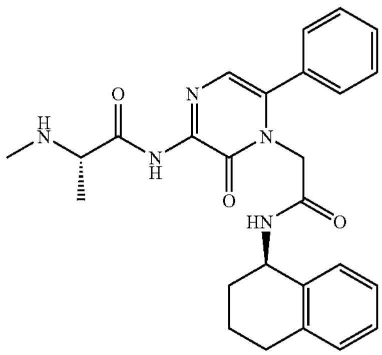 | 30 | (S)-2-Methylamino-N-(3-oxo-5-phenyl-4-{[(R)-(1,2,3,4-tetrahydro-naphthalen-1-yl)carbamoyl]-methyl}-3,4-dihydro-pyrazin-2-yl)-propionamide | 460.2 |
| 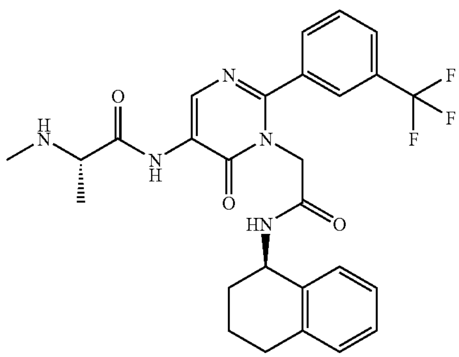 | 31 | (S)-N-(2-(3-Trifluoromethyl-phenyl)-6-oxo-1-{[(R)-(1,2,3,4-tetrahydro-naphthalen-1-yl)carbamoyl]-methyl}-1,6-dihydro-pyrimidin-5-yl)-2-methylamino-propionamide | 528.2 |
| 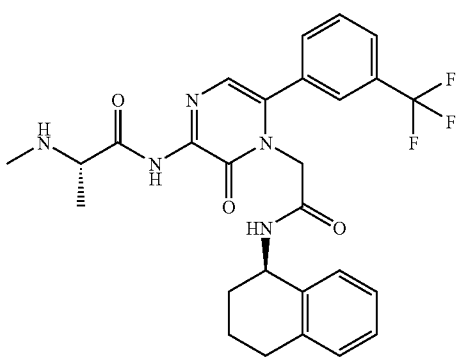 | 32 | (S)-N-(5-(3-Trifluoromethyl-phenyl)-3-oxo-4-{[(R)-(1,2,3,4-tetrahydro-naphthalen-1-yl)carbamoyl]-methyl}-3,4-dihydro-pyrazin-2-yl)-2-methylamino-propionamide | 528.2 |
| 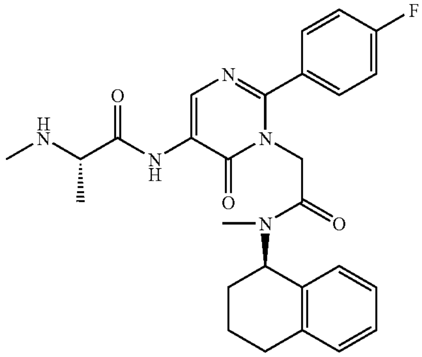 | 33 | (S)-N-{2-(4-Fluoro-phenyl)-1-[((R)-methyl-1,2,3,4-tetrahydro-naphthalen-1-yl-carbamoyl)-methyl]-6-oxo-1,6-dihydro-pyrimidin-5-yl}-2-methylamino-propionamide | 492.2 |

TABLE 2-continued

| Structure | Example No. | name | MS ESI (M + H)+ |
|---|---|---|---|
| 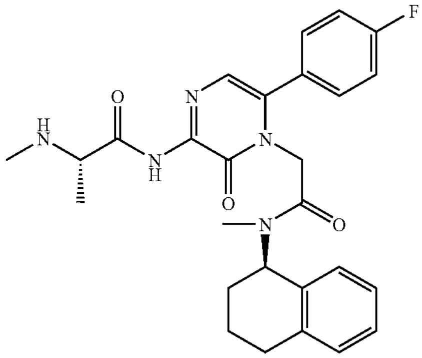 | 34 | (S)-N-{5-(4-Fluoro-phenyl)-4-[((R)-methyl-1,2,3,4-tetrahydro-naphthalen-1-yl-carbamoyl)-methyl]-3-oxo-3,4-dihydro-pyrazin-2-yl}-2-methylamino-propionamide | 492.2 |
| 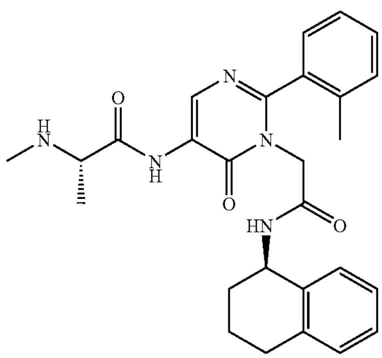 | 35 | (S)-2-Methylamino-N-(6-oxo-1-{[(R)-(1,2,3,4-tetrahydro-naphthalen-1-yl)carbamoyl]-methyl}-2-o-tolyl-1,6-dihydro-pyrimidin-5-yl)-propionamide | 474.2 |
| 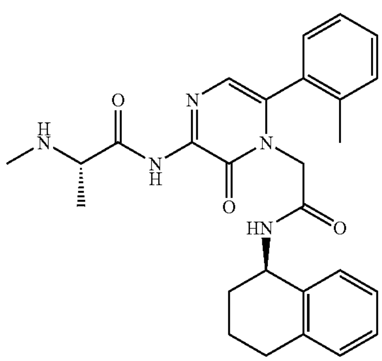 | 36 | (S)-2-Methylamino-N-(3-oxo-4-{[(R)-(1,2,3,4-tetrahydro-naphthalen-1-yl)carbamoyl]-methyl}-5-o-tolyl-3,4-dihydro-pyrazin-2-yl)-propionamide | 474.2 |
| 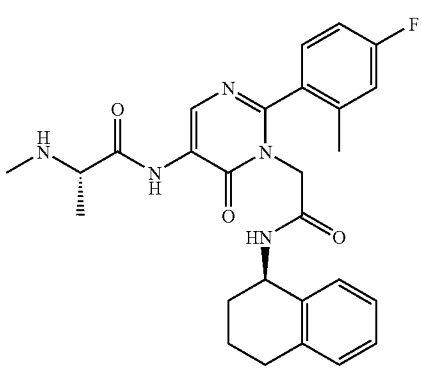 | 37 | (S)-N-(2-(4-Fluoro-2-methyl-phenyl)-6-oxo-1-{[(R)-(1,2,3,4-tetrahydro-naphthalen-1-yl)carbamoyl]-methyl}-1,6-dihydro-pyrimidin-5-yl)-2-methylamino-propionamide | 492.2 |

TABLE 2-continued

| Structure | Example No. | name | MS ESI (M + H)+ |
|---|---|---|---|
| 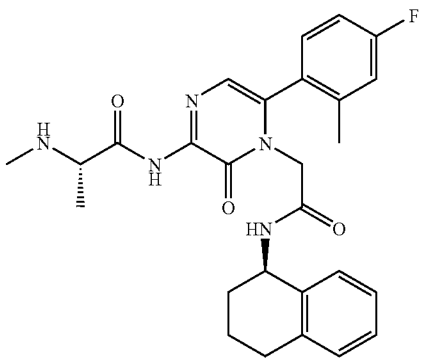 | 38 | (S)-N-(5-(4-Fluoro-2-methyl-phenyl)-3-oxo-4-{[(R)-(1,2,3,4-tetrahydro-naphthalen-1-yl)carbamoyl]-methyl}-3,4-dihydro-pyrazin-2-yl)-2-methylamino-propionamide | 492.2 |
| 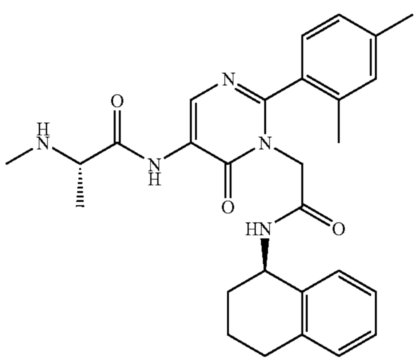 | 39 | (S)-N-(2-(2,4-Dimethyl-phenyl)-6-oxo-1-{[(R)-(1,2,3,4-tetrahydro-naphthalen-1-yl)carbamoyl]-methyl}-1,6-dihydro-pyrimidin-5-yl)-2-methylamino-propionamide | 488.3 |
| 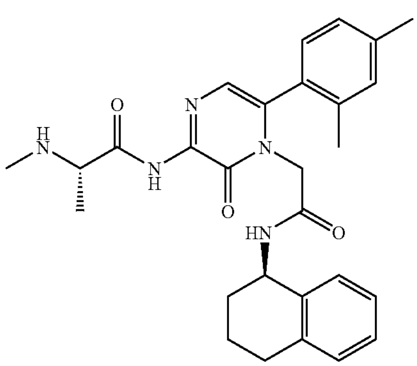 | 40 | (S)-N-(5-(2,4-Dimethyl-phenyl)-3-oxo-4-{[(R)-(1,2,3,4-tetrahydro-naphthalen-1-yl)carbamoyl]-methyl}-3,4-dihydro-pyrazin-2-yl)-2-methylamino-propionamide | 488.3 |
| 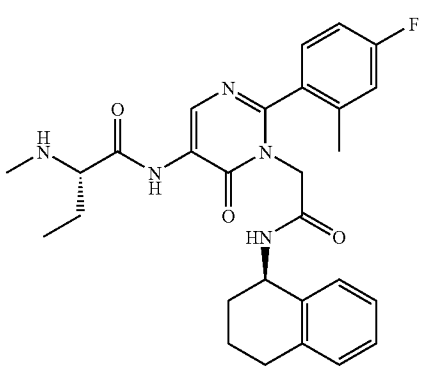 | 41 | (S)-N-(2-(4-Fluoro-2-methyl-phenyl)-6-oxo-1-{[(R)-(1,2,3,4-tetrahydro-naphthalen-1-yl)carbamoyl]-methyl}-1,6-dihydro-pyrimidin-5-yl)-2-methylamino-butyramide | 506.2 |

TABLE 2-continued

| Structure | Example No. | name | MS ESI (M + H)+ |
|---|---|---|---|
| 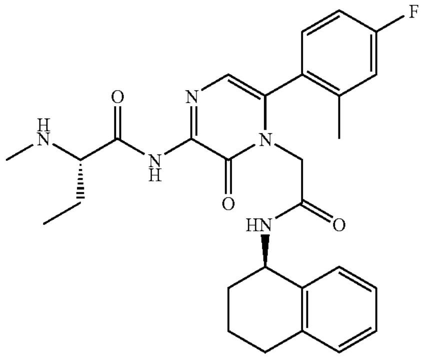 | 42 | (S)-N-(5-(4-Fluoro-2-methyl-phenyl)-3-oxo-4-{[(R)-(1,2,3,4-tetrahydro-naphthalen-1-yl)carbamoyl]-methyl}-3,4-dihydro-pyrazin-2-yl)-2-methylamino-butyramide | 506.2 |
| 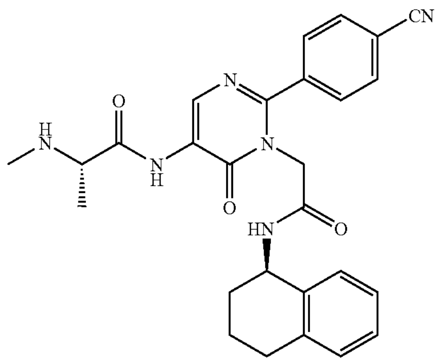 | 43 | (S)-N-(2-(4-Cyano-phenyl)-6-oxo-1-{[(R)-(1,2,3,4-tetrahydro-naphthalen-1-yl)carbamoyl]-methyl}-1,6-dihydro-pyrimidin-5-yl)-2-methylamino-propionamide | 485.2 |
| 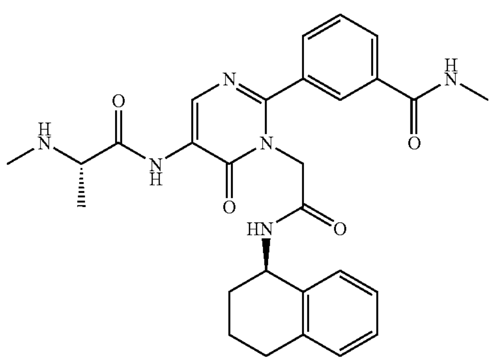 | 44 | N-Methyl-3-(5-((S)-2-methylamino-propionylamino)-6-oxo-1-{[(R)-(1,2,3,4-tetrahydro-naphthalen-1-yl)carbamoyl]-methyl}-1,6-dihydro-pyrimidin-2-yl)-benzamide | 518.3 |
| 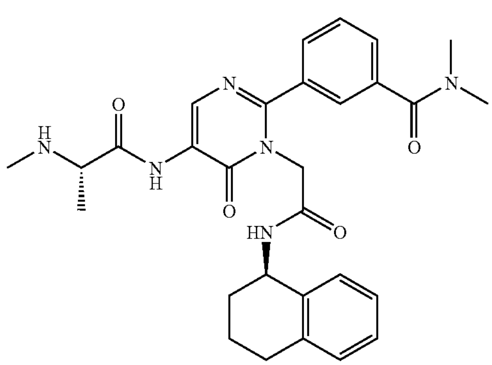 | 45 | N,N-Dimethyl-3-(5-((S)-2-methylamino-propionylamino)-6-oxo-1-{[(R)-(1,2,3,4-tetrahydro-naphthalen-1-yl)carbamoyl]-methyl}-1,6-dihydro-pyrimidin-2-yl)-benzamide | 531.3 |

TABLE 2-continued

| Structure | Example No. | name | MS ESI (M + H)+ |
|---|---|---|---|
| 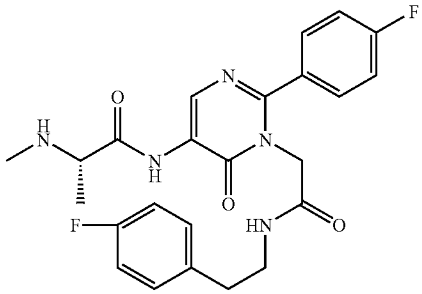 | 46 | (S)-N-(2-(4-Fluoro-phenyl)-1-{[2-(4-fluoro-phenyl)-ethylcarbamoyl]-methyl}-6-oxo-1,6-dihydro-pyrimidin-5-yl)-2-methylamino-propionamide | 470.2 |
| 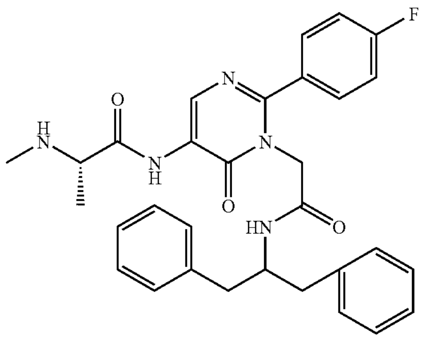 | 47 | (S)-N-[1-[(1-Benzyl-2-phenyl-ethylcarbamoyl)-methyl]-2-(4-fluoro-phenyl)-6-oxo-1,6-dihydro-pyrimidin-5-yl]-2-methylamino-propionamide | 541.2 |
| 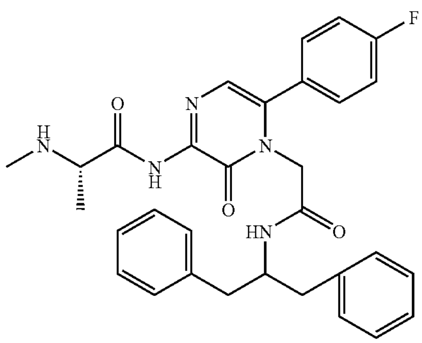 | 48 | (S)-N-[4-[(1-Benzyl-2-phenyl-ethylcarbamoyl)-methyl]-2-(4-fluoro-phenyl)-3-oxo-3,4-dihydro-pyrazin-2-yl]-2-methylamino-propionamide | 541.2 |
| 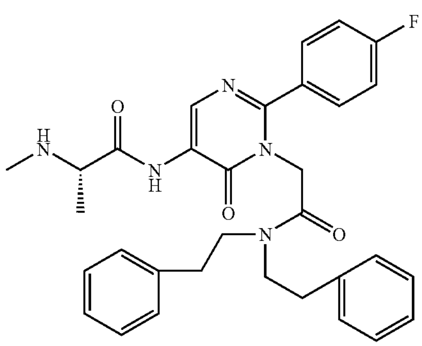 | 49 | (S)-N-[1-[(Diphenethylcarbamoyl)-methyl]-2-(4-fluoro-phenyl)-6-oxo-1,6-dihydro-pyrimidin-5-yl]-2-methylamino-propionamide | 556.3 |

TABLE 2-continued

| Structure | Example No. | name | MS ESI (M + H)+ |
|---|---|---|---|
| 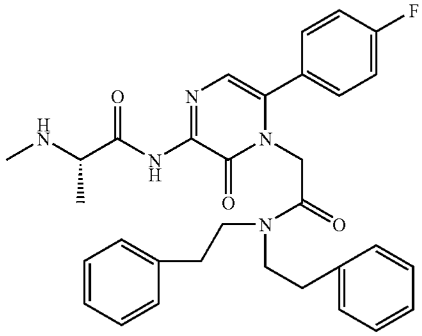 | 50 | (S)-N-[4-[(Diphenethylcarbamoyl)-methyl]-5-(4-fluoro-phenyl)-3-oxo-3,4-dihydro-pyrazin-2-yl]-2-methylamino-propionamide | 556.3 |
| 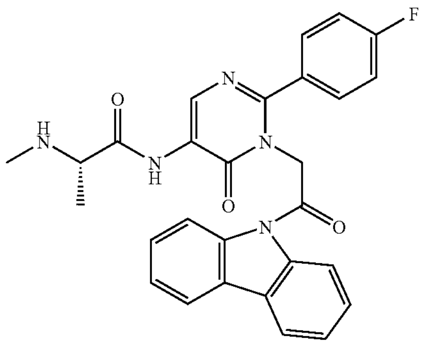 | 51 | (S)-N-[1-(2-Carbazol-9-yl-2-oxo-ethyl)-2-(4-fluoro-phenyl)-6-oxo-1,6-dihydro-pyrimidin-5-yl]-2-methylamino-propionamide | 498.2 |
| 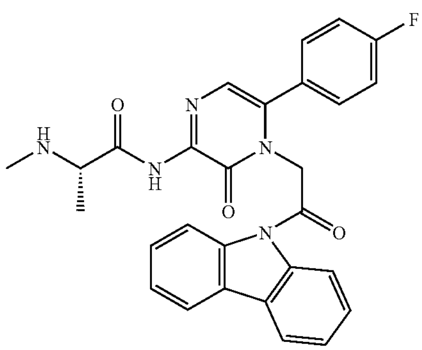 | 52 | (S)-N-[4-(2-Carbazol-9-yl-2-oxo-ethyl)-5-(4-fluoro-phenyl)-3-oxo-3,4-dihydro-pyrazin-2-yl]-2-methylamino-propionamide | 498.2 |
| 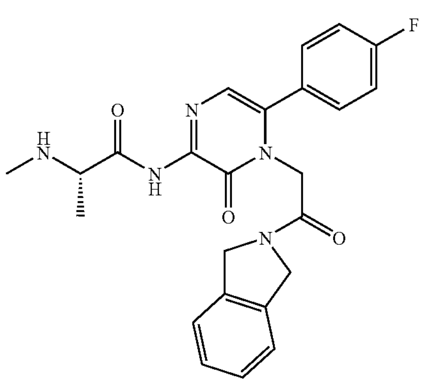 | 53 | (S)-N-[4-[2-(1,3-Dihydro-isoindol-2-yl)-2-oxo-ethyl]-5-(4-fluoro-phenyl)-3-oxo-3,4-dihydro-pyrazin-2-yl]-2-methylamino-propionamide | 450.2 |

TABLE 2-continued

| Structure | Example No. | name | MS ESI (M + H)+ |
|---|---|---|---|
| 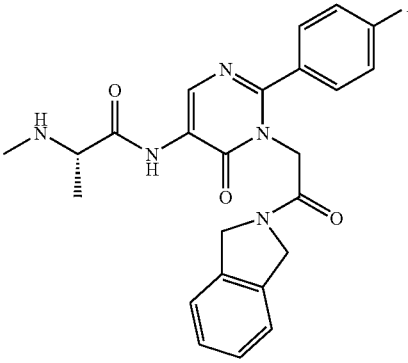 | 54 | (S)-N-[1-[2-(1,3-Dihydro-isoindol-2-yl)-2-oxo-ethyl]-2-(4-fluoro-phenyl)-6-oxo-1,6-dihydro-pyrimidin-5-yl]-2-methylamino-propionamide | 450.2 |
| 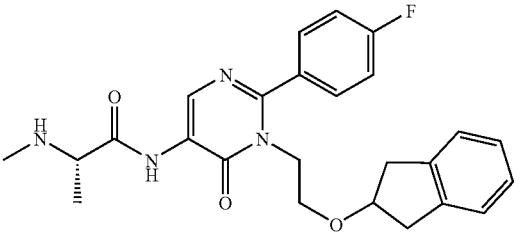 | 55 | (S)-N-{2-(4-Fluoro-phenyl)-1-[2-(indan-2-yloxy)-ethyl]-6-oxo-1,6-dihydro-pyrimidin-5-yl}-2-methylamino-propionamide | 451.2 |
| 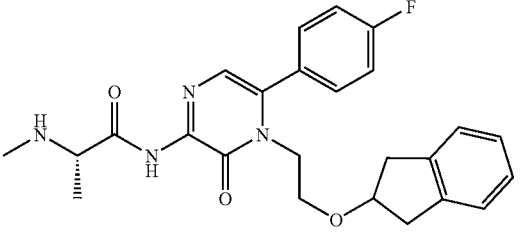 | 56 | (S)-N-{5-(4-Fluoro-phenyl)-4-[2-(indan-2-yloxy)-ethyl]-3-oxo-3,4-dihydro-pyrazin-2-yl}-2-methylamino-propionamide | 451.2 |
| 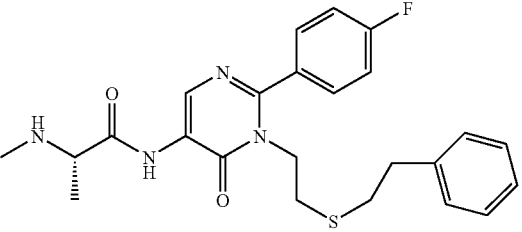 | 57 | (S)-N-[2-(4-Fluoro-phenyl)-6-oxo-1-(2-phenethyl-sulfanyl-ethyl)-1,6-dihydro-pyrimidin-5-yl]-2-methylamino-propionamide | 455.2 |
| 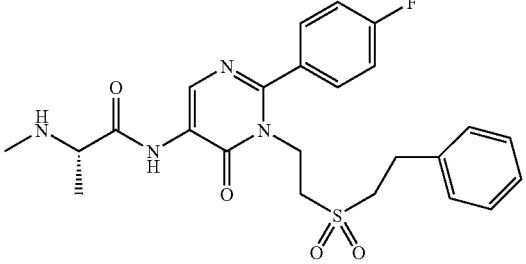 | 58 | (S)-N-{2-(4-Fluoro-phenyl)-6-oxo-1-[2-(2-phenyl-ethanesulfonyl)-ethyl]-1,6-dihydro-pyrimidin-5-yl}-2-methylamino-propionamide | 487.2 |

TABLE 2-continued

| Structure | Example No. | name | MS ESI (M + H)+ |
|---|---|---|---|
| 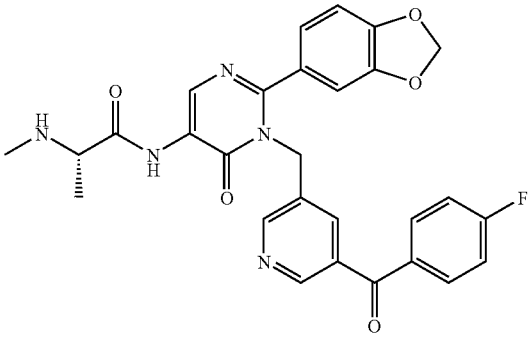 | 59 | (S)-N-{2-Benzo[1,3]dioxol-5-yl-1-[5-(4-fluoro-benzoyl)-pyridin-3-ylmethyl]-6-oxo-1,6-dihydro-pyrimidin-5-yl}-2-methylamino-propionamide | 530.2 |
| 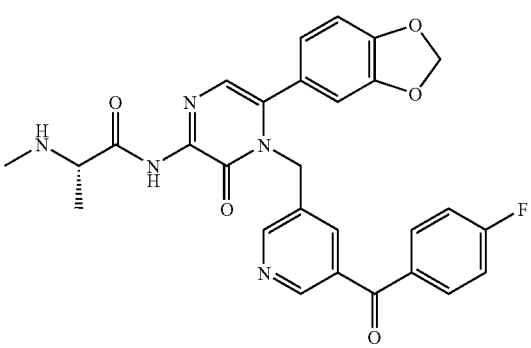 | 60 | (S)-N-{5-Benzo[1,3]dioxol-5-yl-4-[5-(4-fluoro-benzoyl)-pyridin-3-ylmethyl]-3-oxo-3,4-dihydro-pyrazin-2-yl}-2-methylamino-propionamide | 530.2 |
| 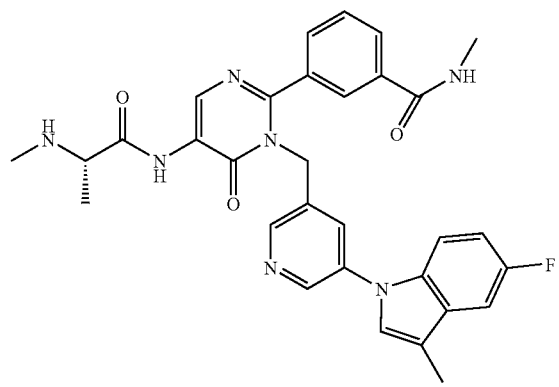 | 61 | 3-[1-[5-(5-Fluoro-3-methyl-indol-1-yl)-pyridin-3-ylmethyl]-5-((S)-2-methylamino-propionylamino)-6-oxo-1,6-dihydro-pyrimidin-2-yl]-N-methyl-benzamide | 568.2 |
| 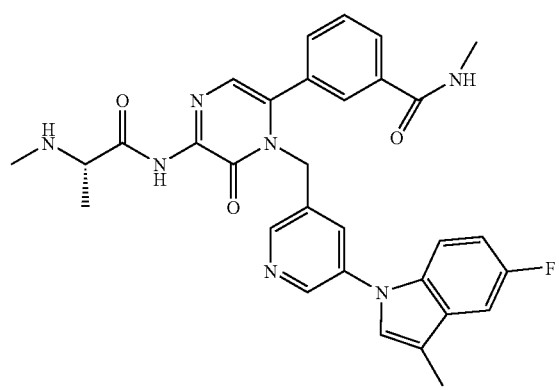 | 62 | 3-[1-[5-(5-Fluoro-3-methyl-indol-1-yl)-pyridin-3-ylmethyl]-5-((S)-2-methylamino-propionylamino)-6-oxo-1,6-dihydro-pyrazin-2-yl]-N-methyl-benzamide | 568.2 |

TABLE 2-continued

| Structure | Example No. | name | MS ESI (M + H)+ |
|---|---|---|---|
| 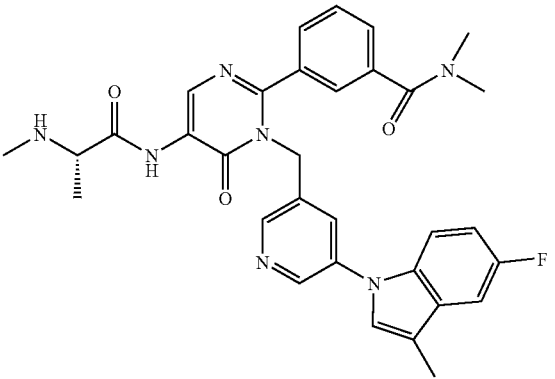 | 63 | 3-[1-[5-(5-Fluoro-3-methyl-indol-1-yl)-pyridin-3-ylmethyl]-5-((S)-2-methylamino-propionylamino)-6-oxo-1,6-dihydro-pyrimidin-2-yl]-N,N-dimethyl-benzamide | 582.3 |
| 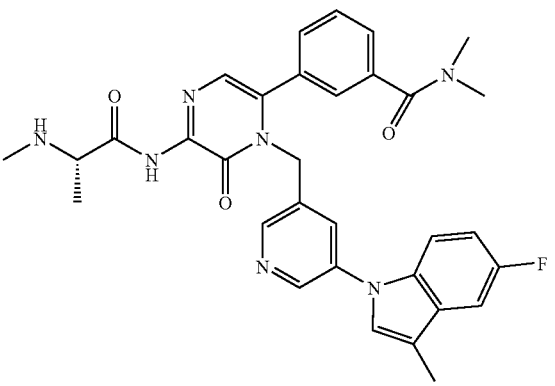 | 64 | 3-[1-(5-(5-Fluoro-3-methyl-indol-1-yl)-pyridin-3-ylmethyl]-5-((S)-2-methylamino-propionylamino)-6-oxo-1,6-dihydro-pyrazin-2-yl]-N,N-dimethyl-benzamide | 582.3 |
| 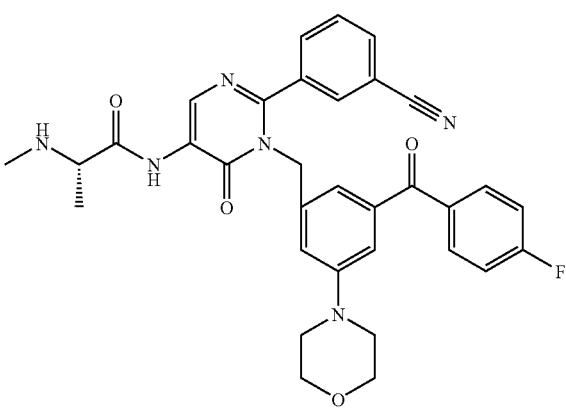 | 65 | S)-N-{2-(3-Cyano-phenyl)-1-[3-(4-fluoro-benzoyl)-5-morpholin-4-yl-benzyl]-6-oxo-1,6-dihydro-pyrimidin-5-yl}-2-methylamino-propionamide | 595.2 |
| 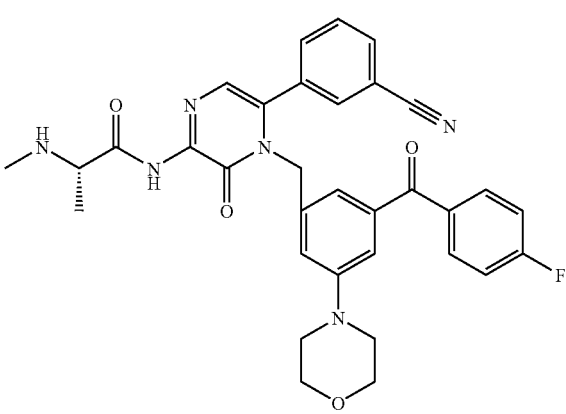 | 66 | (S)-N-{5-(3-Cyano-phenyl)-4-[3-(4-fluoro-benzoyl)-5-morpholin-4-yl-benzyl]-3-oxo-3,4-dihydro-pyrazin-2-yl}-2-methylamino-propionamide | 595.2 |

TABLE 2-continued

| Structure | Example No. | name | MS ESI (M + H)+ |
|---|---|---|---|
| 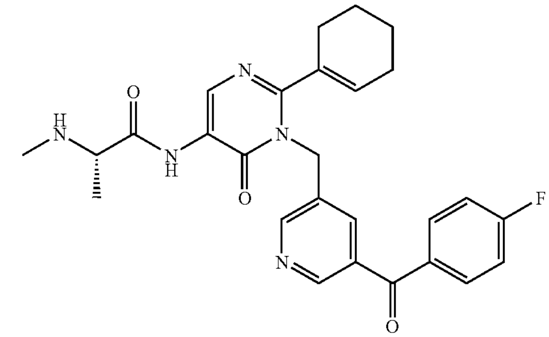 | 67 | (S)-N-{2-Cyclohex-1-enyl-1-[5-(4-fluoro-benzoyl)-pyridin-3-ylmethyl]-6-oxo-1,6-dihydro-pyrimidin-5-yl}-2-methylamino-propionamide | 490.2 |
| 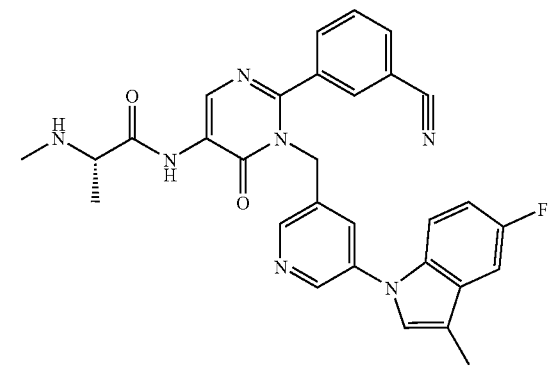 | 68 | (S)-N-{2-(3-Cyano-phenyl)-1-[5-(5-fluoro-3-methyl-indol-1-yl)-pyridin-3-ylmethyl]-6-oxo-1,6-dihydro-pyrimidin-5-yl}-2-methylamino-propionamide | 536.2 |
| 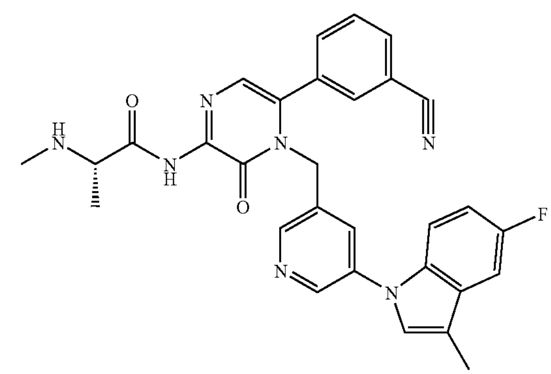 | 69 | (S)-N-{5-(3-Cyano-phenyl)-4-[5-(5-fluoro-3-methyl-indol-1-yl)-pyridin-3-ylmethyl]-3-oxo-3,4-dihydro-pyrazin-2-yl}-2-methylamino-propionamide | 536.2 |
| 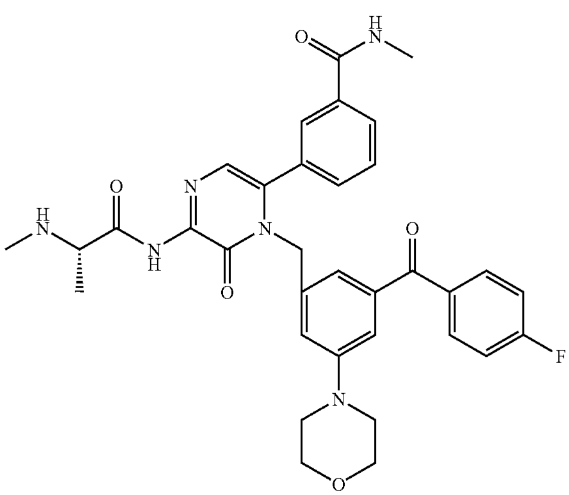 | 70 | 3-[1-[3-(4-Fluoro-benzoyl)-5-morpholin-4-yl-benzyl]-5-((S)-2-methylamino-propionylamino)-6-oxo-1,6-dihydro-pyrazin-2-yl]-N-methyl-benzamide | 627.3 |

TABLE 2-continued

| Structure | Example No. | name | MS ESI (M + H)+ |
|---|---|---|---|
| 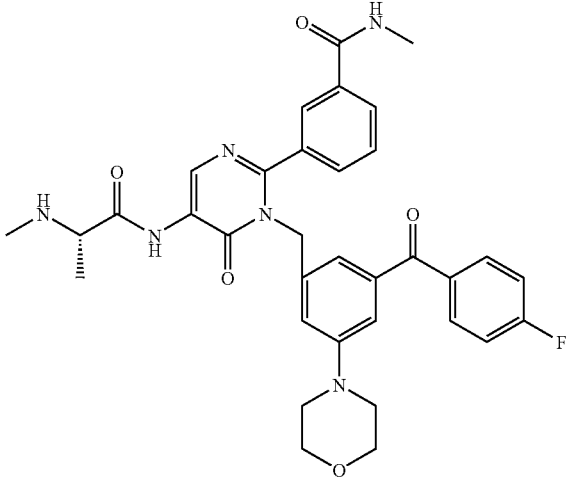 | 71 | 3-[1-[3-(4-Fluoro-benzoyl)-5-morpholin-4-yl-benzyl]-5-((S)-2-methylamino-propionylamino)-6-oxo-1,6-dihydro-pyrimidin-2-yl]-N-methyl-benzamide | 627.3 |
| 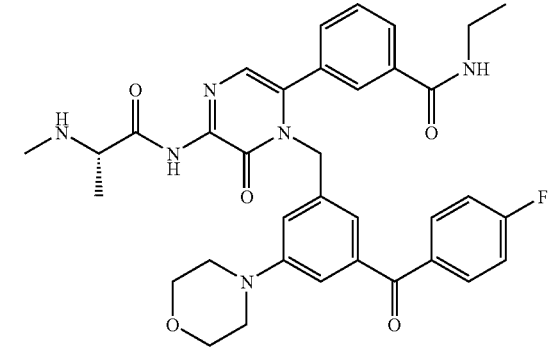 | 72 | N-Ethyl-3-[1-[3-(4-fluoro-benzoyl)-5-morpholin-4-yl-benzyl]-5-((S)-2-methylamino-propionylamino)-6-oxo-1,6-dihydro-pyrazin-2-yl]-benzamide | 641.3 |
| 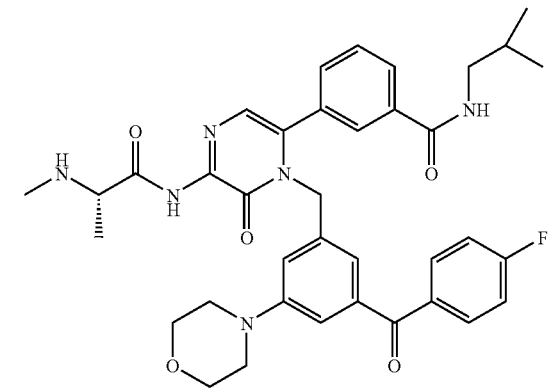 | 73 | 3-[1-[3-(4-Fluoro-benzoyl)-5-morpholin-4-yl-benzyl]-5-((S)-2-methylamino-propionylamino)-6-oxo-1,6-dihydro-pyrazin-2-yl]-N-isobutyl-benzamide | 669.3 |
| 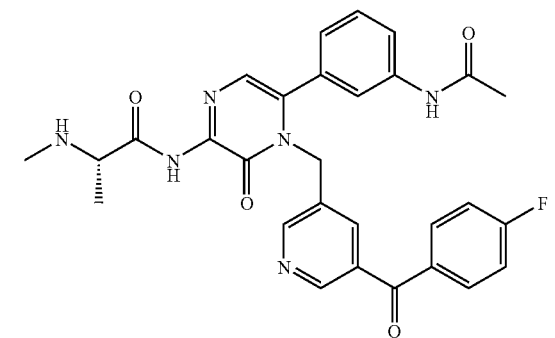 | 74 | (S)-N-{5-(3-Acetylamino-phenyl)-4-[5-(4-fluoro-benzoyl)-pyridin-3-ylmethyl]-3-oxo-3,4-dihydro-pyrazin-2-yl}-2-methylamino-propionamide | 543.2 |

TABLE 2-continued

| Structure | Example No. | name | MS ESI (M + H)+ |
|---|---|---|---|
| 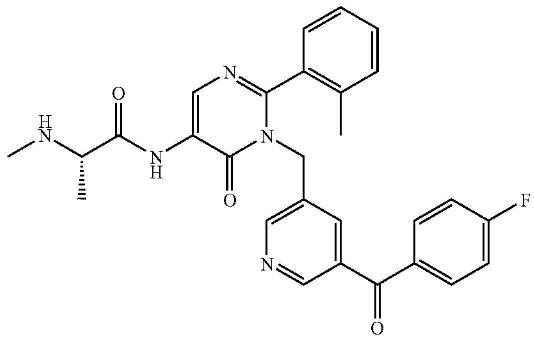 | 75 | (S)-N-{1-[5-(4-Fluoro-benzoyl)-pyridin-3-ylmethyl]-6-oxo-2-o-tolyl-1,6-dihydro-pyrimidin-5-yl}-2-methylamino-propionamide | 500.2 |
| 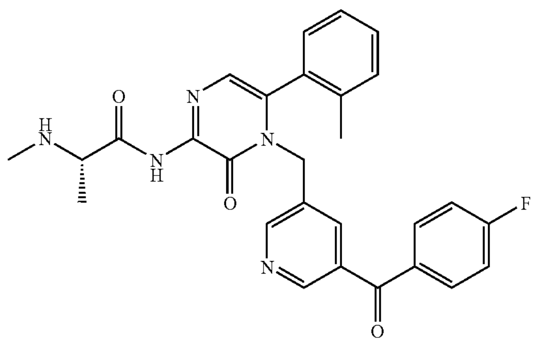 | 76 | (S)-N-{4-[5-(4-Fluoro-benzoyl)-pyridin-3-ylmethyl]-3-oxo-5-o-tolyl-3,4-dihydro-pyrazin-2-yl}-2-methylamino-propionamide | 500.2 |
| 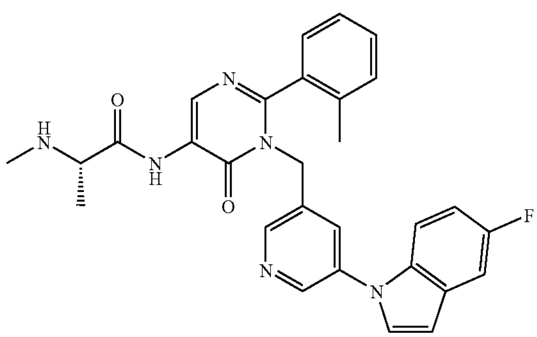 | 77 | (S)-N-{1-[5-(5-Fluoro-indol-1-yl)-pyridin-3-ylmethyl]-6-oxo-2-o-tolyl-1,6-dihydro-pyrimidin-5-yl}-2-methylamino-propionamide | 511.2 |
| 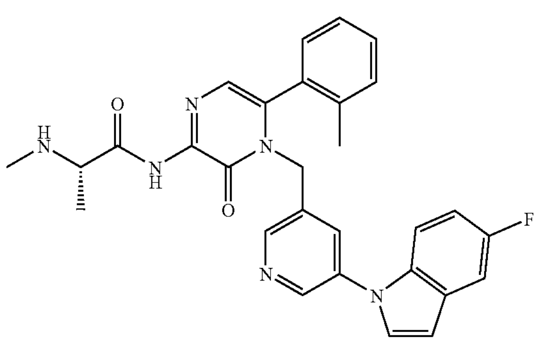 | 78 | (S)-N-{4-[5-(5-Fluoro-indol-1-yl)-pyridin-3-ylmethyl]-3-oxo-5-o-tolyl-3,4-dihydro-pyrazin-2-yl}-2-methylamino-propionamide | 511.2 |

TABLE 2-continued

| Structure | Example No. | name | MS ESI (M + H)+ |
|---|---|---|---|
| 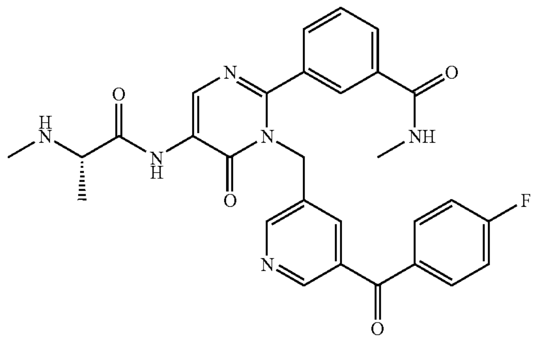 | 79 | 3-[1-[5-(4-Fluoro-benzoyl)-pyridin-3-ylmethyl]-5-((S)-2-methylamino-propionylamino)-6-oxo-1,6-dihydro-pyrimidin-2-yl]-N-methyl-benzamide | 543.2 |
| 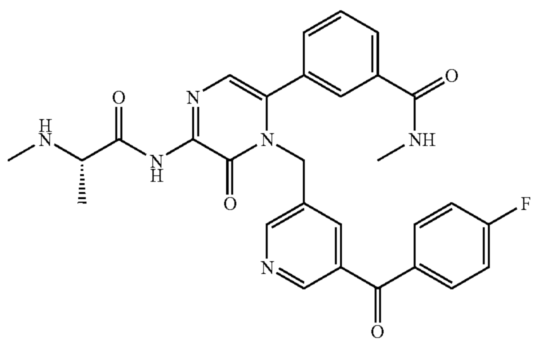 | 80 | 3-[1-[5-(4-Fluoro-benzoyl)-pyridin-3-ylmethyl]-5-((S)-2-methylamino-propionylamino)-6-oxo-1,6-dihydro-pyrazin-2-yl]-N-methyl-benzamide | 543.2 |
| 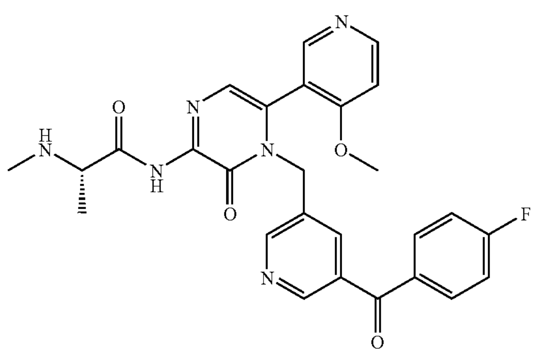 | 81 | (S)-N-[4-[5-(4-Fluoro-benzoyl)-pyridin-3-ylmethyl]-5-(4-methoxy-pyridin-3-yl)-3-oxo-3,4-dihydro-pyrazin-2-yl]-2-methylamino-propionamide | 517.2 |
| 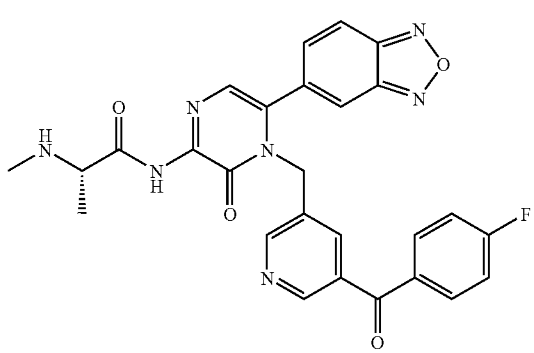 | 82 | (S)-N-{2-Benzo[1,2,5]oxadiazol-5-yl-1-[5-(4-fluoro-benzoyl)-pyridin-3-ylmethyl]-6-oxo-1,6-dihydro-pyrimidin-5-yl}-2-methylamino-propionamide | 528.2 |

TABLE 2-continued

| Structure | Example No. | name | MS ESI (M + H)+ |
|---|---|---|---|
| 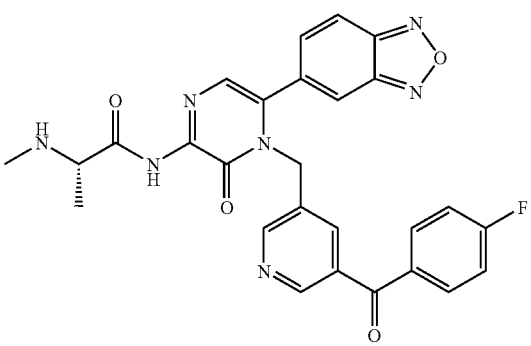 | 83 | (S)-N-{5-Benzo[1,2,5]oxadiazol-5-yl-4-[5-(4-fluoro-benzoyl)-pyridin-3-ylmethyl]-3-oxo-3,4-dihydro-pyrazin-2-yl}-2-methylamino-propionamide | 528.2 |
| 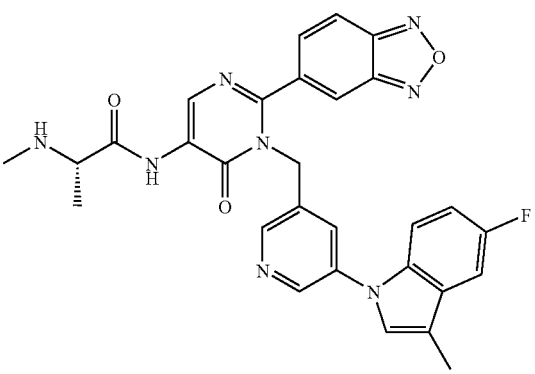 | 84 | (S)-N-{2-Benzo[1,2,5]oxadiazol-5-yl-1-[5-(5-fluoro-3-methyl-indol-1-yl)-pyridin-3-ylmethyl]-6-oxo-1,6-dihydro-pyrimidin-5-yl}-2-methylamino-propionamide | 553.2 |
| 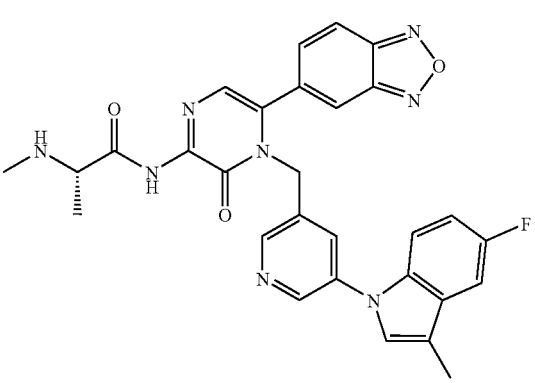 | 85 | (S)-N-{5-Benzo[1,2,5]oxadiazol-5-yl-4-[5-(5-fluoro-3-methyl-indol-1-yl)-pyridin-3-ylmethyl]-3-oxo-3,4-dihydro-pyrazin-2-yl}-2-methylamino-propionamide | 553.2 |
| 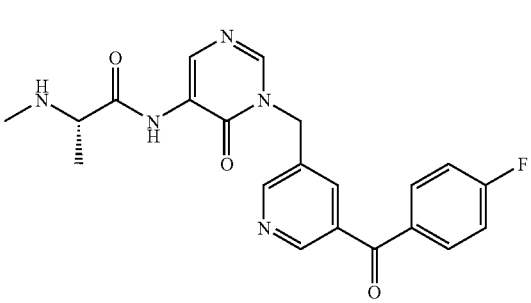 | 86 | (S)-N-{1-[5-(4-Fluoro-benzoyl)-pyridin-3-ylmethyl]-6-oxo-1,6-dihydro-pyrimidin-5-yl}-2-methylamino-propionamide | 410.2 |

TABLE 2-continued

| Structure | Example No. | name | MS ESI (M + H)+ |
|---|---|---|---|
| 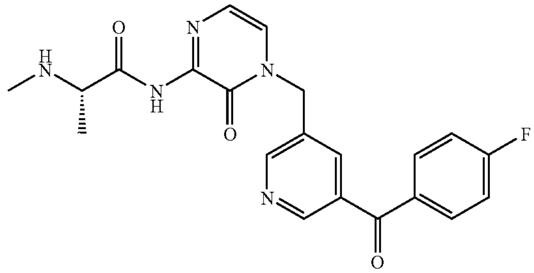 | 87 | (S)-N-{4-[5-(4-Fluoro-benzoyl)-pyridin-3-ylmethyl]-3-oxo-3,4-dihydro-pyrazin-2-yl}-2-methylamino-propionamide | 410.2 |
| 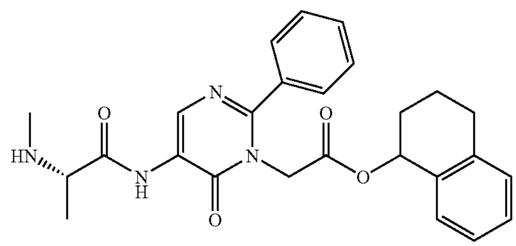 | 88 | [5-((S)-2-Methylamino-propionylamino)-6-oxo-2-phenyl-6H-pyrimidin-1-yl]-acetic acid 1,2,3,4-tetrahydro-naphthalen-1-yl ester | 461.2 |
| 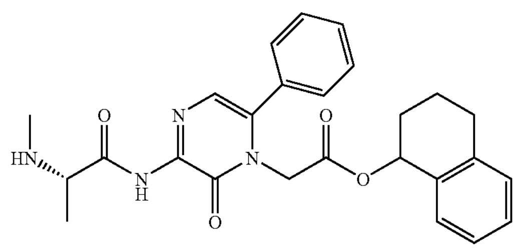 | 89 | [3-((S)-2-Methylamino-propionylamino)-2-oxo-6-phenyl-2H-pyrazin-1-yl]-acetic acid 1,2,3,4-tetrahydro-naphthalen-1-yl ester | 461.2 |
| 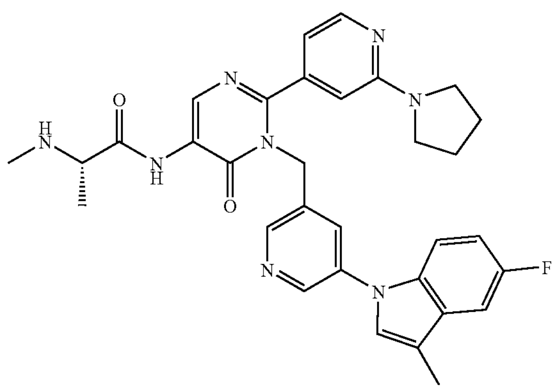 | 90 | (S)-N-[1-[5-(5-Fluoro-3-methyl-indol-1-yl)-pyridin-3-ylmethyl]-6-oxo-2-(2-pyrrolidin-1-yl-pyridin-4-yl)-1,6-dihydro-pyrimidin-5-yl]-2-methylamino-propionamide | 581.3 |
| 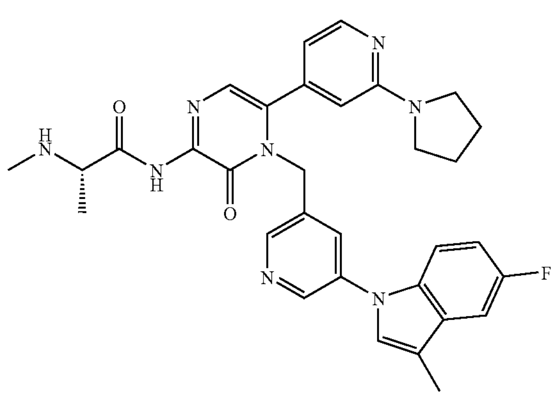 | 91 | (S)-N-[4-[5-(5-Fluoro-3-methyl-indol-1-yl)-pyridin-3-ylmethyl]-3-oxo-5-(2-pyrrolidin-1-yl-pyridin-4-yl)-3,4-dihydro-pyrazin-2-yl]-2-methylamino-propionamide | 581.3 |

TABLE 2-continued

| Structure | Example No. | name | MS ESI (M + H)+ |
|---|---|---|---|
| 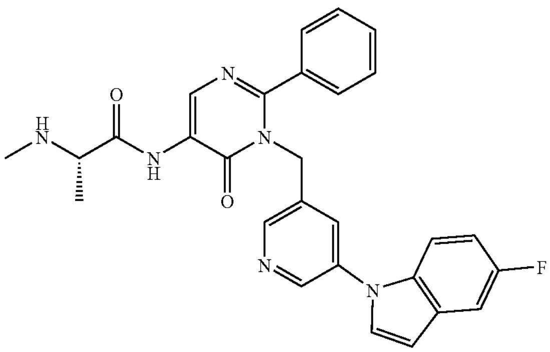 | 92 | (S)-N-{1-[5-(5-Fluoro-indol-1-yl)-pyridin-3-ylmethyl]-6-oxo-2-phenyl-1,6-dihydro-pyrimidin-5-yl}-2-methylamino-propionamide | 497.2 |
| 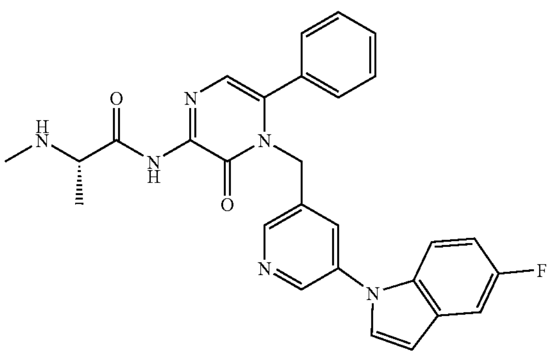 | 93 | (S)-N-{4-[5-(5-Fluoro-indol-1-yl)-pyridin-3-ylmethyl]-3-oxo-5-phenyl-3,4-dihydro-pyrazin-2-yl}-2-methylamino-propionamide | 497.2 |
| 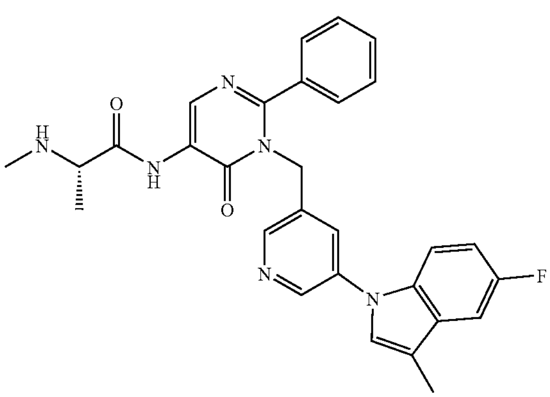 | 94 | (S)-N-{1-[5-(5-Fluoro-3-methyl-indol-1-yl)-pyridin-3-ylmethyl]-6-oxo-2-phenyl-1,6-dihydro-pyrimidin-5-yl}-2-methylamino-propionamide | 511.2 |

TABLE 2-continued

| Structure | Example No. | name | MS ESI (M + H)+ |
|---|---|---|---|
| 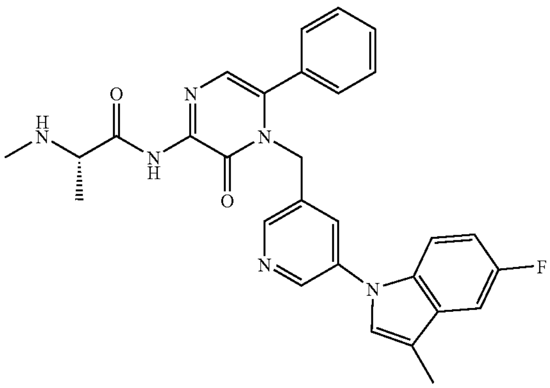 | 95 | (S)-N-{4-[5-(5-Fluoro-3-methyl-indol-1-yl)-pyridin-3-ylmethyl]-3-oxo-5-phenyl-3,4-dihydro-pyrazin-2-yl}-2-methylamino-propionamide | 511.2 |
| 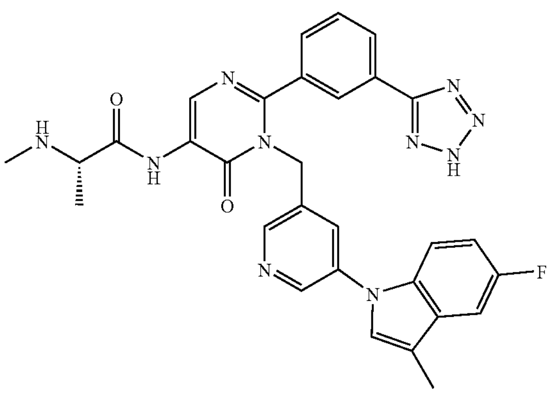 | 96 | (S)-N-{1-[5-(5-Fluoro-3-methyl-indol-1-yl)-pyridin-3-ylmethyl]-6-oxo-2-[3-(2H-tetrazol-5-yl)-phenyl]-1,6-dihydro-pyrimidin-5-yl}-2-methylamino-propionamide | 579.2 |
| 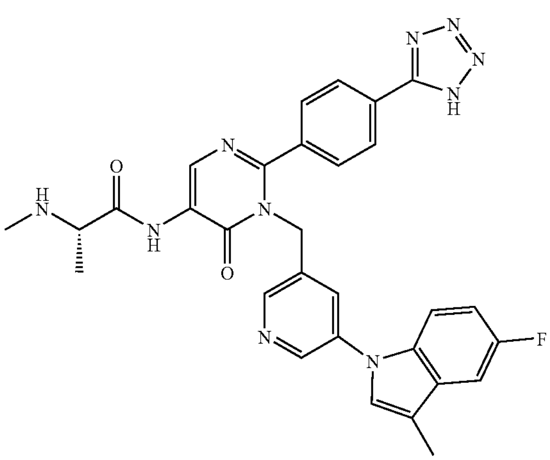 | 97 | (S)-N-{1-[5-(5-Fluoro-3-methyl-indol-1-yl)-pyridin-3-ylmethyl]-6-oxo-2-[4-(1H-tetrazol-5-yl)-phenyl]-1,6-dihydro-pyrimidin-5-yl}-2-methylamino-propionamide | 579.2 |

TABLE 2-continued

| Structure | Example No. | name | MS ESI (M + H)+ |
|---|---|---|---|
| 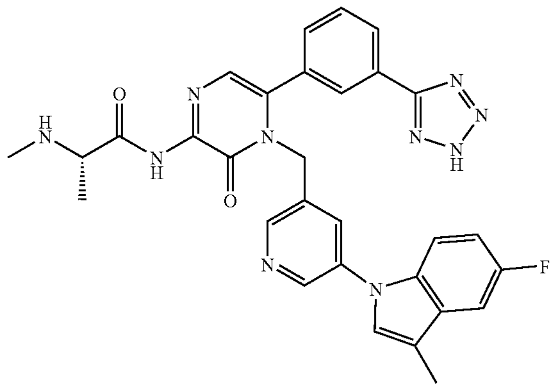 | 98 | (S)-N-{4-[5-(5-Fluoro-3-methyl-indol-1-yl)-pyridin-3-ylmethyl]-3-oxo-5-[3-(2H-tetrazol-5-yl)-phenyl]-3,4-dihydro-pyrazin-2-yl}-2-methylamino-propionamide | 579.2 |
| 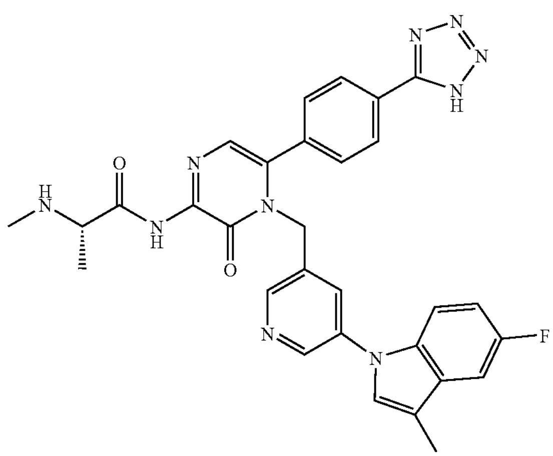 | 99 | (S)-N-{4-[5-(5-Fluoro-3-methyl-indol-1-yl)-pyridin-3-ylmethyl]-3-oxo-5-[4-(1H-tetrazol-5-yl)-phenyl]-3,4-dihydro-pyrazin-2-yl}-2-methylamino-propionamide | 579.2 |
| 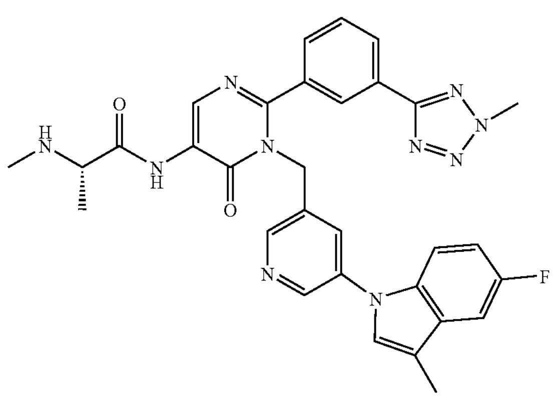 | 100 | (S)-N-{1-[5-(5-Fluoro-3-methyl-indol-1-yl)-pyridin-3-ylmethyl]-2-[3-(2-methyl-2H-tetrazol-5-yl)-phenyl]-6-oxo-1,6-dihydro-pyrimidin-5-yl}-2-methylamino-propionamide | 593.3 |

TABLE 2-continued

| Structure | Example No. | name | MS ESI (M + H)+ |
|---|---|---|---|
| 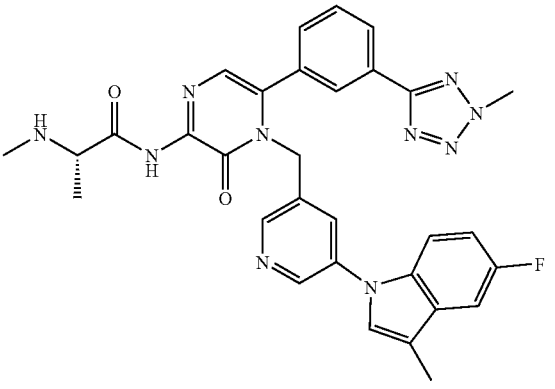 | 101 | (S)-N-{4-[5-(5-Fluoro-3-methyl-indol-1-yl)-pyridin-3-ylmethyl]-5-[3-(2-methyl-2H-tetrazol-5-yl)-phenyl]-3-oxo-3,4-dihydro-pyrazin-2-yl}-2-methylamino-propionamide | 593.3 |
| 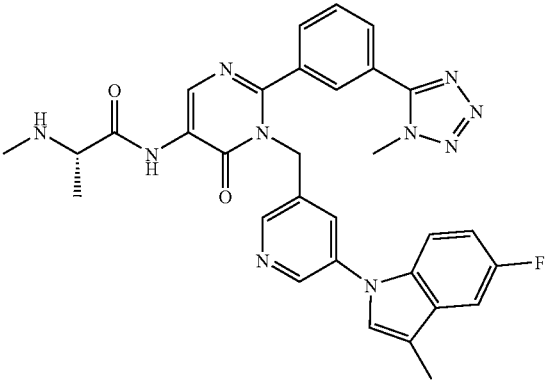 | 102 | (S)-N-{1-[5-(5-Fluoro-3-methyl-indol-1-yl)-pyridin-3-ylmethyl]-2-[3-(1-methyl-1H-tetrazol-5-yl)-phenyl]-6-oxo-1,6-dihydro-pyrimidin-5-yl}-2-methylamino-propionamide | 592.3 |
| 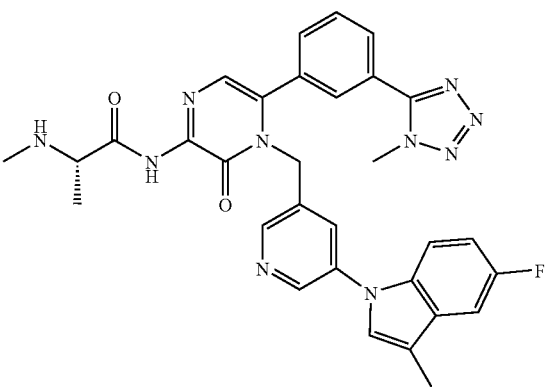 | 103 | (S)-N-{4-[5-(5-Fluoro-3-methyl-indol-1-yl)-pyridin-3-ylmethyl]-5-[3-(1-methyl-1H-tetrazol-5-yl)-phenyl]-3-oxo-3,4-dihydro-pyrazin-2-yl}-2-methylamino-propionamide | 592.3 |
| 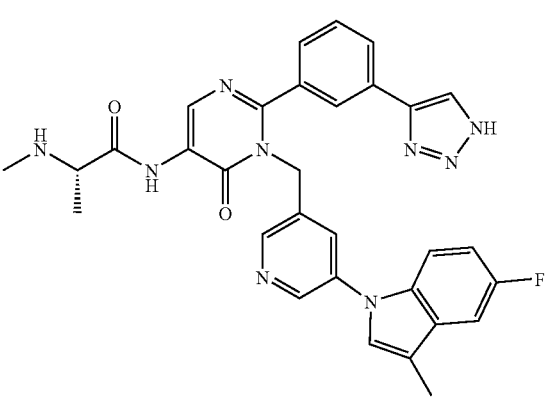 | 104 | (S)-N-{1-[5-(5-Fluoro-3-methyl-indol-1-yl)-pyridin-3-ylmethyl]-6-oxo-2-[3-(1H-[1,2,3]triazol-4-yl)-phenyl]-1,6-dihydro-pyrimidin-5-yl}-2-methylamino-propionamide | 578.2 |

TABLE 2-continued

| Structure | Example No. | name | MS ESI (M + H)+ |
|---|---|---|---|
| 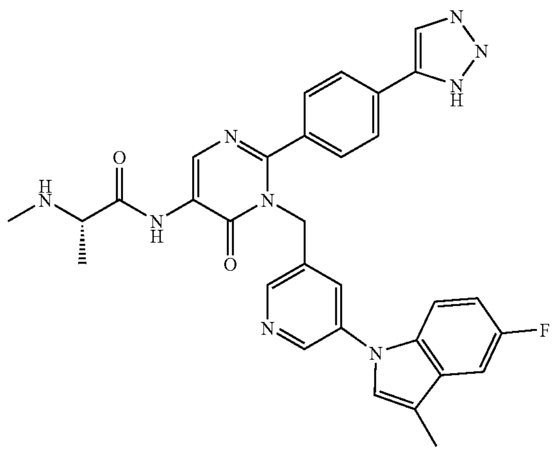 | 105 | (S)-N-{1-[5-(5-Fluoro-3-methyl-indol-1-yl)-pyridin-3-ylmethyl]-6-oxo-2-[4-(3H-[1,2,3]triazol-4-yl)-phenyl]-1,6-dihydro-pyrimidin-5-yl}-2-methylamino-propionamide | 578.2 |
| 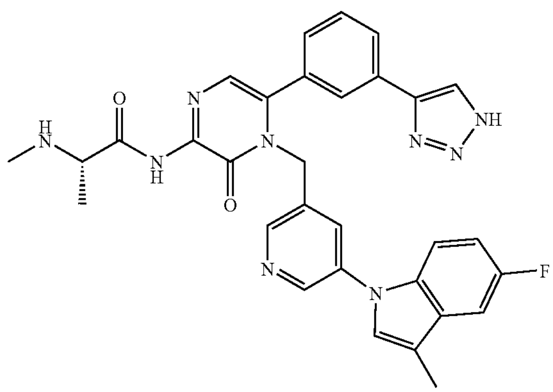 | 106 | (S)-N-{4-[5-(5-Fluoro-3-methyl-indol-1-yl)-pyridin-3-ylmethyl]-3-oxo-5-[3-(1H-[1,2,3]triazol-4-yl)-phenyl]-3,4-dihydro-pyrazin-2-yl}-2-methylamino-propionamide | 578.2 |
| 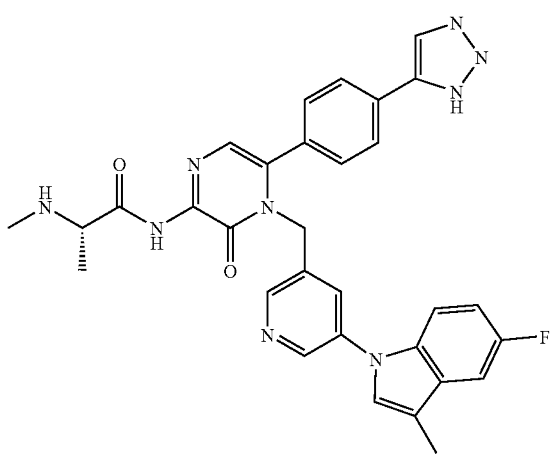 | 107 | (S)-N-{4-[5-(5-Fluoro-3-methyl-indol-1-yl)-pyridin-3-ylmethyl]-3-oxo-5-[4-(3H-[1,2,3]triazol-4-yl)-phenyl]-3,4-dihydro-pyrazin-2-yl}-2-methylamino-propionamide | 578.2 |

TABLE 2-continued

| Structure | Example No. | name | MS ESI (M + H)+ |
|---|---|---|---|
| 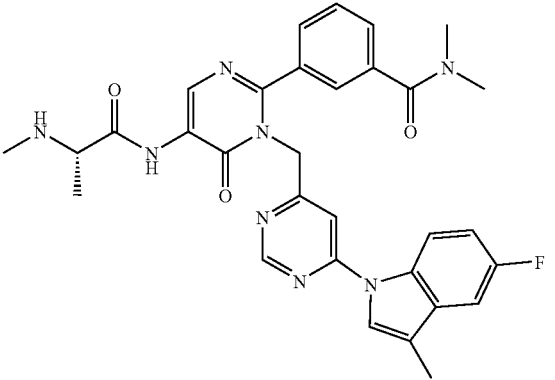 | 108 | 3-[1-[6-(5-Fluoro-3-methyl-indol-1-yl)-2-methyl-pyrimidin-4-ylmethyl]-5-((S)-2-methylamino-propionylamino)-6-oxo-1,6-dihydro-pyrimidin-2-yl]-N,N-dimethyl-benzamide | 597.3 |
| 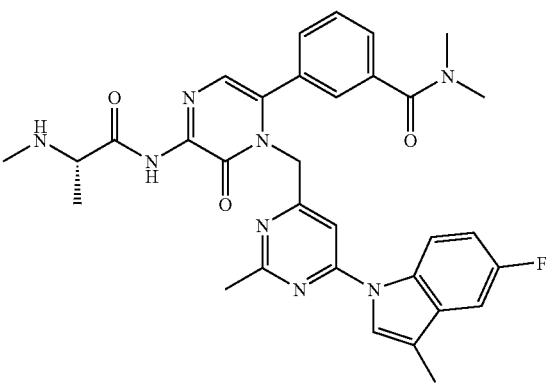 | 109 | 3-[1-[6-(5-Fluoro-3-methyl-indol-1-yl)-2-methyl-pyrimidin-4-ylmethyl]-5-((S)-2-methylamino-propionylamino)-6-oxo-1,6-dihydro-pyrazin-2-yl]-N,N-dimethyl-benzamide | 597.3 |
| 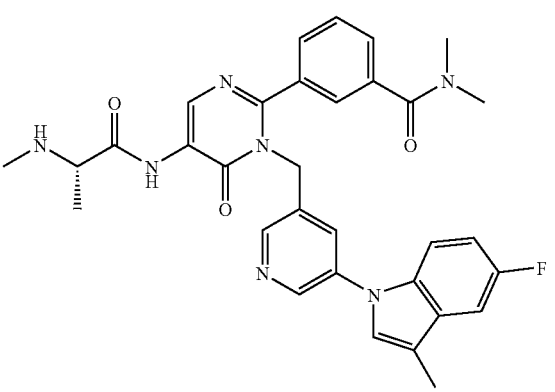 | 110 | 3-[1-[5-(5-Fluoro-3-methyl-indol-1-yl)-pyridin-3-ylmethyl]-5-((S)-2-methylamino-propionylamino)-6-oxo-1,6-dihydro-pyrimidin-2-yl]-N,N-dimethyl-benzamide | 582.3 |
| 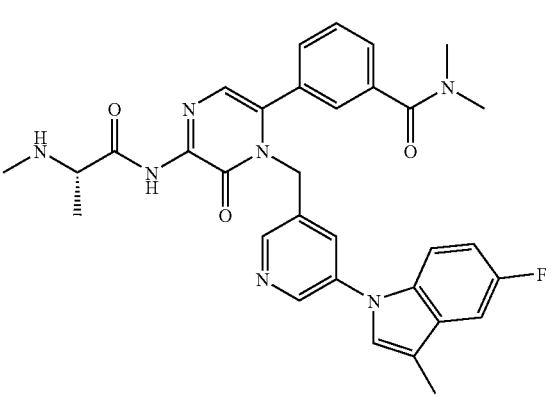 | 111 | 3-[1-[5-(5-Fluoro-3-methyl-indol-1-yl)-pyridin-3-ylmethyl1-5-((S)-2-methylamino-propionylamino)-6-oxo-1,6-dihydro-pyrazin-2-yl]-N,N-dimethyl-benzamide | 582.3 |

TABLE 2-continued

| Structure | Example No. | name | MS ESI (M + H)+ |
|---|---|---|---|
| 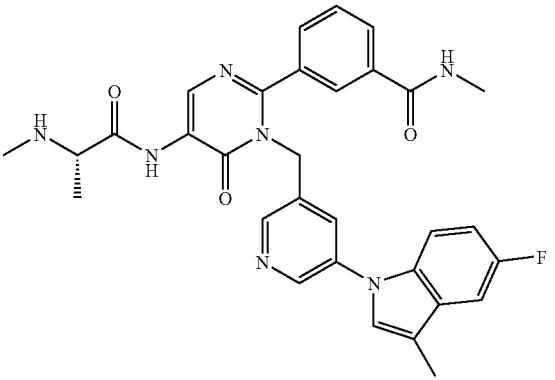 | 112 | 3-[1-[5-(5-Fluoro-3-methyl-indol-1-yl)-pyridin-3-ylmethyl]-5-((S)-2-methylamino-propionylamino)-6-oxo-1,6-dihydro-pyrimidin-2-yl]-N-methyl-benzamide | 568.2 |
| 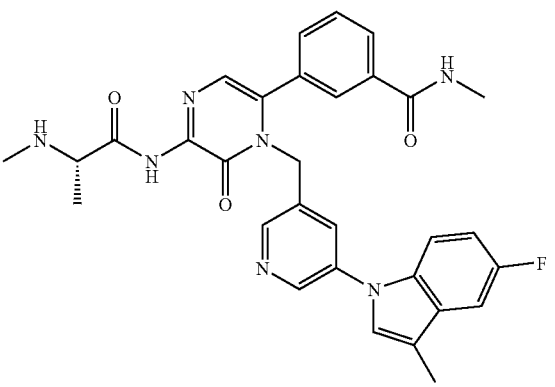 | 113 | 3-[1-[5-(5-Fluoro-3-methyl-indol-1-yl)-pyridin-3-ylmethyl]-5-((S)-2-methylamino-propionylamino)-6-oxo-1,6-dihydro-pyrazin-2-yl]-N-methyl-benzamide | 568.2 |
| 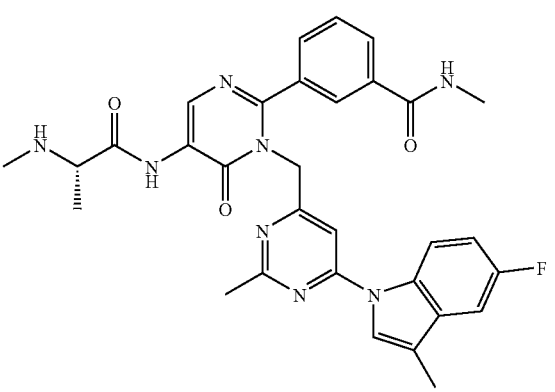 | 114 | 3-[1-[6-(5-Fluoro-3-methyl-indol-1-yl)-2-methyl-pyrimidin-4-ylmethyl]-5-((S)-2-methylamino-propionylamino)-6-oxo-1,6-dihydro-pyrimidin-2-yl]-N-methyl-benzamide | 583.3 |
| 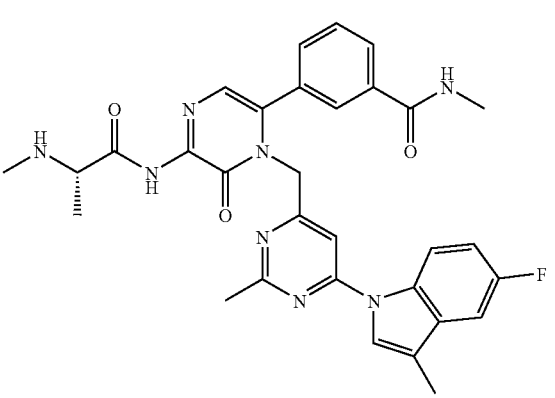 | 115 | 3-[1-[6-(5-Fluoro-3-methyl-indol-1-yl)-2-methyl-pyrimidin-4-ylmethyl]-5-((S)-2-methylamino-propionylamino)-6-oxo-1,6-dihydro-pyrazin-2-yl]-N-methyl-benzamide | 583.3 |

TABLE 2-continued

| Structure | Example No. | name | MS ESI (M + H)+ |
|---|---|---|---|
| 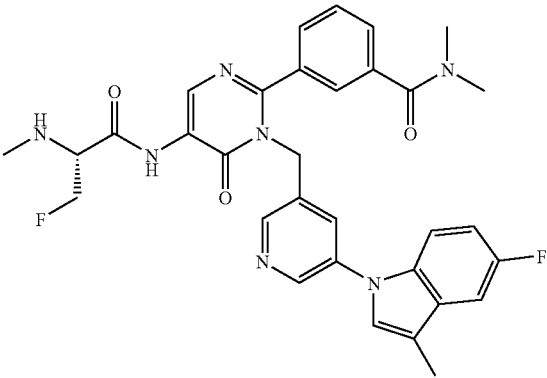 | 116 | 3-{5-((R)-3-Fluoro-2-methylamino-propionylamino)-1-[5-(5-fluoro-3-methyl-indol-1-yl)-pyridin-3-ylmethyl]-6-oxo-1,6-dihydro-pyrimidin-2-yl}-N,N-dimethyl-benzamide | 600.2 |
| 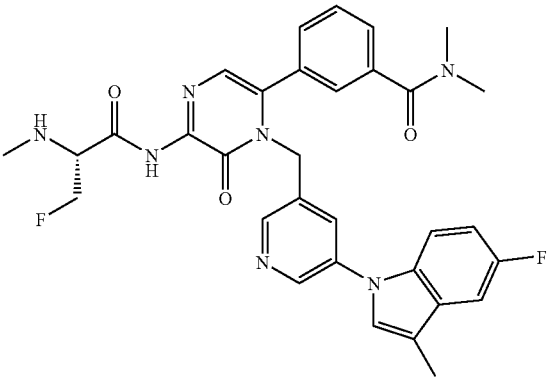 | 117 | 3-{5-((R)-3-Fluoro-2-methylamino-propionylamino)-1-[5-(5-fluoro-3-methyl-indol-1-yl)-pyridin-3-ylmethyl]-6-oxo-1,6-dihydro-pyrazin-2-yl}-N,N-dimethyl-benzamide | 600.2 |
| 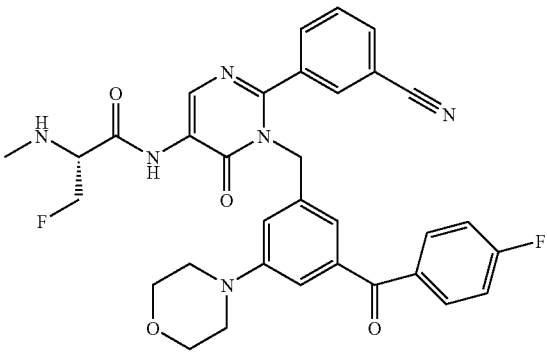 | 118 | (R)-N-{2-(3-Cyano-phenyl)-1-[3-(4-fluoro-benzoyl)-5-morpholin-4-yl-benzyl]-6-oxo-1,6-dihydro-pyrimidin-5-yl}-3-fluoro-2-methylamino-propionamide | 613.2 |
| 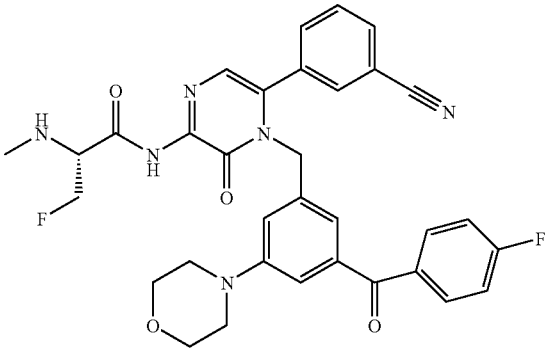 | 119 | (R)-N-{5-(3-Cyano-phenyl)-4-[3-(4-fluoro-benzoyl)-5-morpholin-4-yl-benzyl]-3-oxo-3,4-dihydro-pyrazin-2-yl}-3-fluoro-2-methylamino-propionamide | 613.2 |

TABLE 2-continued

| Structure | Example No. | name | MS ESI (M + H)+ |
|---|---|---|---|
| 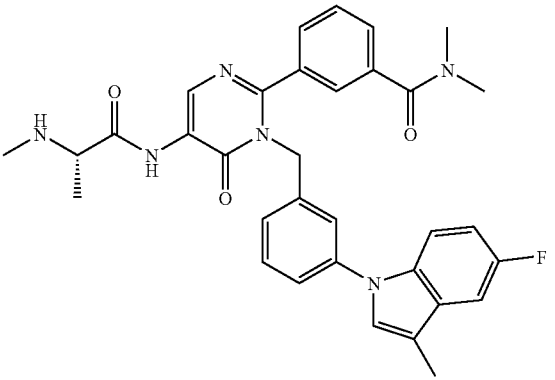 | 120 | 3-[1-[3-(5-Fluoro-3-methyl-indol-1-yl)-benzyl]-5-((S)-2-methylamino-propionylamino)-6-oxo-1,6-dihydro-pyrimidin-2-yl]-N,N-dimethyl-benzamide | 581.3 |
| 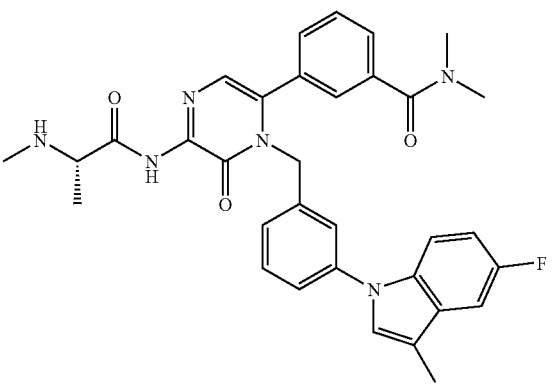 | 121 | 3-[1-[3-(5-Fluoro-3-methyl-indol-1-yl)-benzyl]-5-((S)-2-methylamino-propionylamino)-6-oxo-1,6-dihydro-pyrazin-2-yl]-N,N-dimethyl-benzamide | 581.3 |
| 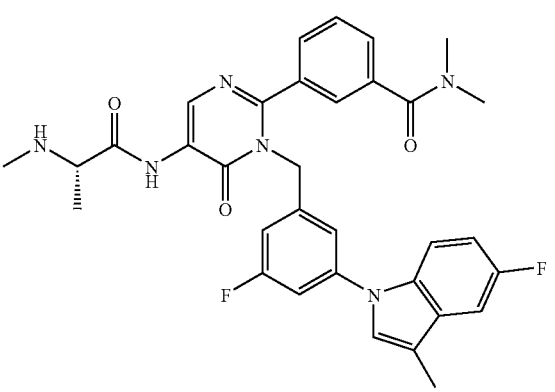 | 122 | 3-[1-[3-Fluoro-5-(5-fluoro-3-methyl-indol-1-yl)-benzyl]-5-((S)-2-methylamino-propionylamino)-6-oxo-1,6-dihydro-pyrimidin-2-yl]-N,N-dimethyl-benzamide | 599.3 |
| 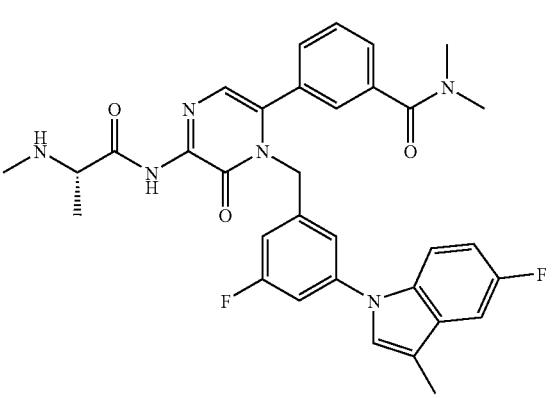 | 123 | 3-[1-[3-Fluoro-5-(5-fluoro-3-methyl-indol-1-yl)-benzyl]-5-((S)-2-methylamino-propionylamino)-6-oxo-1,6-dihydro-pyrazin-2-yl]-N,N-dimethyl-benzamide | 599.3 |

TABLE 2-continued

| Structure | Example No. | name | MS ESI (M + H)+ |
|---|---|---|---|
| 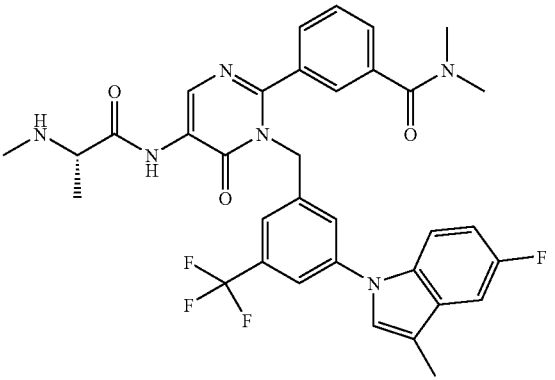 | 124 | 3-[1-[3-Trifluoromethyl-5-(5-fluoro-3-methyl-indol-1-yl)-benzyl]-5-((S)-2-methylamino-propionylamino)-6-oxo-1,6-dihydro-pyrimidin-2-yl]-N,N-dimethyl-benzamide | 649.3 |
| 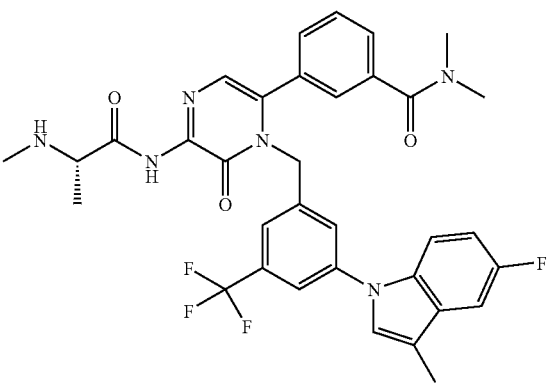 | 125 | 3-[1-[3-Trifluoromethyl-5-(5-fluoro-3-methyl-indol-1-yl)-benzyl]-5-((S)-2-methylamino-propionylamino)-6-oxo-1,6-dihydro-pyrazin-2-yl]-N,N-dimethyl-benzamide | 649.3 |
| 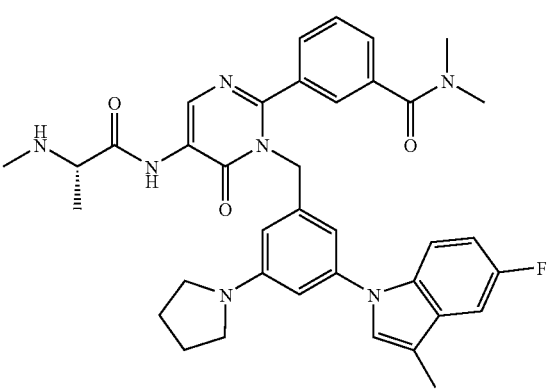 | 126 | 3-[1-[3-(5-Fluoro-3-methyl-indol-1-yl)-5-pyrrolidin-1-yl-benzyl]-5-((S)-2-methylamino-propionylamino)-6-oxo-1,6-dihydro-pyrimidin-2-yl]-N,N-dimethyl-benzamide | 650.3 |
| 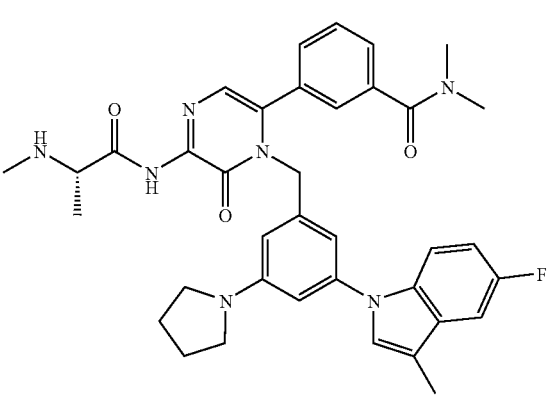 | 127 | 3-[1-[3-(5-Fluoro-3-methyl-indol-1-yl)-5-pyrrolidin-1-yl-benzyl]-5-((S)-2-methylamino-propionylamino)-6-oxo-1,6-dihydro-pyrazin-2-yl]-N,N-dimethyl-benzamide | 650.3 |

TABLE 2-continued

| Structure | Example No. | name | MS ESI (M + H)+ |
|---|---|---|---|
| 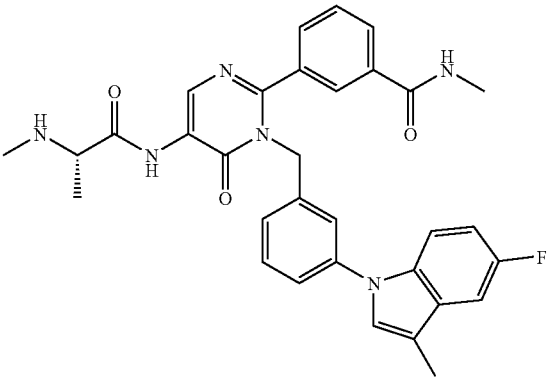 | 128 | 3-[1-[3-(5-Fluoro-3-methyl-indol-1-yl)-benzyl]-5-((S)-2-methylamino-propionylamino)-6-oxo-1,6-dihydro-pyrimidin-2-yl]-N-methyl-benzamide | 567.2 |
| 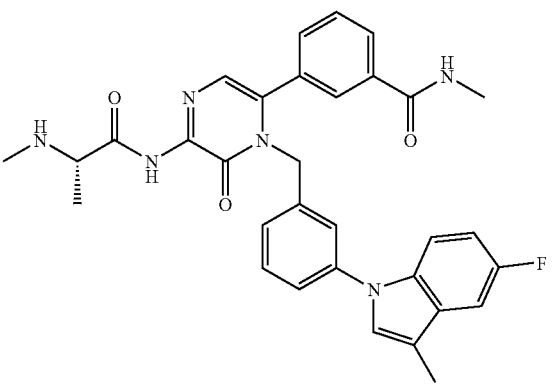 | 129 | 3-[1-[3-(5-Fluoro-3-methyl-indol-1-yl)-benzyl]-5-((S)-2-methylamino-propionylamino)-6-oxo-1,6-dihydro-pyrazin-2-yl]-N-methyl-benzamide | 567.2 |
| 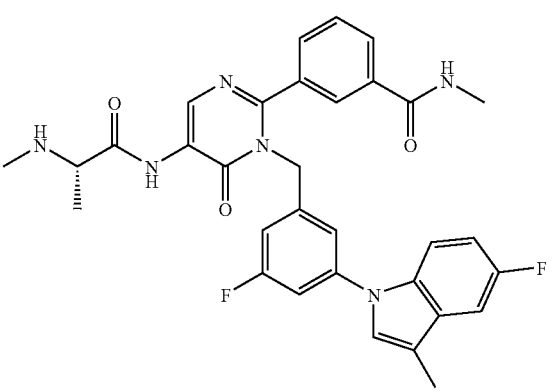 | 130 | 3-[1-[3-Fluoro-5-(5-fluoro-3-methyl-indol-1-yl)-benzyl]-5-((S)-2-methylamino-propionylamino)-6-oxo-1,6-dihydro-pyrimidin-2-yl]-N-methyl-benzamide | 585.2 |
| 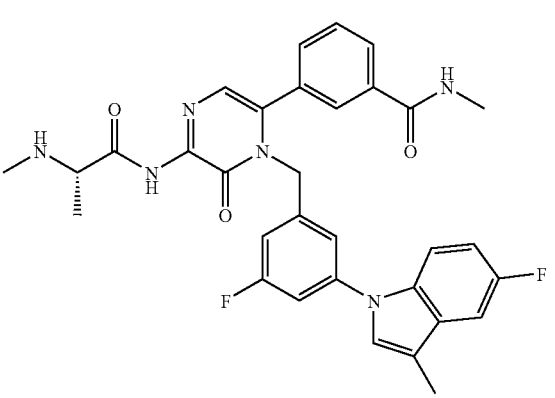 | 131 | 3-[1-[3-Fluoro-5-(5-fluoro-3-methyl-indol-1-yl)-benzyl]-5-((S)-2-methylamino-propionylamino)-6-oxo-1,6-dihydro-pyrazin-2-yl]-N-methyl-benzamide | 585.2 |

TABLE 2-continued

| Structure | Example No. | name | MS ESI (M + H)+ |
|---|---|---|---|
| 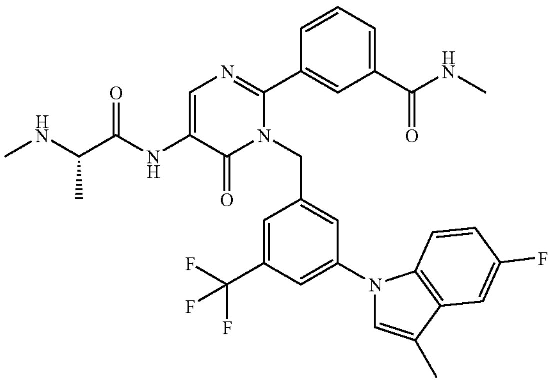 | 132 | 3-[1-[3-Trifluoromethyl-5-(5-fluoro-3-methyl-indol-1-yl)-benzyl]-5-((S)-2-methylamino-propionylamino)-6-oxo-1,6-dihydro-pyrimidin-2-yl]-N-methyl-benzamide | 635.2 |
| 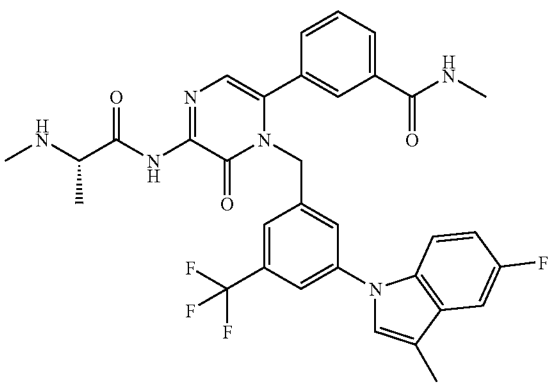 | 133 | 3-[1-[3-Trifluoromethyl-5-(5-fluoro-3-methyl-indol-1-yl)-benzyl]-5-((S)-2-methylamino-propionylamino)-6-oxo-1,6-dihydro-pyrazin-2-yl]-N-methyl-benzamide | 635.2 |
| 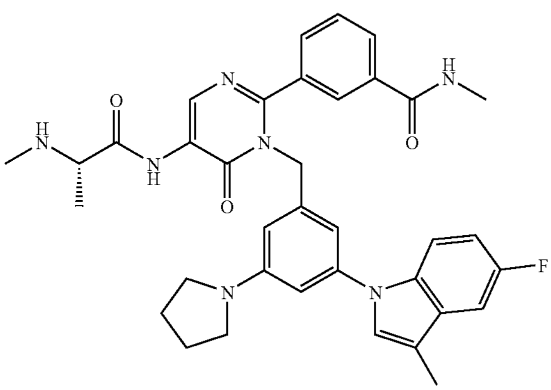 | 134 | 3-[1-[3-(5-Fluoro-3-methyl-indol-1-yl)-5-pyrrolidin-1-yl-benzyl]-5-((S)-2-methylamino-propionylamino)-6-oxo-1,6-dihydro-pyrimidin-2-yl]-N-methyl-benzamide | 636.3 |
| 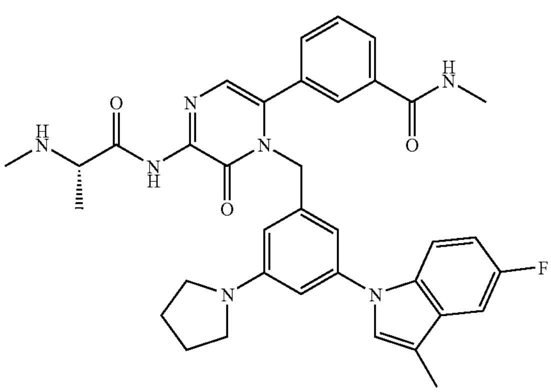 | 135 | 3-[1-[3-(5-Fluoro-3-methyl-indol-1-yl)-5-pyrrolidin-1-yl-benzyl]-5-((S)-2-methylamino-propionylamino)-6-oxo-1,6-dihydro-pyrazin-2-yl]-N-methyl-benzamide | 636.3 |

TABLE 2-continued

| Structure | Example No. | name | MS ESI (M + H)+ |
|---|---|---|---|
| 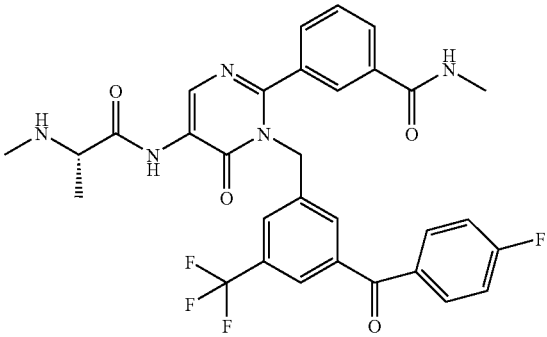 | 136 | 3-[1-[3-(4-Fluoro-benzoyl)-5-trifluoromethyl-benzyl]-5-((S)-2-methylamino-propionylamino)-6-oxo-1,6-dihydro-pyrimidin-2-yl]-N-methyl-benzamide | 610.2 |
| 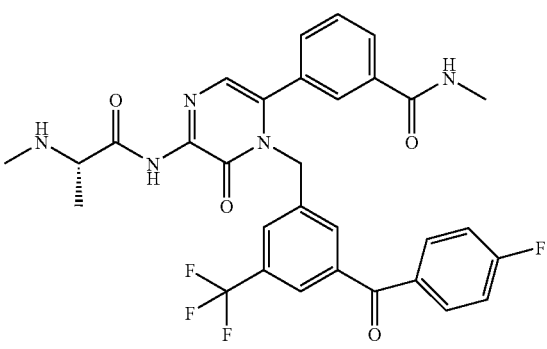 | 137 | 3-[1-[3-(4-Fluoro-benzoyl)-5-trifluoromethyl-yl-benzyl]-5-((S)-2-methylamino-propionylamino)-6-oxo-1,6-dihydro-pyrazin-2-yl]-N-methyl-benzamide | 610.2 |
| 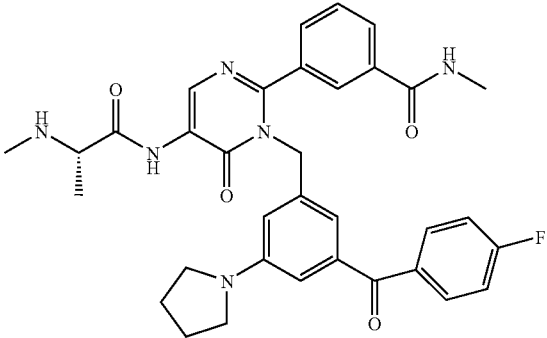 | 138 | 3-[1-[3-(4-Fluoro-benzoyl)-5-pyrrolidin-1-yl-benzyl]-5-((S)-2-methylamino-propionylamino)-6-oxo-1,6-dihydro-pyrimidin-2-yl]-N-methyl-benzamide | 611.3 |
| 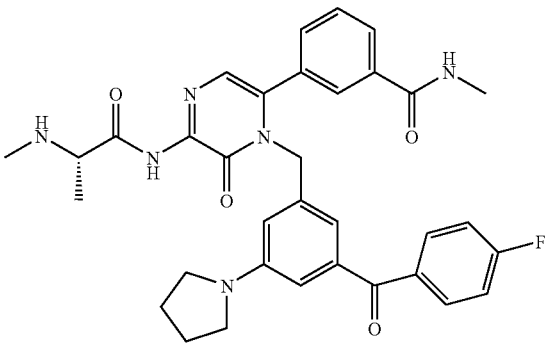 | 139 | 3-[1-[3-(4-Fluoro-benzoyl)-5-pyrrolidin-1-yl-benzyl]-5-((S)-2-methylamino-propionylamino)-6-oxo-1,6-dihydro-pyrazin-2-yl]-N-methyl-benzamide | 611.3 |

TABLE 2-continued

| Structure | Example No. | name | MS ESI (M + H)+ |
|---|---|---|---|
| 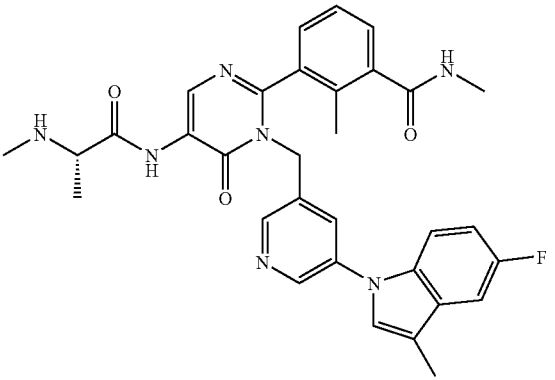 | 140 | 3-[1-[5-(5-Fluoro-3-methyl-indol-1-yl)-pyridin-3-ylmethyl]-5-((S)-2-methylamino-propionylamino)-6-oxo-1,6-dihydro-pyrimidin-2-yl]-2,N-dimethyl-benzamide | 582.3 |
| 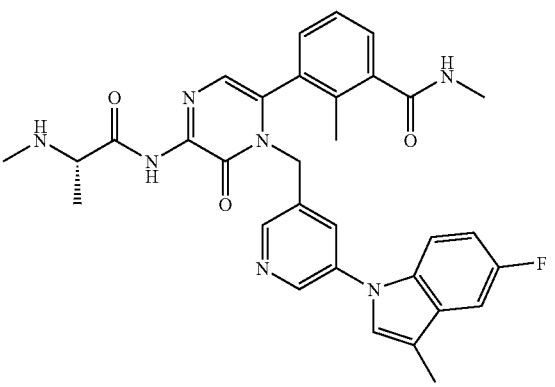 | 141 | 3-[1-[5-(5-Fluoro-3-methyl-indol-1-yl)-pyridin-3-ylmethyl]-5-((S)-2-methylamino-propionylamino)-6-oxo-1,6-dihydro-pyrazin-2-yl]-2,N-dimethyl-benzamide | 582.3 |
| 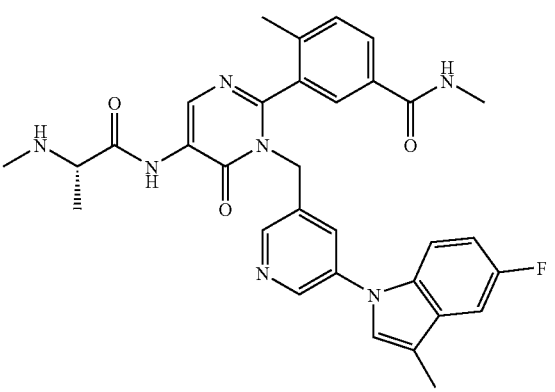 | 142 | 3-[1-[5-(5-Fluoro-3-methyl-indol-1-yl)-pyridin-3-ylmethyl]-5-((S)-2-methylamino-propionylamino)-6-oxo-1,6-dihydro-pyrimidin-2-yl]-4,N-dimethyl-benzamide | 582.3 |
| 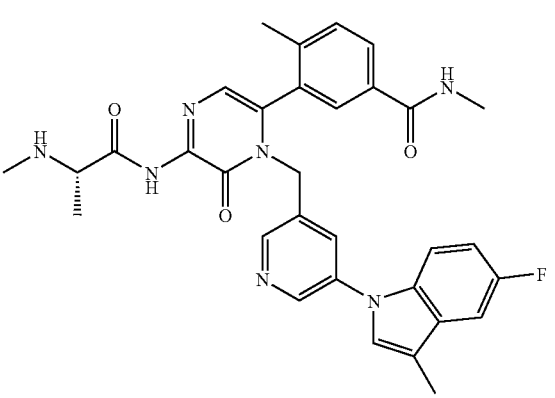 | 143 | 3-[1-[5-(5-Fluoro-3-methyl-indol-1-yl)-pyridin-3-ylmethyl]-5-((S)-2-methylamino-propionylamino)-6-oxo-1,6-dihydro-pyrazin-2-yl]-4,N-dimethyl-benzamide | 582.3 |

TABLE 2-continued

| Structure | Example No. | name | MS ESI (M + H)+ |
|---|---|---|---|
| 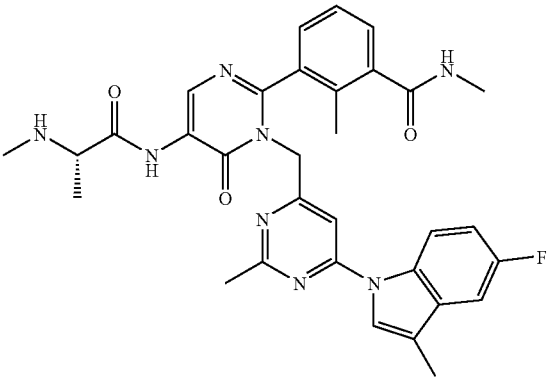 | 144 | 3-[1-[6-(5-Fluoro-3-methyl-indol-1-yl)-2-methyl-pyrimidin-4-ylmethyl]-5-((S)-2-methylamino-propionylamino)-6-oxo-1,6-dihydro-pyrimidin-2-yl]-2,N-dimethyl-benzamide | 597.3 |
| 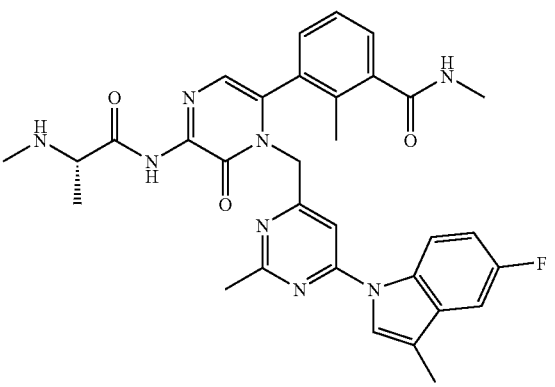 | 145 | 3-[1-[6-(5-Fluoro-3-methyl-indol-1-yl)-2-methyl-pyrimidin-4-ylmethyl]-5-((S)-2-methylamino-propionylamino)-6-oxo-1,6-dihydro-pyrazin-2-yl]-2,N-dimethyl-benzamide | 597.3 |
| 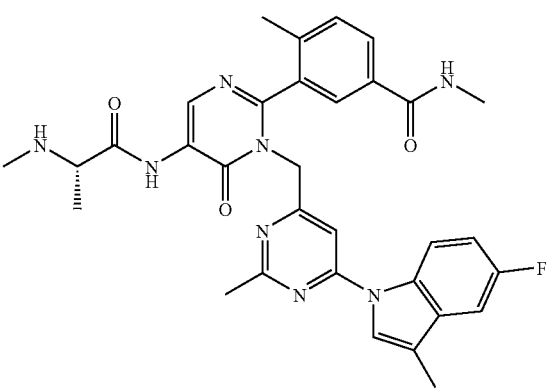 | 146 | 3-[1-[6-(5-Fluoro-3-methyl-indol-1-yl)-2-methyl-pyrimidin-4-ylmethyl]-5-((S)-2-methylamino-propionylamino)-6-oxo-1,6-dihydro-pyrimidin-2-yl]-4,N-dimethyl-benzamide | 597.3 |
| 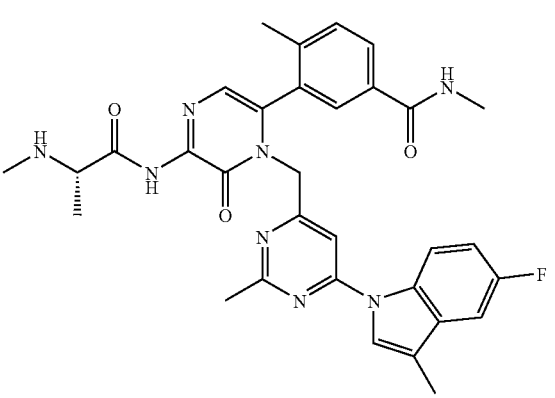 | 147 | 3-[1-[6-(5-Fluoro-3-methyl-indol-1-yl)-2-methyl-pyrimidin-4-ylmethyl]-5-((S)-2-methylamino-propionylamino)-6-oxo-1,6-dihydro-pyrazin-2-yl]-4,N-dimethyl-benzamide | 597.3 |

TABLE 2-continued

| Structure | Example No. | name | MS ESI (M + H)+ |
|---|---|---|---|
| 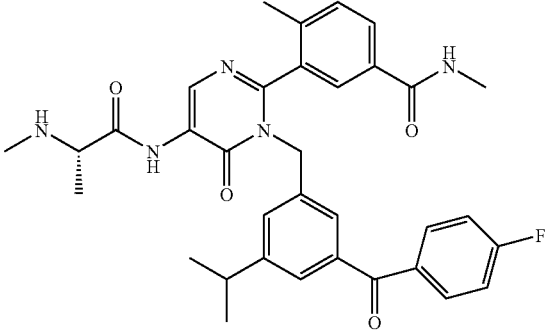 | 148 | 3-[1-[3-(4-Fluoro-benzoyl)-5-isopropyl-benzyl]-5-((S)-2-methylamino-propionylamino)-6-oxo-1,6-dihydro-pyrimidin-2-yl]-4,N-dimethyl-benzamide | 598.3 |
| 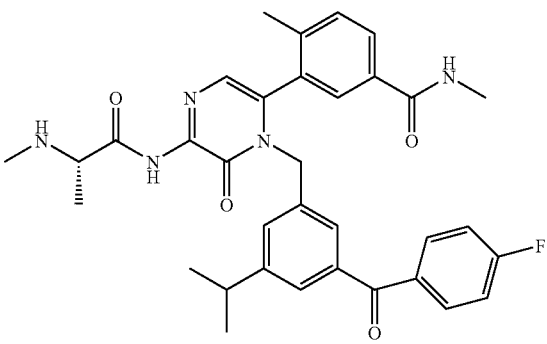 | 149 | 3-[1-[3-(4-Fluoro-benzoyl)-5-isopropyl-benzyl]-5-((S)-2-methylamino-propionylamino)-6-oxo-1,6-dihydro-pyrazin-2-yl]-4,N-dimethyl-benzamide | 598.3 |
| 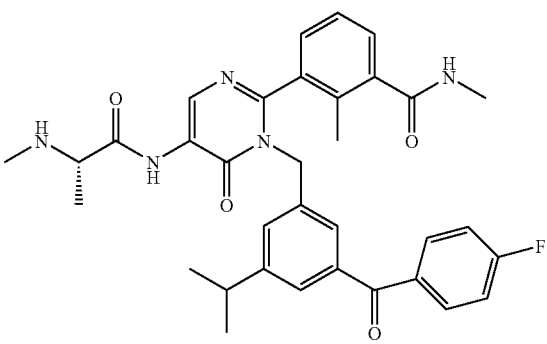 | 150 | 3-[1-[3-(4-Fluoro-benzoyl)-5-isopropyl-benzyl]-5-((S)-2-methylamino-propionylamino)-6-oxo-1,6-dihydro-pyrimidin-2-yl]-2,N-dimethyl-benzamide | 597.3 |
| 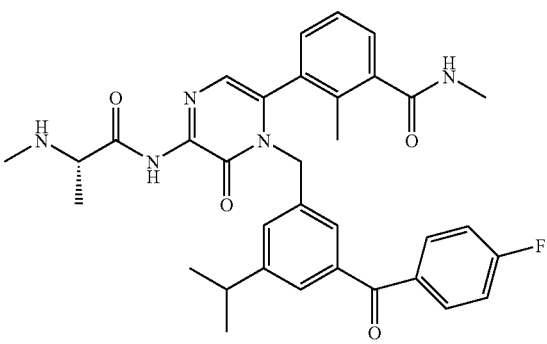 | 151 | 3-[1-[3-(4-Fluoro-benzoyl)-5-isopropyl-benzyl]-5-((S)-2-methylamino-propionylamino)-6-oxo-1,6-dihydro-pyrazin-2-yl]-2,N-dimethyl-benzamide | 597.3 |

TABLE 2-continued

| Structure | Example No. | name | MS ESI (M + H)+ |
|---|---|---|---|
| 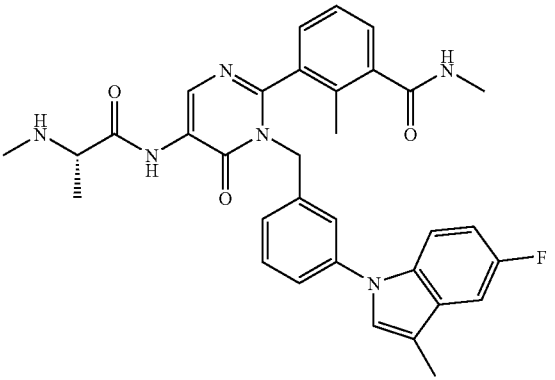 | 152 | 3-[1-[3-(5-Fluoro-3-methyl-indol-1-yl)-benzyl]-5-((S)-2-methylamino-propionylamino)-6-oxo-1,6-dihydro-pyrimidin-2-yl]-2,N-dimethyl-benzamide | 581.3 |
| 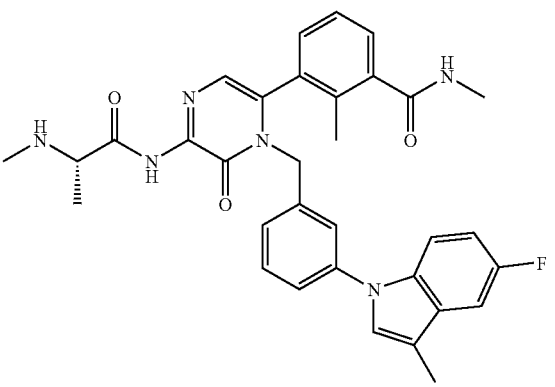 | 153 | 3-[1-[3-(5-Fluoro-3-methyl-indol-1-yl)-benzyl]-5-((S)-2-methylamino-propionylamino)-6-oxo-1,6-dihydro-pyrazin-2-yl]-2,N-dimethyl-benzamide | 581.3 |
| 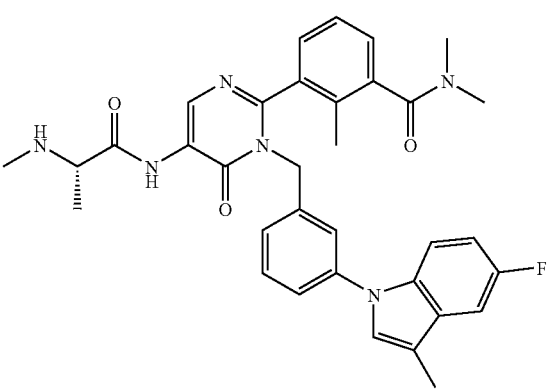 | 154 | 3-[1-[3-(5-Fluoro-3-methyl-indol-1-yl)-benzyl]-5-((S)-2-methylamino-propionylamino)-6-oxo-1,6-dihydro-pyrimidin-2-yl]-2,N,N-trimethyl-benzamide | 595.3 |
| 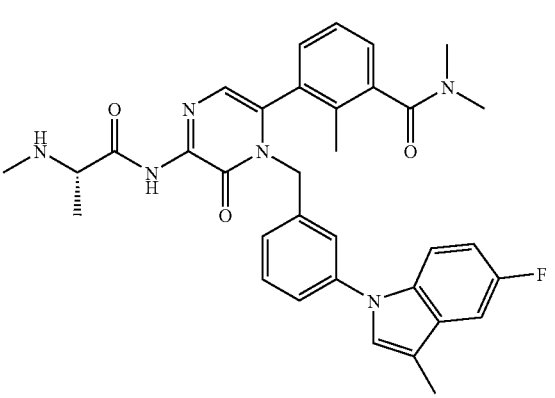 | 155 | 3-[1-[3-(5-Fluoro-3-methyl-indol-1-yl)-benzyl]-5-((S)-2-methylamino-propionylamino)-6-oxo-1,6-dihydro-pyrazin-2-yl]-2,N,N-trimethyl-benzamide | 595.3 |

TABLE 2-continued

| Structure | Example No. | name | MS ESI (M + H)+ |
|---|---|---|---|
| 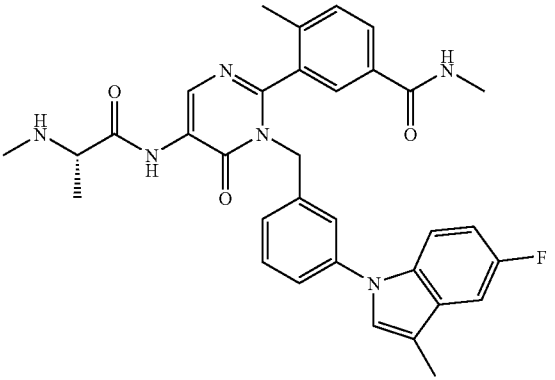 | 156 | 3-[1-[3-(5-Fluoro-3-methyl-indol-1-yl)-benzyl]-5-((S)-2-methylamino-propionylamino)-6-oxo-1,6-dihydro-pyrimidin-2-yl]-4,N-dimethyl-benzamide | 581.3 |
| 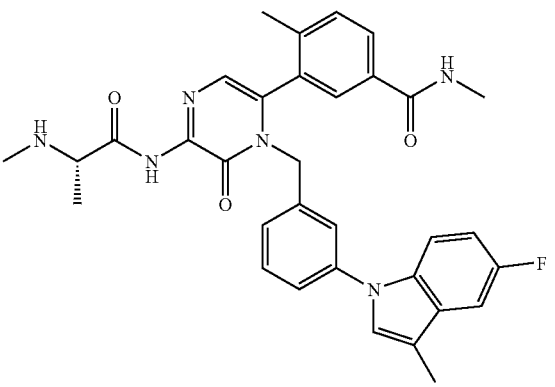 | 157 | 3-[1-[3-(5-Fluoro-3-methyl-indol-1-yl)-benzyl]-5-((S)-2-methylamino-propionylamino)-6-oxo-1,6-dihydro-pyrazin-2-yl]-4,N-dimethyl-benzamide | 581.3 |
| 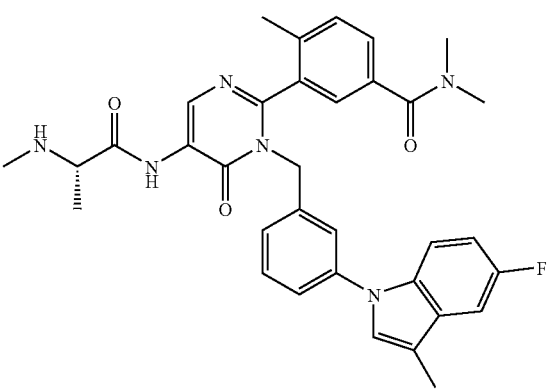 | 158 | 3-[1-[3-(5-Fluoro-3-methyl-indol-1-yl)-benzyl]-5-((S)-2-methylamino-propionylamino)-6-oxo-1,6-dihydro-pyrimidin-2-yl]-4,N,N-trimethyl-benzamide | 595.3 |
| 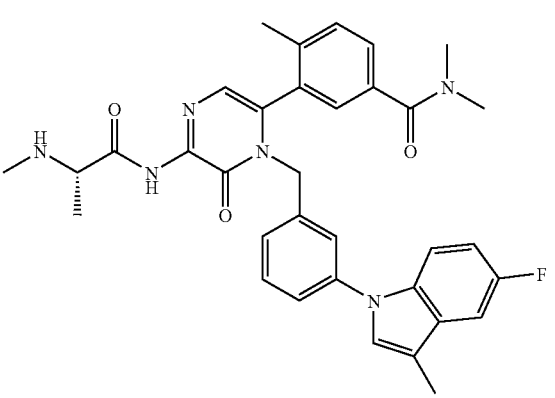 | 159 | 3-[1-[3-(5-Fluoro-3-methyl-indol-1-yl)-benzyl]-5-((S)-2-methylamino-propionylamino)-6-oxo-1,6-dihydro-pyrazin-2-yl]-4,N,N-trimethyl-benzamide | 595.3 |

TABLE 2-continued

| Structure | Example No. | name | MS ESI (M + H)+ |
|---|---|---|---|
| 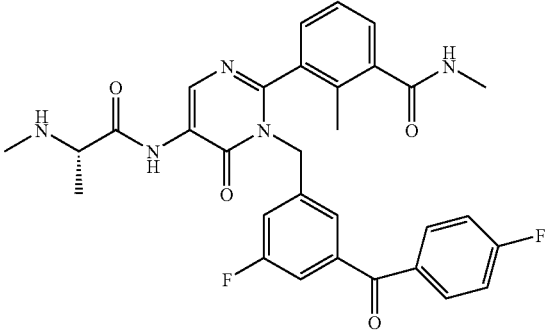 | 160 | 3-[1-[3-Fluoro-5-(4-fluoro-benzoyl)-benzyl]-5-((S)-2-methylamino-propionylamino)-6-oxo-1,6-dihydro-pyrimidin-2-yl]-2,N-dimethyl-benzamide | 574.2 |
| 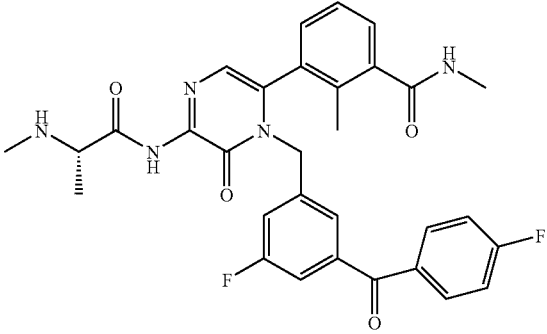 | 161 | 3-[1-[3-Fluoro-5-(4-fluoro-benzoyl)-benzyl]-5-((S)-2-methylamino-propionylamino)-6-oxo-1,6-dihydro-pyrazin-2-yl]-2,N-dimethyl-benzamide | 574.2 |
| 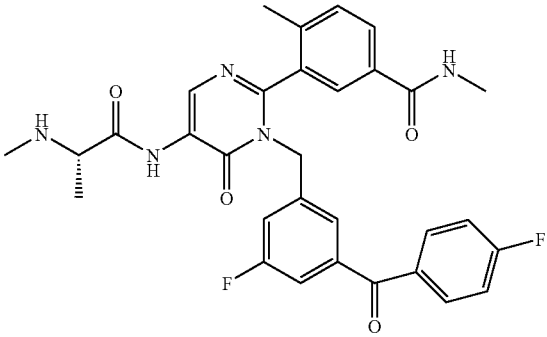 | 162 | 3-[1-[3-Fluoro-5-(4-fluoro-benzoyl)-benzyl]-5-((S)-2-methylamino-propionylamino)-6-oxo-1,6-dihydro-pyrimidin-2-yl]-4,N-dimethyl-benzamide | 574.2 |
| 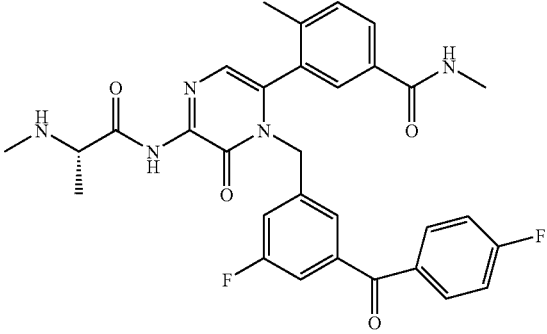 | 163 | 3-[1-[3-Fluoro-5-(4-fluoro-benzoyl)-benzyl]-5-((S)-2-methylamino-propionylamino)-6-oxo-1,6-dihydro-pyrazin-2-yl]-4,N-dimethyl-benzamide | 574.2 |

TABLE 2-continued

| Structure | Example No. | name | MS ESI (M + H)+ |
|---|---|---|---|
| 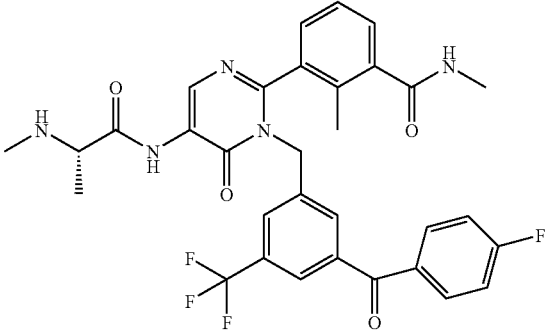 | 164 | 3-[1-[3-Trifluoromethyl-5-(4-fluoro-benzoyl)-benzyl]-5-((S)-2-methylamino-propionylamino)-6-oxo-1,6-dihydro-pyrimidin-2-yl]-2,N-dimethyl-benzamide | 624.2 |
| 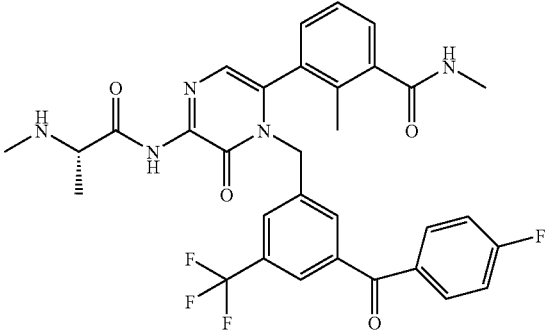 | 165 | 3-[1-[3-Trifluoromethyl-5-(4-fluoro-benzoyl)-benzyl]-5-((S)-2-methylamino-propionylamino)-6-oxo-1,6-dihydro-pyrazin-2-yl]-2,N-dimethyl-benzamide | 624.2 |
| 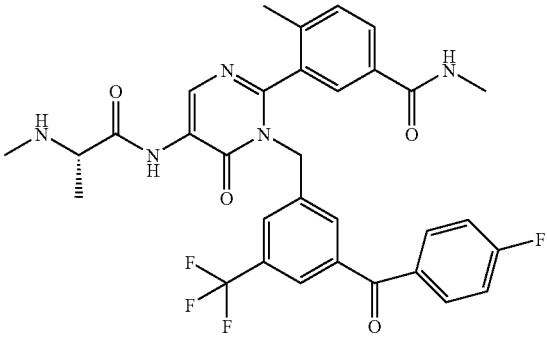 | 166 | 3-[1-[3-Trifluoromethyl-5-(4-fluoro-benzoyl)-benzyl]-5-((S)-2-methylamino-propionylamino)-6-oxo-1,6-dihydro-pyrimidin-2-yl]-4,N-dimethyl-benzamide | 624.2 |
| 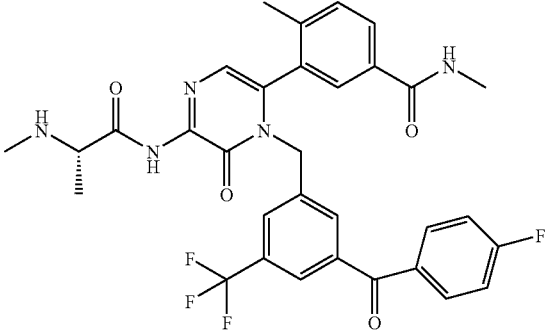 | 167 | 3-[1-[3-Trifluoromethyl-5-(4-fluoro-benzoyl)-benzyl]-5-((S)-2-methylamino-propionylamino)-6-oxo-1,6-dihydro-pyrazin-2-yl]-4,N-dimethyl-benzamide | 624.2 |

TABLE 2-continued

| Structure | Example No. | name | MS ESI (M + H)+ |
|---|---|---|---|
| 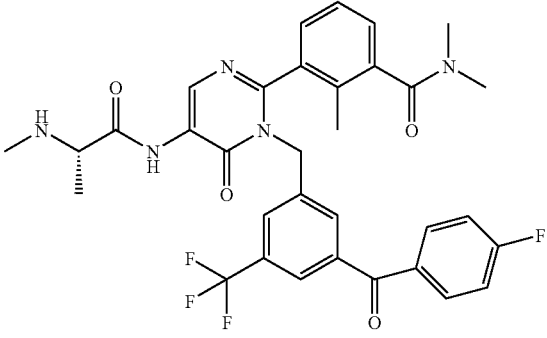 | 168 | 3-[1-[3-Fluoro-5-(4-fluoro-benzoyl)-benzyl]-5-((S)-2-methylamino-propionylamino)-6-oxo-1,6-dihydro-pyrimidin-2-yl]-2,N,N-trimethyl-benzamide | 638.2 |
| 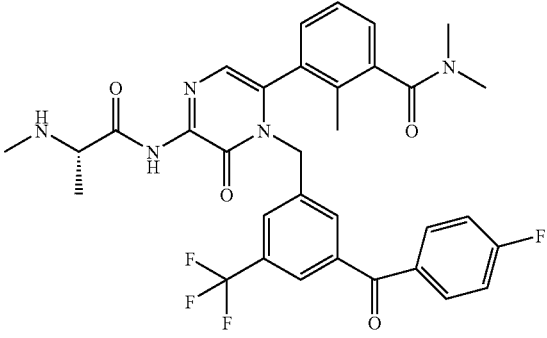 | 169 | 3-[1-[3-Fluoro-5-(4-fluoro-benzoyl)-benzyl]-5-((S)-2-methylamino-propionylamino)-6-oxo-1,6-dihydro-pyrazin-2-yl]-2,N,N-trimethyl-benzamide | 638.2 |
| 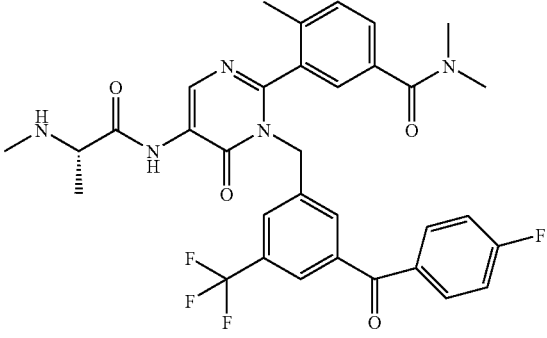 | 170 | 3-[1-[3-Trifluoromethyl-5-(4-fluoro-benzoyl)-benzyl]-5-((S)-2-methylamino-propionylamino)-6-oxo-1,6-dihydro-pyrimidin-2-yl]-4,N,N-trimethyl-benzamide | 638.2 |
| 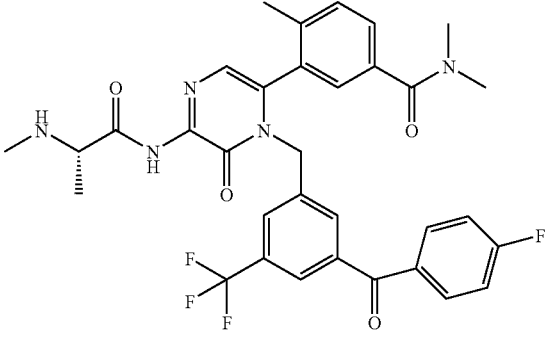 | 171 | 3-[1-[3-Trifluoromethyl-5-(4-fluoro-benzoyl)-benzyl]-5-((S)-2-methylamino-propionylamino)-6-oxo-1,6-dihydro-pyrazin-2-yl]-4,N,N-trimethyl-benzamide | 638.2 |

TABLE 2-continued

| Structure | Example No. | name | MS ESI (M + H)+ |
|---|---|---|---|
| 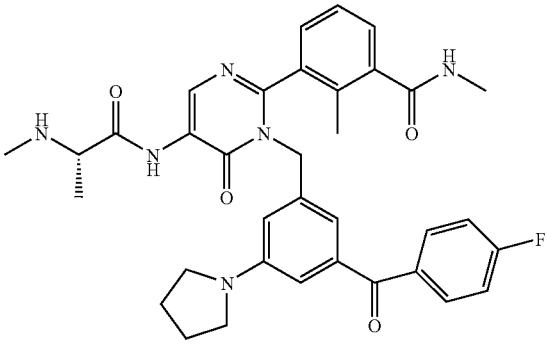 | 172 | 3-[1-[3-(4-Fluoro-benzoyl)-5-pyrrolidin-1-yl-benzyl]-5-((S)-2-methylamino-propionylamino)-6-oxo-1,6-dihydro-pyrimidin-2-yl]-2,N-dimethyl-benzamide | 625.3 |
| 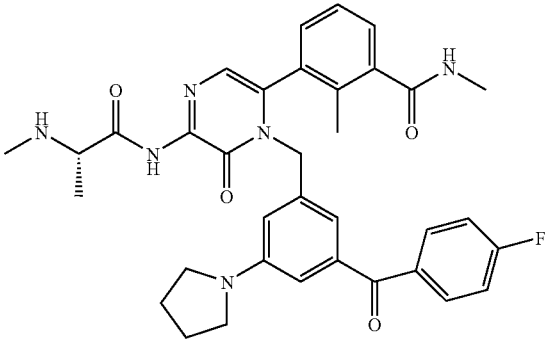 | 173 | 3-[1-[3-(4-Fluoro-benzoyl)-5-pyrrolidin-1-yl-benzyl]-5-((S)-2-methylamino-propionylamino)-6-oxo-1,6-dihydro-pyrazin-2-yl]-2,N-dimethyl-benzamide | 625.3 |
| 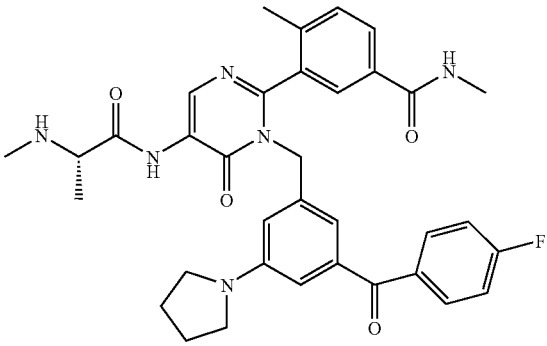 | 174 | 3-[1-[3-(4-Fluoro-benzoyl)-5-pyrrolidin-1-yl-benzyl]-5((S)-2-methylamino-propionylamino)-6-oxo-1,6-dihydro-pyrimidin-2-yl]-4,N-dimethyl-benzamide | 625.3 |
| 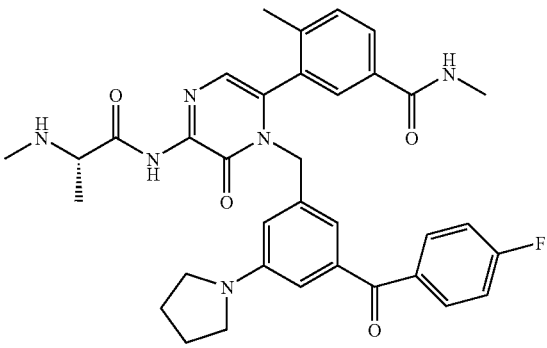 | 175 | 3-[1-[3-(4-Fluoro-benzoyl)-5-pyrrolidin-1-yl-benzyl]-5-((S)-2-methylamino-propionylamino)-6-oxo-1,6-dihydro-pyrazin-2-yl]-4,N-dimethyl-benzamide | 625.3 |

TABLE 2-continued

| Structure | Example No. | name | MS ESI (M + H)+ |
|---|---|---|---|
| 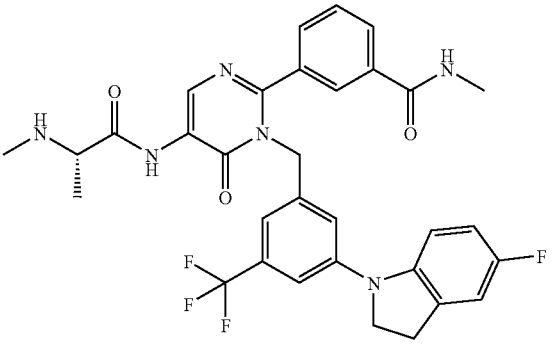 | 176 | 3-[1-[3-Trifluoromethyl-5-(5-fluoro-2,3-dihydro-indol-1-yl)-benzyl]-5-((S)-2-methylamino-propionylamino)-6-oxo-1,6-dihydro-pyrimidin-2-yl]-N-methyl-benzamide | 623.6 |
| 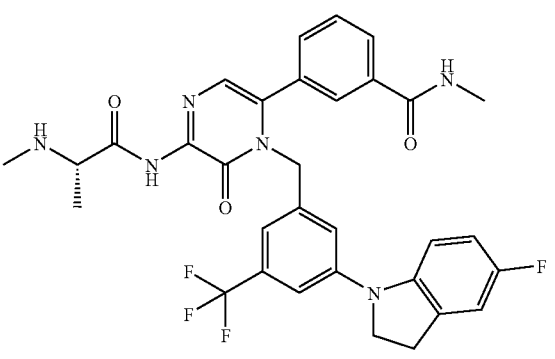 | 177 | 3-[1-[3-Trifluoromethyl-5-(5-fluoro-2,3-dihydro-indol-1-yl)-benzyl]-5-((S)-2-methylamino-propionylamino)-6-oxo-1,6-dihydro-pyrazin-2-yl]-N-methyl-benzamide | 623.6 |
| 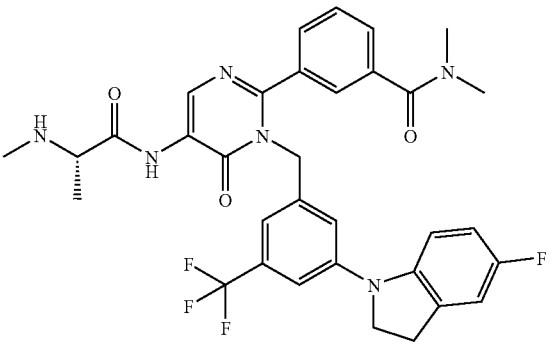 | 178 | 3-[1-[3-Trifluoromethyl-5-(5-fluoro-2,3-dihydro-indol-1-yl)-benzyl]-5-((S)-2-methylamino-propionylamino)-6-oxo-1,6-dihydro-pyrimidin-2-yl]-N,N-dimethyl-benzamide | 637.2 |
| 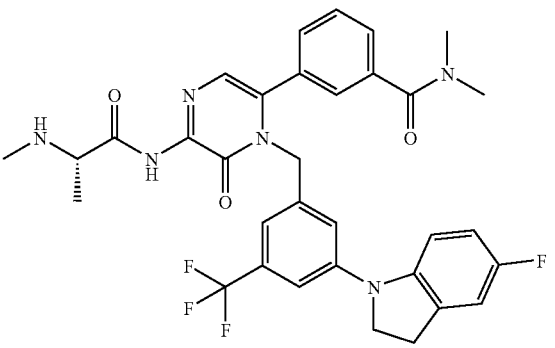 | 179 | 3-[1-[3-Trifluoromethyl-5-(5-fluoro-2,3-dihydro-indol-1-yl)-benzyl]-5-((S)-2-methylamino-propionylamino)-6-oxo-1,6-dihydro-pyrazin-2-yl]-N,N-dimethyl-benzamide | 637.2 |

TABLE 2-continued

| Structure | Example No. | name | MS ESI (M + H)+ |
|---|---|---|---|
| 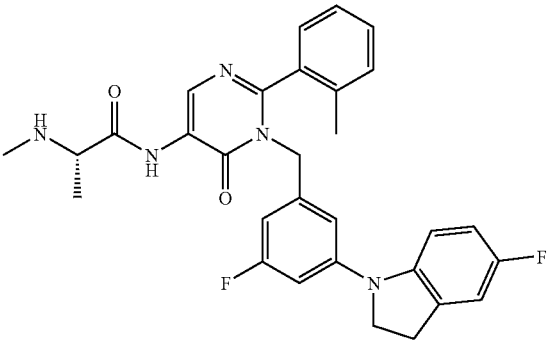 | 180 | (S)-N-{1-[3-Fluoro-5-(5-fluoro-2,3-dihydro-indol-1-yl)-benzyl]-6-oxo-2-o-tolyl-1,6-dihydro-pyrimidin-5-yl}-2-methylamino-propionamide | 530.2 |
| 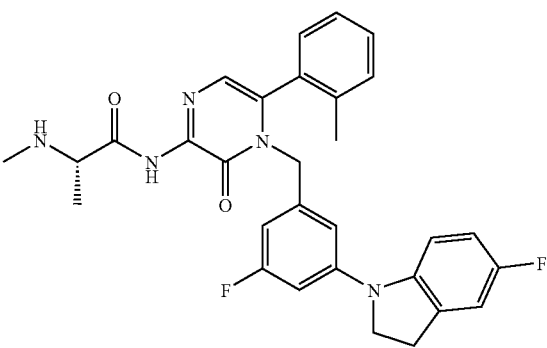 | 181 | (S)-N-{4-[3-Fluoro-5-(5-fluoro-2,3-dihydro-indol-1-yl)-benzyl]-3-oxo-5-o-tolyl-3,4-dihydro-pyrazin-2-yl}-2-methylamino-propionamide | 530.2 |
| 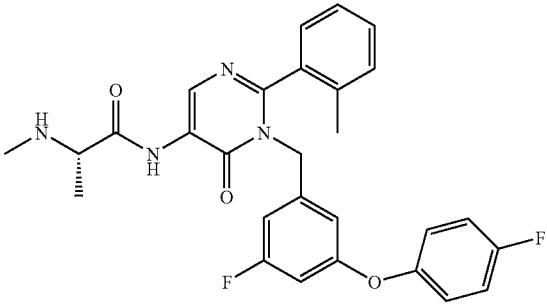 | 182 | (S)-N-{1-[3-Fluoro-5-(4-fluoro-phenoxy)-benzyl]-6-oxo-2-o-tolyl-1,6-dihydro-pyrimidin-5-yl}-2-methylamino-propionamide | 505.2 |
| 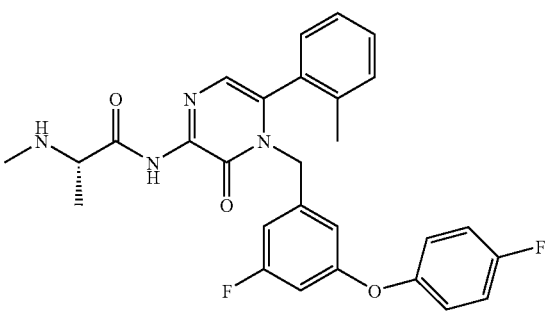 | 183 | (S)-N-{-[4-[3-Fluoro-5-(4-fluoro-phenoxy)-benzyl]-3-oxo-5-o-tolyl-3,4-dihydro-pyrazin-2-yl}-2-methylamino-propionamide | 505.2 |

Biological Activity

TR-FRET is a proximity based detection method that requires a donor label, Europium (Eu-Streptavidin) and an acceptor label, APC (anti-GST-APC). In the absence of a competitive small molecule, the GST-BIR3 fusion protein binds specifically to its natural ligand Smac, or, in the context of this assay, to B-Smac (biotinylated Smac). The subsequent addition of donor and acceptor labeled complexes results in Europium (via the Streptavidin:Biotin interaction) and APC (via the anti-GST:GST-BIR3 interaction) coming into proximity allowing fluorescence energy transfer. The excitation of Europium, by a 615 nM wavelength, results in the transfer of a singlet oxygen to the APC acceptor complex. This results in the excitation of APC and a release of energy detected at a wavelength of 665 nM. Compounds with Bir3 binding activity compete with Biotin-Smac for occupancy of the surface groove on GST-BIR3 resulting in concentration-dependent loss of signal. Assay plates are read on a multi-label plate reader using excitation and emission filters Europium 615 nM and APC 665 nM, respectively and the optical module Lance Eu/APC Dual 452. The $IC_{50}$ (concentration of compound inhibiting 50% of Smac binding) is determined using XLfit4 (IDBS) or Spotfire. Compounds 29-30 have $IC_{50}$ Range of 0.001-10 uM.

The above preferred embodiments are given to illustrate the scope and spirit of the present invention. The descriptions provided herein will make apparent to those skilled in the art other embodiments and examples. These other embodiments and examples are within the contemplation of the present invention. Therefore, the present invention should be limited only by the appended claims.

What is claimed is:

1. A compound selected from the group consisting of
(S)—N-(5-(4-Fluoro-phenyl)-3-oxo-4-{[(R)-(1,2,3,4-tetrahydro-naphthalen-1-yl)carbamoyl]-methyl}-3,4-dihydro-pyrazin-2-yl)-2-methylamino-propionamide;
(S)—N-{5-(4-Fluoro-phenyl)-4-[2-((R)-methyl-1,2,3,4-tetrahydro-naphthalen-1-yl-amino)-acetyl]-3-oxo-3,4-dihydro-pyrazin-2-yl}-2-methylamino-propionamide;
(S)—N-{5-(4-Fluoro-phenyl)-4-[2-((R)-methyl-1,2,3,4-tetrahydro-naphthalen-1-yl-amino)-ethyl]-3-oxo-3,4-dihydro-pyrazin-2-yl}-2-methylamino-propionamide;
(S)—N-[4-[(4-Fluoro-benzylcarbamoyl)-methyl]-5-(4-fluoro-phenyl)-3-oxo-3,4-dihydro-pyrazin-2-yl]-2-methylamino-propionamide;
(S)—N-[4-[5-(4-Fluoro-benzoyl)-pyridin-3-ylmethyl]-5-(4-fluoro-phenyl)-3-oxo-3,4-dihydro-pyrazin-2-yl]-2-methylamino-propionamide;
(S)—N4-[5-(4-Fluoro-benzoyl)-pyridin-3-yl]-5-(4-fluoro-phenyl)-3-oxo-3,4-dihydro-pyrazin-2-yl]-2-methylamino-propionamide;
(S)—N-(5-(4-Fluoro-phenyl)-4-{5-[(4-fluoro-phenyl)-methyl-amino]-pyridin-3-ylmethyl}-3-oxo-3,4-dihydro-pyrazin-2-yl)-2-methylamino-propionamide;
(S)—N-[4-[5-(5-Fluoro-2,3-dihydro-indol-1-yl)-pyridin-3-ylmethyl]-5-(4-fluoro-phenyl)-3-oxo-3,4-dihydro-pyrazin-2-yl]-2-methylamino-propionamide;
(S)—N-[4-[5-(5-Fluoro-3-methyl-indol-1-yl)-pyridin-3-ylmethyl]-5-(4-fluoro-phenyl)-3-oxo-3,4-dihydro-pyrazin-2-yl]-2-methylamino-propionamide;
(S)—N-{5-(4-Fluoro-phenyl)-4-[1-(4-fluoro-phenyl)-1H-indol-4-ylmethyl]-3-oxo-3,4-dihydro-pyrazin-2-yl}-2-methylamino-propionamide;
(S)—N-[4-(5-Benzo[1,3]dioxol-5-yl-pyridin-3-ylmethyl]-5-(4-fluoro-phen yl)-3-oxo-3,4-dihydro-pyrazin-2-yl]-2-methylamino-propionamide;
(S)—N-4-[5-(4-Fluoro-phenoxy)-pyridin-3-ylmethyl]-5-(4-fluoro-phenyl)-3-oxo-3,4-dihydro-pyrazin-2-yl]-2-methylamino-propionamide;
(S)—N-{4-[4-(4-Fluoro-benzoyl)-thiazol-2-ylmethyl]-3-oxo-5-phenyl-3,4-dihydro-pyrazin-2-yl}-2-methylamino-propionamide;
(S)—N-[4-[4-(4-Fluoro-benzoyl)-thiazol-2-ylmethyl]-5-(4-fluoro-phenyl)-3-oxo-3,4-dihydro-pyrazin-2-yl]-2-methylamino-propionamide;
(S)-2-Methylamino-N-(3-oxo-5-phenyl-4-{[(R)-(1,2,3,4-tetrahydro-naphthalen-1-yl)carbamoyl]-methyl}-3,4-dihydro-pyrazin-2-yl)-propionamide;
(S)—N-(5-(3-Trifluoromethyl-phenyl)-3-oxo-4-{[(R)-(1,2,3,4-tetrahydro-naphthalen-1-yl)carbamoyl]-methyl]-3,4-dihydro-pyrazin-2-yl}-2-methylamino-propionamide;
(S)—N-{5-(4-Fluoro-phenyl)-4-[((R)-methyl-1,2,3,4-tetrahydro-naphthalen-1-yl-carbamoyl)-methyl]-3-oxo-3,4-dihydro-pyrazin-2-yl}-2-methylamino-propionamide;
(S)-2-Methylamino-N-(3-oxo-4-{[(R)-(1,2,3,4-tetrahydro-naphthalen-1-yl)carbamoyl]-methyl}-5-o-tolyl-3,4-dihydro-pyrazin-2-yl)-propionamide;
(S)—N-(5-(4-Fluoro-2-methyl-phenyl)-3-oxo-4-{[(R)-(1,2,3,4-tetrahydro-naphthalen-1-yl)carbamoyl]-methyl}-3,4-dihydro-pyrazin-2-yl)-2-methylamino-propionamide;
(S)—N-(5-(2,4-Dimethyl-phenyl)-3-oxo-4-{[(R)-(1,2,3,4-tetrahydro-naphthalen-1-yl)carbamoyl]-methyl}-3,4-dihydro-pyrazin-2-yl)-2-methylamino-propionamide;
(S)—N-(5-(4-Fluoro-2-methyl-phenyl)-3-oxo-4-{[(R)-(1,2,3,4-tetrahydro-naphthalen-1-yl)carbamoyl]-methyl}-3,4-dihydro-pyrazin-2-yl)-2-methylamino-butyramide;
(S)—N-[4-[(1-Benzyl-2-phenyl-ethylcarbamoyl)-methyl]-5-(4-fluoro-phenyl)-3-oxo-3,4-dihydro-pyrazin-2-yl]-2-methylamino-propionamide;
(S)—N44-[(Diphenethylcarbamoyl)-methyl]-5-(4-fluoro-phenyl)-3-oxo-3,4-dihydro-pyrazin-2-yl]-2-methylamino-propionamide;
(S)—N-[4-(2-Carbazol-9-yl-2-oxo-ethyl)-5-(4-fluoro-phenyl)-3-oxo-3,4-dihydro-pyrazin-2-yl]-2-methylamino-propionamide;
(S)—N-[4-[2-(1,3-Dihydro-isoindol-2-yl)-2-oxo-ethyl]-5-(4-fluoro-phenyl)-3-oxo-3,4-dihydro-pyrazin-2-yl]-2-methylamino-propionamide;
(S)—N-{5-(4-Fluoro-phenyl)-4-[2-(indan-2-yloxy)-ethyl]-3-oxo-3,4-dihydro-pyrazin-2-yl}-2-methylamino-propionamide;
(S)—N-{5-Benzo[1,3]dioxol-5-yl-4-[5-(4-fluoro-benzoyl)-pyridin-3-ylmethyl]-3-oxo-3,4-dihydro-pyrazin-2-yl}-2-methylamino-propionamide;
3-[1-[5-(5-Fluoro-3-methyl-indol-1-yl)-pyridin-3-ylmethyl]-5-((S)-2-methylamino-propionylamino)-6-oxo-1,6-dihydro-pyrazin-2-yl]-N-methyl-benzamide;
3-[1-[5-(5-Fluoro-3-methyl-indol-1-yl)-pyridin-3-ylmethyl]-5-((S)-2-methylamino-propionylamino)-6-oxo-1,6-dihydro-pyrazin-2-yl]-N,N-dimethyl-benzamide;
(S)—N-{5-(3-Cyano-phenyl)-4-[3-(4-fluoro-benzoyl)-5-morpholin-4-yl-benzyl]-3-oxo-3,4-dihydro-pyrazin-2-yl}-2-methylamino-propionamide;
(S)—N-{5-(3-Cyano-phenyl)-4-[5-(5-fluoro-3-methyl-indol-1-yl)-pyridin-3-ylmethyl]-3-oxo-3,4-dihydro-pyrazin-2-yl}-2-methylamino-propionamide;
3-[1-[3-(4-Fluoro-benzoyl)-5-morpholin-4-yl-benzyl]-5-((S)-2-methylamino-propionylamino)-6-oxo-1,6-dihydro-pyrazin-2-yl]-N-methyl-benzamide;
N-Ethyl-3-[1-[3-(4-fluoro-benzoyl)-5-morpholin-4-yl-benzyl]-5-((S)-2-methylamino-propionylamino)-6-oxo-1,6-dihydro-pyrazin-2-yl]-benzamide;
3-[1-[3-(4-Fluoro-benzoyl)-5-morpholin-4-yl-benzyl]-5-((S)-2-methylamino-propionylamino)-6-oxo-1,6-dihydro-pyrazin-2-yl]-N-isobutyl-benzamide;
(S)—N-{5-(3-Acetylamino-phenyl)-4-[5-(4-fluoro-benzoyl)-pyridin-3-ylmethyl]-3-oxo-3,4-dihydro-pyrazin-2-yl}-2-methylamino-propionamide;
(S)—N-{4-[5-(4-Fluoro-benzoyl)-pyridin-3-ylmethyl]-3-oxo-5-o-tolyl-3,4-dihydro-pyrazin-2-yl}-2-methylamino-propionamide;
(S)—N-{4-[5-(5-Fluoro-indol-1-yl)-pyridin-3-ylmethyl]-3-oxo-5-o-tolyl-3,4-dihydro-pyrazin-2-yl}-2-methylamino-propionamide;
3-[1-[5-(4-Fluoro-benzoyl)-pyridin-3-ylmethyl]-5-((S)-2-methylamino-propionylamino)-6-oxo-1,6-dihydro-pyrazin-2-yl]-N-methyl-benzamide;
(S)—N-[4-[5-(4-Fluoro-benzoyl)-pyridin-3-ylmethyl]-5-(4-methoxy-pyridin-3-yl)-3-oxo-3,4-dihydro-pyrazin-2-yl]-2-methylamino-propionamide;

(S)—N-{5-Benzo[1,2,5]oxadiazol-5-yl-4-[5-(4-fluoro-benzoyl)-pyridin-3-ylmethyl]-3-oxo-3,4-dihydro-pyrazin-2-yl}-2-methylamino-propionamide;

(S)—N-{5-Benzo[1,2,5]oxadiazol-5-yl-4-[5-(5-fluoro-3-methyl-indol-1-yl)-pyridin-3-ylmethyl]-3-oxo-3,4-dihydro-pyrazin-2-yl}-2-methylamino-propionamide;

(S)—N-{4-[5-(4-Fluoro-benzoyl)-pyridin-3-ylmethyl]-3-oxo-3,4-dihydro-pyrazin-2-yl}-2-methylamino-propionamide;

[3-((S)-2-Methylamino-propionylamino)-2-oxo-6-phenyl-2H-pyrazin-1-yl]-acetic acid 1,2,3,4-tetrahydro-naphthalen-1-yl ester;

(S)—N-[4-[5-(5-Fluoro-3-methyl-indol-1-yl)-pyridin-3-ylmethyl]-3-oxo-5-(2-pyrrolidin-1-yl-pyridin-4-yl)-3,4-dihydro-pyrazin-2-yl]-2-methylamino-propionamide;

(S)—N-{4-[5-(5-Fluoro-indol-1-yl)-pyridin-3-ylmethyl]-3-oxo-5-phenyl-3,4-dihydro-pyrazin-2-yl}-2-methylamino-propionamide;

(S)—N-{4-[5-(5-Fluoro-3-methyl-indol-1-yl)-pyridin-3-ylmethyl]-3-oxo-5-phenyl-3,4-dihydro-pyrazin-2-yl}-2-methylamino-propionamide;

(S)—N-{4-[5-(5-Fluoro-3-methyl-indol-1-yl)-pyridin-3-ylmethyl]-3-oxo-5-[3-(2H-tetrazol-5-yl)-phenyl]-3,4-dihydro-pyrazin-2-yl}-2-methylamino-propionamide;

(S)—N-{4-[5-(5-Fluoro-3-methyl-indol-1-yl)-pyridin-3-ylmethyl]-3-oxo-5-[4-(1H-tetrazol-5-yl)-phenyl]-3,4-dihydro-pyrazin-2-yl}-2-methylamino-propionamide;

(S)—N-{4-[5-(5-Fluoro-3-methyl-indol-1-yl)-pyridin-3-ylmethyl]-5-[3-(2-methyl-2H-tetrazol-5-yl)-phenyl]-3-oxo-3,4-dihydro-pyrazin-2-yl}-2-methylamino-propionamide;

(S)—N-{4-[5-(5-Fluoro-3-methyl-indol-1-yl)-pyridin-3-ylmethyl]-5-[3-(1-methyl-1H-tetrazol-5-yl)-phenyl]-3-oxo-3,4-dihydro-pyrazin-2-yl}-2-methylamino-propionamide;

(S)—N-{4-[5-(5-Fluoro-3-methyl-indol-1-yl)-pyridin-3-ylmethyl]-3-oxo-5-[3-(1H-[1,2,3]triazol-4-yl)-phenyl]-3,4-dihydro-pyrazin-2-yl}-2-methylamino-propionamide;

(S)—N-{4-[5-(5-Fluoro-3-methyl-indol-1-yl)-pyridin-3-ylmethyl]-3-oxo-5-[4-(3H-[1,2,3]triazol-4-yl)-phenyl]-3,4-dihydro-pyrazin-2-yl}-2-methylamino-propionamide;

3-[1-[6-(5-Fluoro-3-methyl-indol-1-yl)-2-methyl-pyrimidin-4-ylmethyl]-5-((S)-2-methylamino-propionylamino)-6-oxo-1,6-dihydro-pyrazin-2-yl]-N,N-dimethyl-benzamide;

3-[1-[5-(5-Fluoro-3-methyl-indol-1-yl)-pyridin-3-ylmethyl]-5-((S)-2-methylamino-propionylamino)-6-oxo-1,6-dihydro-pyrazin-2-yl]-N,N-dimethyl-benzamide;

3-[1-[5-(5-Fluoro-3-methyl-indol-1-yl)-pyridin-3-ylmethyl]-5-((S)-2-methylamino-propionylamino)-6-oxo-1,6-dihydro-pyrazin-2-yl]-N-methyl-benzamide;

3-[1-[6-(5-Fluoro-3-methyl-indol-1-yl)-2-methyl-pyrimidin-4-ylmethyl]-5-((S)-2-methylamino-propionylamino)-6-oxo-1,6-dihydro-pyrazin-2-yl]-N-methyl-benzamide;

3-{5-((R)-3-Fluoro-2-methylamino-propionylamino)-1-[5-(5-fluoro-3-methyl-indol-1-yl)-pyridin-3-ylmethyl]-6-oxo-1,6-dihydro-pyrazin-2-yl}-N,N-dimethyl-benzamide;

(R)—N-{5-[3-Cyano-phenyl)-4-[3-(4-fluoro-benzoyl)-5-morpholin-4-yl-benzyl]-3-oxo-3,4-dihydro-pyrazin-2-yl}-3-fluoro-2-methylamino-propionamide;

3-[1-[3-(5-Fluoro-3-methyl-indol-1-yl)-benzyl]-5-((S)-2-methylamino-propionylamino)-6-oxo-1,6-dihydro-pyrazin-2-yl]-N,N-dimethyl-benzamide;

3-[1-[3-Fluoro-5-(5-fluoro-3-methyl-indol-1-yl)-benzyl]-5-((S)-2-methylamino-propionylamino)-6-oxo-1,6-dihydro-pyrazin-2-yl]-N,N-dimethyl-benzamide;

3-[1-[3-Trifluoromethyl-5-(5-fluoro-3-methyl-indol-1-yl)-benzyl]-5-((S)-2-methylamino-propionylamino)-6-oxo-1,6-dihydro-pyrazin-2-yl]-N,N-dimethyl-benzamide;

3-[1-[3-(5-Fluoro-3-methyl-indol-1-yl)-5-pyrrolidin-1-yl-benzyl]-5-((S)-2-methylamino-propionylamino)-6-oxo-1,6-dihydro-pyrazin-2-yl]-N,N-dimethyl-benzamide;

3-[1-[3-(5-Fluoro-3-methyl-indol-1-yl)-benzyl]-5-((S)-2-methylamino-propionylamino)-6-oxo-1,6-dihydro-pyrazin-2-yl]-N-methyl-benzamide;

3-[1-[3-Fluoro-5-(5-fluoro-3-methyl-indol-1-yl)-benzyl]-5-((S)-2-methylamino-propionylamino)-6-oxo-1,6-dihydro-pyrazin-2-yl]-N-methyl-benzamide;

3-[1-[3-Trifluoromethyl-5-(5-fluoro-3-methyl-indol-1-yl)-benzyl]-5-((S)-2-methylamino-propionylamino)-6-oxo-1,6-dihydro-pyrazin-2-yl]-N-methyl-benzamide;

3-[1-[3-(5-Fluoro-3-methyl-indol-1-yl)-5-pyrrolidin-1-yl-benzyl]-5-((S)-2-methylamino-propionylamino)-6-oxo-1,6-dihydro-pyrazin-2-yl]-N-methyl-benzamide;

3-[1-[3-(4-Fluoro-benzoyl)-5-trifluoromethyl-yl-benzyl]-5-((S)-2-methylamino-propionylamino)-6-oxo-1,6-dihydro-pyrazin-2-yl]-N-methyl-benzamide;

3-[1-[3-(4-Fluoro-benzoyl)-5-pyrrolidin-1-yl-benzyl]-5-((S)-2-methylamino-propionylamino)-6-oxo-1,6-dihydro-pyrazin-2-yl]-N-methyl-benzamide;

3-[1-[5-(5-Fluoro-3-methyl-indol-1-yl)-pyridin-3-ylmethyl]-5-((S)-2-methylamino-propionylamino)-6-oxo-1,6-dihydro-pyrazin-2-yl]-2,N-dimethyl-benzamide;

3-[1-[5-(5-Fluoro-3-methyl-indol-1-yl)-pyridin-3-ylmethyl]-5-((S)-2-methylamino-propionylamino)-6-oxo-1,6-dihydro-pyrazin-2-yl]-4,N-dimethyl-benzamide;

3-[1-[6-(5-Fluoro-3-methyl-indol-1-yl)-2-methyl-pyrimidin-4-ylmethyl]-5-((S)-2-methylamino-propionylamino)-6-oxo-1,6-dihydro-pyrazin-2-yl]-2,N-dimethyl-benzamide;

3-[1-[6-(5-Fluoro-3-methyl-indol-1-yl)-2-methyl-pyrimidin-4-ylmethyl]-5-((S)-2-methylamino-propionylamino)-6-oxo-1,6-dihydro-pyrazin-2-yl]-4,N-dimethyl-benzamide;

3-[1-[3-(4-Fluoro-benzoyl)-5-isopropyl-benzyl]-5-((S)-2-methylamino-propionylamino)-6-oxo-1,6-dihydro-pyrazin-2-yl]-4,N-dimethyl-benzamide;

3-[1-[3-(4-Fluoro-benzoyl)-5-isopropyl-benzyl]-5-((S)-2-methylamino-propionylamino)-6-oxo-1,6-dihydro-pyrazin-2-yl]-2,N-dimethyl-benzamide;

3-[1-[3-(5-Fluoro-3-methyl-indol-1-yl)-benzyl]-5-((S)-2-methylamino-propionylamino)-6-oxo-1,6-dihydro-pyrazin-2-yl]-2,N-dimethyl-benzamide;

3-[1-[3-(5-Fluoro-3-methyl-indol-1-yl)-benzyl]-5-((S)-2-methylamino-propionylamino)-6-oxo-1,6-dihydro-pyrazin-2-yl]-2,N,N-trimethyl-benzamide;

3-[1-[3-(5-Fluoro-3-methyl-indol-1-yl)-benzyl]-5-((S)-2-methylamino-propionylamino)-6-oxo-1,6-dihydro-pyrazin-2-yl]-4,N-dimethyl-benzamide;

3-[1-[3-(5-Fluoro-3-methyl-indol-1-yl)-benzyl]-5-((S)-2-methylamino-propionylamino)-6-oxo-1,6-dihydro-pyrazin-2-yl]-4,N,N-trimethyl-benzamide;

3-[1-[3-Fluoro-5-(4-fluoro-benzoyl)-benzyl]-5-((S)-2-methylamino-propionylamino)-6-oxo-1,6-dihydro-pyrazin-2-yl]-2,N-dimethyl-benzamide;

3-[1-[3-Fluoro-5-(4-fluoro-benzoyl)-benzyl]-5-((S)-2-methylamino-propionylamino)-6-oxo-1,6-dihydro-pyrazin-2-yl]-4,N-dimethyl-benzamide;

3-[1-[3-Trifluoromethyl-5-(4-fluoro-benzoyl)-benzyl]-5-((S)-2-methylamino-propionylamino)-6-oxo-1,6-dihydro-pyrazin-2-yl]-2,N-dimethyl-benzamide;

3-[1-[3-Trifluoromethyl-5-(4-fluoro-benzoyl)-benzyl]-5-((S)-2-methylamino-propionylamino)-6-oxo-1,6-dihydro-pyrazin-2-yl]-4,N-dimethyl-benzamide;

3-[1-[3-Fluoro-5-(4-fluoro-benzoyl)-benzyl]-5-((S)-2-methylamino-propionylamino)-6-oxo-1,6-dihydro-pyrazin-2-yl]-2,N,N-trimethyl-benzamide;

3-[1-[3-Trifluoromethyl-5-(4-fluoro-benzoyl)-benzyl]-5-((S)-2-methylamino-propionylamino)-6-oxo-1,6-dihydro-pyrazin-2-yl]-4,N,N-trimethyl-benzamide;

3-[1-[3-(4-Fluoro-benzoyl)-5-pyrrolidin-1-yl-benzyl]-5-((S)-2-methylamino-propionylamino)-6-oxo-1,6-dihydro-pyrazin-2-yl]-2,N-dimethyl-benzamide;

3-[1-[3-(4-Fluoro-benzoyl)-5-pyrrolidin-1-yl-benzyl]-5-((S)-2-methylamino-propionylamino)-6-oxo-1,6-dihydro-pyrazin-2-yl]-4,N-dimethyl-benzamide;

3-[1-[3-Trifluoromethyl-5-(5-fluoro-2,3-dihydro-indol-1-yl)-benzyl]-5-((S)-2-methylamino-propionylamino)-6-oxo-1,6-dihydro-pyrazin-2-yl]-N-methyl-benzamide;

3-[1-[3-Trifluoromethyl-5-(5-fluoro-2,3-dihydro-indol-1-yl)-benzyl]-5-((S)-2-methylamino-propionylamino)-6-oxo-1,6-dihydro-pyrazin-2-yl]-N,N-dimethyl-benzamide;

(S)—N-{4-[3-Fluoro-5-(5-fluoro-2,3-dihydro-indol-1-yl)-benzyl]-3-oxo-5-o-tolyl-3,4-dihydro-pyrazin-2-yl}-2-methylamino-propionamide; and (S)—N-{4-[3-Fluoro-5-(4-fluoro-phenoxy)-benzyl]-3-oxo-5-o-tolyl-3,4-dihydro-pyrazin-2-yl}-2-methylamino-propionamide.

2. A pharmaceutical composition comprising a therapeutically effective amount of a compound according to claim 1 and a pharmaceutically acceptable carrier.

3. A compound which is (S)-2-Methylamino-N-(3-oxo-5-phenyl-4-{[(R)-(1,2,3,4-tetrahydro-naphthalen-1-yl)carbamoyl]-methyl}-3,4-dihydro-pyrazin-2-yl)-propionamide, or a pharmaceutically acceptable salt thereof.

4. A pharmaceutical composition comprising a therapeutically effective amount of a compound according to claim 3 and a pharmaceutically acceptable carrier.

* * * * *